United States Patent
Ambati et al.

(10) Patent No.: US 9,453,226 B2
(45) Date of Patent: *Sep. 27, 2016

(54) **PROTECTION OF CELLS FROM *ALU*-RNA-INDUCED DEGENERATION AND INHIBITORS FOR PROTECTING CELLS**

(71) Applicant: UNIVERSITY OF KENTUCKY RESEARCH FOUNDATION, Lexington, KY (US)

(72) Inventors: Jayakrishna Ambati, Lexington, KY (US); Valeria Tarallo, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/158,357

(22) Filed: Jan. 17, 2014

(65) Prior Publication Data

US 2014/0178309 A1   Jun. 26, 2014

Related U.S. Application Data

(63) Continuation-in-part of application No. PCT/US2012/046928, filed on Jul. 16, 2012.

(60) Provisional application No. 61/508,867, filed on Jul. 18, 2011, provisional application No. 61/543,038, filed on Oct. 4, 2011.

(51) Int. Cl.
| | |
|---|---|
| *A61K 48/00* | (2006.01) |
| *C12N 15/113* | (2010.01) |
| *A61K 31/713* | (2006.01) |
| *A61K 38/08* | (2006.01) |
| *A61K 38/17* | (2006.01) |
| *C07K 7/06* | (2006.01) |
| *C07K 16/24* | (2006.01) |
| *G01N 33/50* | (2006.01) |
| *G01N 33/68* | (2006.01) |
| *A61K 49/00* | (2006.01) |
| *C07K 14/00* | (2006.01) |

(52) U.S. Cl.
CPC ......... *C12N 15/1136* (2013.01); *A61K 31/713* (2013.01); *A61K 38/08* (2013.01); *A61K 38/1709* (2013.01); *A61K 49/005* (2013.01); *A61K 49/0008* (2013.01); *C07K 7/06* (2013.01); *C07K 14/00* (2013.01); *C07K 16/244* (2013.01); *G01N 33/5023* (2013.01); *G01N 33/5041* (2013.01); *G01N 33/6869* (2013.01); *C07K 2317/76* (2013.01); *G01N 2333/54* (2013.01)

(58) Field of Classification Search
CPC . A61K 48/00; A61K 31/713; C12N 15/1136
USPC ........................................................ 514/44
See application file for complete search history.

(56) References Cited

U.S. PATENT DOCUMENTS

| | | | |
|---|---|---|---|
| 7,033,830 B2 | 4/2006 | Karras et al. | |
| 7,879,992 B2 | 2/2011 | Vickers et al. | |
| 2007/0287756 A1 | 12/2007 | Nakazawa | |
| 2010/0113760 A1 | 5/2010 | Khvorova et al. | |
| 2012/0177632 A1* | 7/2012 | Shinohara et al. | 424/130.1 |
| 2013/0137642 A1* | 5/2013 | Vavvas et al. | 514/18.9 |

FOREIGN PATENT DOCUMENTS

| | | |
|---|---|---|
| EP | 1746167 A1 | 1/2007 |
| WO | 0047218 A1 | 8/2000 |
| WO | 2004045543 A2 | 6/2004 |
| WO | 2007077042 A1 | 7/2007 |
| WO | 2008070579 A2 | 6/2008 |
| WO | 2010017436 A2 | 2/2010 |
| WO | 2011153234 A2 | 12/2011 |

OTHER PUBLICATIONS

Schroder et al. (Science, Jan. 2010: 296-300).*
Wong, et al., Critical role for NLRP3 in necrotic death triggered by Mycobacterium tuberculosis; Cellular Microbiology; 2011, 13(9), pp. 1971-1984.
Kumar, M.V., Nagineni, C.N., Chin, M.S., Hooks, J.J., and Detrick, B. (2004). Innate immunity in the retina: Toll-like receptor (TLR) signaling in human retinal pigment epithelial cells. J Neuroimmunol 153, 7-15.
Lamkanfi, M. et al. Glyburide inhibits the Cryopyrin/Nalp3 inflammasome. J Cell Biol 187, 61-70, doi:10.1083/cb.200903124 (2009).
Lander, E.S., Linton, L.M., Birren, B., Nusbaum, C., Zody, M.C., Baldwin, J., Devon, K., Dewar, K., Doyle, M., FitzHugh, W., et al. (2001). Initial sequencing and analysis of the human genome. Nature 409, 860-921.
Latz, E. (2010). NOX-free inflammasome activation. Blood 116, 1393-1394.
Lee, S. H., Stehlik, C. & Reed, J. C. Cop, a caspase recruitment domain-containing protein and inhibitor of caspase-1 activation processing. J Biol Chem 276, 34495-34500, doi:10.1074/jbc.M101415200 (2001).
Li, H., Ambade, A. & Re, F. Cutting edge: Necrosis activates the NLRP3 inflammasome. J Immunol 183, 1528-1532, doi:10.4049/jimmunol.0901080 (2009).

(Continued)

*Primary Examiner* — Kimberly Chong
(74) *Attorney, Agent, or Firm* — Stites & Harbison PLLC; Mandy Wilson Decker

(57) ABSTRACT

A method of protecting a cell includes inhibiting an inflammasome, MyD88, IL-18, VDAC1, VDAC2, caspase-8, and/or NFκB of the cell. Administering an inhibitor of MyD88, IL-18, VDAC1, VDAC2, caspase-8, and/or NFκB can protect the cell from Alu-RNA-induced degeneration. Protecting a cell, such as an retinal pigment epithelium (RPE), can be therapeutically useful in the context of age-related macular degeneration and geographic atrophy.

25 Claims, 23 Drawing Sheets

(56) References Cited

OTHER PUBLICATIONS

Li, Y., and Trush, M.A. (1998). Diphenyleneiodonium, an NAD(P)H oxidase inhibitor, also potently inhibits mitochondrial reactive oxygen species production. Biochem Biophys Res Commun 253, 295-299.

Li, M., Y. Zhou, et al. (2009). "The critical role of Toll-like receptor signaling pathways in the induction and progression of autoimmune diseases." Curr Mol Med 9(3): 365-374.

Lin, H., Xu, H., Liang, F.Q., Liang, H., Gupta, P., Havey, A.N., Boulton, M.E., and Godley, B.F. (2011). Mitochondrial DNA damage and repair in RPE associated with aging and age-related macular degeneration. Invest Ophthalmol Vis Sci 52, 3521-3529.

Loiarro, M., Sette, C., Gallo, G., Ciacci, A., Fanto, N., Mastroianni, D., Carminati, P., and Ruggiero, V. (2005). Peptide-mediated interference of TIR domain dimerization in MyD88 inhibits interleukin-1-dependent activation of NF-κB. J Biol Chem 280, 15809-15814.

Mariathasan, S. et al. Differential activation of the inflammasome by caspase-1 adaptors ASC and Ipaf. Nature 430, 213-218 (2004).

Mariathasan, S., Weiss, D.S., Newton, K., McBride, J., O'Rourke, K., Roose-Girma, M., Lee, W.P., Weinrauch, Y., Monack, D.M., and Dixit, V.M. (2006). Cryopyrin activates the inflammasome in response to toxins and ATP. Nature 440, 228-232.

Martinon, F., Mayor, A., and Tschopp, J. (2009). The inflammasomes: guardians of the body. Annu Rev Immunol 27, 229-265.

Miao, E.A., Leaf, I.A., Treuting, P.M., Mao, D.P., Dors, M., Sarkar, A., Warren, S.E., Wewers, M.D., and Aderem, A. (2010). Caspase-1-induced pyroptosis is an innate immune effector mechanism against intracellular bacteria. Nat Immunol 11, 1136-1142.

Munding, C. et al. The estrogen-responsive B box protein: a novel enhancer of interleukin-1beta secretion. Cell Death Differ 13, 1938-1949, doi:10.1038/sj.cdd.4401896 (2006).

Murphy, M.P. (2009). How mitochondria produce reactive oxygen species. Biochem J 417, 1-13.

Murphy, M.P., and Smith, R.A. (2007). Targeting antioxidants to mitochondria by conjugation to lipophilic cations. Annu Rev Pharmacol Toxicol 47, 629-656.

Muruve, D.A., Petrilli, V., Zaiss, A.K., White, L.R., Clark, S.A., Ross, P.J., Parks, R.J., and Tschopp, J. (2008). The inflammasome recognizes cytosolic microbial and host DNA and triggers an innate immune response. Nature 452, 103-107.

Muzio, M., Ni, J., Feng, P., and Dixit, V.M. (1997). IRAK (Pelle) family member IRAK-2 and MyD88 as proximal mediators of IL-1 signaling. Science 278, 1612-1615.

Nakahira, K., Haspel, J.A., Rathinam, V.A., Lee, S.J., Dolinay, T., Lam, H.C., Englert, J.A., Rabinovitch, M., Cernadas, M., Kim, H.P., et al. (2011). Autophagy proteins regulate innate immune responses by inhibiting the release of mitochondrial DNA mediated by the NALP3 inflammasome. Nat Immunol 12, 222-230.

Newman, Z. L. et al. Auranofin protects against anthrax lethal toxin-induced activation of the Nlrp1b inflammasome. Antimicrob Agents Chemother 55, 1028-1035, doi:10.1128/AAC.00772-10 (2011).

Ngo, V.N., Young, R.M., Schmitz, R., Jhavar, S., Xiao, W., Lim, K.H., Kohlhammer, H., Xu, W., Yang, Y., Zhao, H., et al. (2011). Oncogenically active MYD88 mutations in human lymphoma. Nature 470, 115-119.

Nordgaard, C.L., Karunadharma, P.P., Feng, X., Olsen, T.W., and Ferrington, D.A. (2008). Mitochondrial proteomics of the retinal pigment epithelium at progressive stages of age-related macular degeneration. Invest Ophthalmol Vis Sci 49, 2848-2855.

Novick, D. et al. Interleukin-18 binding protein: a novel modulator of the Th1 cytokine response. Immunity 10, 127-136 (1999).

O'Neill, L.A., and Bowie, A.G. (2007). The family of five: TIR-domain-containing adaptors in Toll-like receptor signalling. Nat Rev Immunol 7, 353-364.

Papin, S. et al. The SPRY domain of Pyrin, mutated in familial Mediterranean fever patients, interacts with inflammasome components and inhibits proIL-1beta processing. Cell Death Differ 14, 1457-1466, doi:10.1038/sj.cdd.4402142 (2007).

Picard, C., von Bernuth, H., Ghandil, P., Chrabieh, M., Levy, O., Arkwright, P.D., McDonald, D., Geha, R.S., Takada, H., Krause, J.C., et al. (2010). Clinical features and outcome of patients with IRAK-4 and MyD88 deficiency. Medicine (Baltimore) 89, 403-425.

Pichlmair, A., Lassnig, C., Eberle, C.A., Gorna, M.W., Baumann, C.L., Burkard, T.R., Burckstummer, T., Stefanovic, A., Krieger, S., Bennett, K.L., et al. (2011). IFIT1 is an antiviral protein that recognizes 5'-triphosphate RNA. Nat Immunol 12, 624-630.

Diao, Y., Wang, P., Qi, J., et al. (2012). "TLR-induced NF-kappaB activation regulates NLRP3 expression in murine macrophages." FEBS Lett 586(7): 1022-1026.

Schroder, K., and Tschopp, J. (2010). The inflammasomes. Cell 140, 821-832.

Schroder, K., Zhou, R., and Tschopp, J. (2010). The NLRP3 inflammasome: a sensor for metabolic danger? Science 327, 296-300.

Shaikh, T.H., Roy, A.M., Kim, J., Balzer, M.A., and Deininger, P.L. (1997). cDNAs derived from primary and small cytoplasmic Alu (scAlu) transcripts. J Mol Biol 271, 222-234.

Sinnett, D., Richer, C., Deragon, J.M., and Labuda, D. (1991). Alu RNA secondary structure consists of two independent 7 SL RNA-like folding units. J Biol Chem 266, 8675-8678.

Stennicke, H. R., Jurgensmeier, J. M., Shin, H., et al. (1998). "Pro-caspase-3 is a major physiologic target of caspase-8." J Biol Chem 273(42): 27084-27090.

Suzuki, N., Suzuki, S., Duncan, G.S., Millar, D.G., Wada, T., Mirtsos, C., Takada, H., Wakeham, A., Itie, A., Li, S., et al. (2002). Severe impairment of interleukin-1 and Toll-like receptor signalling in mice lacking IRAK-4. Nature 416, 750-756.

Takeda, A., Baffi, J.Z., Kleinman, M.E., Cho, W.G., Nozaki, M., Yamada, K., Kaneko, H., Albuquerque, R.J., Dridi, S., Saito, K., et al. (2009). CCR3 is a target for age-related macular degeneration diagnosis and therapy. Nature 460, 225-230.

Tarallo V, Hirano Y, Gelfand BD, Dridi S, Kerur N, Kim Y, Cho WG, Kaneko H, Fowler BJ, Bogdanovich S, Albuquerque RJ, Hauswirth WW, Chiodo VA, Kugel JF, Goodrich JA, Ponicsan SL, Chaudhuri G, Murphy MP, Dunaief JL, Ambati BK, Ogura Y, Yoo JW, Lee DK, Provost P, Hinton DR, Núñez G, Bath JZ, Kleinman ME, Ambati J. (2012). Diceri loss and Alu RNA induce age-related macular degeneration via the NLRP3 inflammasome and MyD88. Cell 149(4):847-859.

Thornberry, N.A., Bull, H.G., Calaycay, J.R., Chapman, K. T., Howard, A.D., Kostura, M.J., Miller, D.K., Molineaux, S.M., Weidner, J.R., Aunins, J., et al. (1992). A novel heterodimeric cysteine protease is required for interleukin-1 beta processing in monocytes. Nature 356, 768-774.

Trnka, J. Blaikie, F.H., Logan, A. Smith, R.A., and Murphy, M.P. (2009). Antioxidant properties of MitoTEMPOL and Its hydroxylamine. Free Radio Res 43, 4-12.

Tschopp, J., Martinon, F., and Burns, K. (2003). NALPs: a novel protein family involved in inflammation. Nat Rev Mol cell Biol 4, 95-104.

Tschopp, J., and Schroder, K. (2010). NLRP3 inflammasome activation: The convergence of multiple signalling pathways on ROS production? Nat Rev Immunol 10, 210-215.

van Bruggen, R., Koker, M.Y., Jansen, M., van Houdt, M., Roos, D., Kuijpers, T.W., and van den Berg, T.K. (2010). Human NLRP3 inflammasome activation is Nox1-4 independent. Blood 115, 5398-5400.

Vandenabeele, P., Vanden Berghe, T., and Festjens, N. (2006). Caspase inhibitors promote alternative cell death pathways. Sci STKE 2006, pe44.

von Bernuth, H., Picard, C., Jin, Z., Pankla, R., Xiao, H., Ku, C.L., Chrabieh, M., Mustapha, I.B., Ghandil, P., Camcioglu, Y., et al. (2008). Pyogenic bacterial infections in humans with MyD88 deficiency. Science 321, 691-696.

Yamamoto, M., Sato, S., Hemmi, H., Hoshino, K., Kaisho, T., Sanjo, H., Takeuchi, O., Sugiyama, M., Okabe, M., Takeda, K., et al. (2003). Role of adaptor TRIF in the MyD88-independent toll-like receptor signaling pathway. Science 301, 640-643.

Yang, Z. et al. Toll-like receptor 3 and geographic atrophy in age-related macular degeneration. N Engl J Med 359, 1456-1463 (2008).

(56) References Cited

OTHER PUBLICATIONS

Young, J. L. et al. The serpin proteinase inhibitor 9 is an endogenous inhibitor of interleukin 1beta-converting enzyme (caspase-1) activity in human vascular smooth muscle cells. J Exp Med 191, 1535-1544 (2000).
Thou, R., Yazdi, A.S., Menu, P., and Tschopp, J. (2011). A role for mitochondria in NLRP3 inflammasome activation. Nature 469, 221-225.
Zuany-Amorim, C., J. Hastewell, et al. (2002). "Toll-like receptors as potential therapeutic targets for multiple diseases." Nat Rev Drug Discov 1(10): 797-807.
Fujimoto et al., Choroidal Neovascularization Enhanced by Chlamydia pneumoniae via Toll-like Receptor 2 in the Retinal Pigment Epithelium, IOVS, 2010, vol. 51, No. 9, 4694-4702.
Ko et al., The Role of TLR4 Activation in Photoreceptor Mitochondrial Oxidative Stress, IOVS, 2011, vol. 52, No. 8, 5824-5835.
Tarallo et al: "DICER1 Loss and RNA Induce Age-Related Macular Degeneration via the NLRP3 Inflarrnnasome and MyD88", Cell, Cell Press, US, vol. 149, No. 4, Mar. 26, 2812 (2812-83-26), pp. 847-859.
Juliana et al: "Anti-inflarrnnatory Compounds Parthenolide and Bay 11-7882 are Direct Inhibitors of the Inflarrnnasome", Journal of Biological Chemistry, vol. 285, No. 13, Jan. 21, 2818 (2818-81-21), pp. 9792-9882.
Bulosan et al: "Inflammatory caspases are critical for enhanced cell death in the target tissue of Sjogren's syndrome before disease onset", Immunology and Cell Biology, vol. 87, No. 1, Oct. 21, 2008, pp. 81-90.
Tseng Wen A et al: "Activation of the NALP3 Inflammasome in Retinal Pigment Epithelial (RPE) Cells: Implications for AMD", Investigative Ophthalmology & Visual Science—IOVS, Association for Research in Vision and Ophthalmology, US, val. ARVO, May 1, 2011, pp. 1-2.
Hiroki Kaneko et al: "DICER1 deficit induces Alu RNA toxicity in age-related macular degeneration", Nature, val. 471, No. 7338, Mar. 17, 2011, pp. 325-330.
Abreu, M. T., M. Fukata, et al. (2005). "TLR signaling in the gut in health and disease." J Immunol 174(8): 4453-4460.
Adachi, O., Kawai, T., Takeda, K., Matsumoto, M., Tsutsui, H., Sakagami, M., Nakanishi, K., and Akira, S. (1998). Targeted disruption of the MyD88 gene results in loss of IL-1- and IL-18-mediated function. Immunity 9, 143-150.
Aeffner, F., Z. P. Traylor, et al. (2011). "Double-stranded RNA induces similar pulmonary dysfunction to respiratory syncytial virus in BALB/c mice." Am J Physiol Lung Cell Mol Physiol 301(1): L99-L109.
Akira, S., Uematsu, S., and Takeuchi, O. (2006). Pathogen recognition and innate immunity. Cell 124, 783-801.
Alexander, J. J. & Hauswirth, W. W. Adeno-associated viral vectors and the retina. Adv Exp Med Biol 613, 121-128 (2008).
Alexopoulou, L., Holt, A.C., Medzhitov, R., and Flavell, R.A. (2001). Recognition of double-stranded RNA and activation of NF-kappaB by Toll-like receptor 3. Nature 413, 732-738.
Aliprantis, A. O., Yang, R. B., Weiss, D. S., et al. (2000). "The apoptotic signaling pathway activated by Toll-like receptor-2." EMBO J 19(13): 3325-3336.
Ambati J. Ambati, B.K., Yoo, S.H., Ianchulev, S., and Adamis, A.P. (2003). Age-related macular degeneration: etiology, pathogenesis, and therapeutic strategies. Sury Ophthalmol 48, 257-293.
Barrat, F. J. and R. L. Coffman (2008). "Development of TLR inhibitors for the treatment of autoimmune diseases." Immunol Rev 223: 271-283.
Batzer, M.A., and Deininger, P.L. (2002). Alu repeats and human genomic diversity. Nat Rev Genet 3, 370-379.
Bauemfeind, F., Bartok, E., Rieger, A., Franchi, L., Nunez, G., and Hornung, V. (2011). Cutting edge: reactive oxygen species inhibitors block priming, but not activation, of the NLRP3 inflammasome. J Immunol 187, 613-617.
Bauemfeind, F. G. et al. Cutting edge: NF-kappaB activating pattern recognition and cytokine receptors license NLRP3 Inflammasome activation by regulating NLRP3 expression. J Immunol 183, 787-791 (2009).
Bennett, E.A., Keller, H., Mills, R.E., Schmidt, S., Moran, J.V., Weichenrieder, O., and Devine, S.E. (2008). Active Alu retrotransposons in the human genome. Genome Res 18, 1875-1883.
Bernstein, E., Gaudy, A.A., Hammond, S.M., and Hannon, G.J. (2001). Role for a bidentate ribonuclease in the nitiation step of RNA interference. Nature 409, 363-366.
Brichacek, B., C. Vanpouille, et al. (2010). "Contrasting roles for TLR ligands in HIV-1 pathogenesis." PLoS One 5(9).
Sao, Z., Henzel, W.J., and Gao, X. (1996). IRAK: a kinase associated with the interleukin-1 receptor. Science 271, 1128-1131.
Chen C. J., Y. Shi, et al. (2006). "MyD88-dependent IL-1 receptor signaling is essential for gouty inflammation stimulated by monosodium urate crystals." J Clin Invest 116(8): 2262-2271.
Dhellin, O., Maestre, J., and Heidmann, T. (1997). Functional differences between the human Line retrotransposon and retroviral reverse transcriptases for in vivo mRNA reverse transcription. EMBO J 16, 6590-6602.
Diebold, S.S., Kaisho, T., Hemmi, H., Akira, S., and Reis e Sousa, C. (2004). Innate antiviral responses by means of TLR7-mediated recognition of single-stranded RNA. Science 303, 1529-1531.
Feher, J., Kovacs, I., Artico, M., Cavallotti, C., Papale, A., and Balacco Gabrieli, C. (2006). Mitochondrial alterations of retinal pigment epithelium in age-related macular degeneration. Neurobiol Aging 27, 983-993.
Fernandes-Alnemri, T., Wu, J., Yu, J.W., Datta, P., Miller, B., Jankowski, W., Rosenberg, S., Zhang, J., and Alnemri, E.S. (2007). The pyroptosome: a supramolecular assembly of ASC dimers mediating inflammatory cell death via caspase-1 activation. Cell Death Differ 14, 1590-1604.
Ghayur, T., Banerjee, S., Hugunin, M., Butler, D., Herzog, L., Carter, A., Quintal, L., Sekut, L., Talanian, R., Paskind, M., et al. (1997). Caspase-1 processes IFN-gamma-inducing factor and regulates LPS-induced IFN-gamma production. Nature 386, 619-623.
Kumar, H., Kawai, T., Kato, H., Sato, S., Takahashi, K., Coban, C., Yamamoto, M., Uematsu, S., Ishii, K.J., Takeuchi, D., et al. (2006). Essential role of IPS-1 in innate immune responses against RNA viruses. J Exp Med 203, 1795-1803.
Gu, Y., Kuida, K., Tsutsui, H., Ku, G., Hsiao, K., Fleming, M.A., Hayashi, N., Higashino, K., Okamura, H., Nakanishi, K., et al. (1997). Activation of interferon-gamma inducing factor mediated by interleukin-1beta converting enzyme. Science 275, 206-209.
Guarda, G., Braun, M., Staehli, F., Tardivel, A., Mattmann, C., Forster, I., Farlik, M., Decker, T., Du Pasquier, R.A., Romero, P., et al. (2011). Type I interferon inhibits interleukin-1 production and inflammasome activation. Immunity 34, 213-223.
Guarda, G., Dostert, C., Staehli, F., Cabalzar, K., Castillo, R., Tardivel, A., Schneider, P., and Tschopp, J. (2009). T cells dampen innate immune responses through inhibition of NLRP1 and NLRP3 inflammasomes. Nature 460, 269-273.
Guo, H. J. Gao et al. (2011). "Toll-like receptor 2 siRNA suppresses corneal inflammation and attenuates Aspergillus fumigatus keratitis in rats." Immunol Cell Biol.
Halle, A., Hornung, V., Petzold, G.C., Stewart, C.R., Monks, B.G., Reinheckel, T., Fitzgerald, K.A., Latz, E., Moore, K. J., and Golenbock, D.T. (2008). The NALP3 inflammasome is involved in the innate immune response to amyloid-beta. Nat Immunol 9, 857-865.
Heil, F., Hemmi, H., Hochrein, H., Ampenberger, F., Kirschning, C., Akira, S., Lipford, G., Wagner, H., and Bauer, S. (2004). Species-specific recognition of single-stranded RNA via toll-like receptor 7 and 8. Science 303, 1526-1529.
Hibi, H., Chen, Y., Thirumalai, K. & Zychlinsky, A. The interleukin 1beta-converting enzyme, caspase 1, is activated during Shigella flexneri-induced apoptosis in human monocyte-derived macrophages. Infect Immun 65, 5165-5170 (1997).

(56) References Cited

OTHER PUBLICATIONS

Hoebe, K., Du, X., Georgel, P., Janssen, E., Tabeta, K., Kim, S.O., Goode, J., Lin, P., Mann, N., Mudd, S., et al. (2003). Identification of Lps2 as a key transducer of MyD88-independent TIR signalling. Nature 424, 743-748.

Hornung, V., Ellegast, J., Kim, S., Brzozka, K., Jung, A., Kato, H., Poeck, H., Akira, S., Conzelmann, K.K., Schlee, M., et al. (2006). 5'-Triphosphate RNA is the ligand for RIG-I. Science 314, 994-997.

Jenssens et al. Regulation of Interleukin-1- and Lipopolysaccharide-Induced NF-κB Activation by Alternative Splicing of MyD88. Current Biology 2002; 12:467-71.

Juliana, C. et al. Anti-inflammatory compounds parthenolide and Bay 11-7082 are direct inhibitors of the inflammasome. J Biol Chem 285, 9792-9802, doi:10.1074/jbc.M109.082305 (2010).

Kaneko, H., Dridi, S., Tarallo, V., Gelfand, B.D., Fowler, B.J., Cho, W.G., Kleinman, M.E., Ponicsan, S.L., Hauswirth, N.W., Chiodo, V.A., et al. (2011). DICER1 deficit induces Alu RNA toxicity in age-related macular degeneration. Nature 471, 325-330.

Kanneganti, T.D., Ozoren, N., Body-Malapel, M., Amer, A., Park, J.H., Franchi, L., Whitfield, J., Barchet, W., Colonna, M., Vandenabeele, P., et al. (2006). Bacterial RNA and small antiviral compounds activate caspase-1 through cryopyrin/Nalp3. Nature 440, 233-236.

Kato, H., Takeuchi, O., Sato, S., Yoneyama, M., Yamamoto, M., Matsui, K., Uematsu, S., Jung, A., Kawai, T., Ishii, K. J., et al. (2006). Differential roles of MDA5 and RIG-I helicases in the recognition of RNA viruses. Nature 441, 101-105.

Keller, M., Ruegg, A., Werner, S., and Beer, H.D. (2008). Active caspase-1 is a regulator of unconventional protein secretion. Cell 132, 818-831.

Kleinman, M.E, Kaneko, H., Cho, W.G., Dridi, S., Fowler, B.J., Blandford, A.D., Albuquerque, R.J., Hirano, Y., Terasaki, H., Kondo, M., et al. (2012). Short-interfering RNAs Induce Retinal Degeneration via TLR3 and IRF3. Mol Ther. 20, 101-108.

Kleinman, M.E., Yamada, K., Takeda, A., Chandrasekaran, V., Nozaki, M., Baffi, J.Z., Albuquerque, R.J., Yamasaki, S., Itaya, M., Pan, Y., et al. (2008). Sequence- and target-independent angiogenesis suppression by siRNA via TLR3. Nature 452, 591-597.

Komiyama, T. et al. Inhibition of interleukin-1 beta converting enzyme by the cowpox virus serpin CrmA. An example of cross-class inhibition. J Biol Chem 269, 19331-19337 (1994).

Krieg, A. M. et al. Sequence motifs in adenoviral DNA block immune activation by stimulatory CpG motifs. Proc Natl Acad Sci U S A 95, 12631-12636 (1998).

\* cited by examiner

Faslg-/- (Fasl$^{gld}$) mice

Faslg-/- (Fasl$^{gld}$) mice

SEQUENCE LISTING

```
<160> NUMBER OF SEQ ID NOS: 61

<210> SEQ ID NO 1
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 1

Asp Arg Gln Ile Lys Ile Trp Phe Gln Asn Arg Arg Met Lys Trp Lys
1               5                   10                  15

Lys Arg Asp Val Leu Pro Gly Thr
            20

<210> SEQ ID NO 2
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 2

Asp Arg Gln Ile Lys Ile Trp Phe Gln Asn Arg Arg Met Lys Trp Lys
1               5                   10                  15

Lys
```

-continued

```
<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 3
gagaagccuu uacaggutt                                                19

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 4
accuguaaag gcuucuctt                                                19

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 5
cagagcaagg aaugugatt                                                19

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 6
ucacauuccu ugcucugtt                                                19

<210> SEQ ID NO 7
<211> LENGTH: 19
<212> TYPE: DNA
<213> ORGANISM: Artificial Sequence
<220> FEATURE:
```

```
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 7 guugacuau cuguucutt                                                  19

<210> SEQ ID NO 8
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 8
ggaucaaacu acucuguga                                                 19

<210> SEQ ID NO 9
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 9
ugcaagaucu cucagcaaa                                                 19

<210> SEQ ID NO 10
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 10
gaaguggggu ucagauaau                                                 19

<210> SEQ ID NO 11
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 11
gcaagaccaa gacguguga                                                 19

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 12
gaagcucuuc aguuucatt                                                 19
```

```
<210> SEQ ID NO 13
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 13
ggcugcugga ugcucuguac gggaa                                           25

<210> SEQ ID NO 14
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 14
uucccguaca gagcauccag cagcc                                           25

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 15
gctggagcag gtgtactact tc                                              22

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
caggtttgac tatctgttct                                                 20

<210> SEQ ID NO 17
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 17
gtgaagagat ccttctgta                                                  19

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
ttaaagcccg cctgacaga                                                  19

<210> SEQ ID NO 19
<211> LENGTH: 23
<212> TYPE: DNA
<213> ORGANISM: Artificial Sequence
<220> FEATURE:
<223> OTHER INFORMATION: Synthetic oligonucleotide
```

```
<400> SEQUENCE: 19
gcgaatgaca gagggtttct tag                                              23

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
atcacttgca ctccggaggt a                                                21

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 21
agagcgcaat ggtgcaatc                                                   19

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 22
gcacctgttg tgcaatctga a                                                21

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 23
tcctgacaac atgctgatgt ga                                               22

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
gccaggcctg cactttatag a                                                21

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 25
gtttgtgacc ctcgcgataa g                                                21

<210> SEQ ID NO 26
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 26
actgcaaaat cccgagtgac                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
ctgtccaggc aagattgaca                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
cagtgccaaa tcaaagctga                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
cctgatgtcc aagcaaggtt                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
ttgacacagc caaatccaaa                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
gccaaaacgg gtgttgttac                                               20

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 32
```
cgcagctagg aataatggaa tagg                                          24

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
gcctcagttc cgaaaaccaa                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
cacctgtgtc tggtccattg                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
aggctgagtg caaacttggt                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
atgctgcttc gacatctcct                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
aaccaatgcg agatcctgac                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
gacagcctgt gttcgaggat                                               20

<210> SEQ ID NO 39
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 39
tggatccatt tcctcaaagg                                              20

<210> SEQ ID NO 40
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 40
ttcgtattgc gccgctaga                                               19

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
ctttcgctct ggtccgtctt                                              20

<210> SEQ ID NO 42
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 42
tggacggaga actgataagg gt                                           22

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
agctacatct ggctactggg t                                            21

<210> SEQ ID NO 44
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 44
aaaagctggg ttgagagggc ga                                           22

<210> SEQ ID NO 45
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 45
tcaggctcag tccctcccg at                                            22
```

```
<210> SEQ ID NO 46
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 46
aaattcgtga agcgttcc                                                 18

<210> SEQ ID NO 47
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 47
cggaauagca gccaagutt                                                19

<210> SEQ ID NO 48
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 48
cccuggaguu ggaggcutt                                                19

<210> SEQ ID NO 49
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 49
cccuggaguu ggaggcutt                                                19

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
gcugaccttt ttgctucuca                                               20
```

<210> SEQ ID NO 51
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 51
ttggtacgca tacgtgttga ctgtga                                  26

<210> SEQ ID NO 52
<211> LENGTH: 91
<212> TYPE: DNA
<213> ORGANISM: Artificial Sequence
<220> FEATURE:
<223> OTHER INFORMATION: Synthetic oligonucleotide

<400> SEQUENCE: 52 cccggttca cgccattctc ctgcctcagc ctcacgagta gctgggacta caggcgcccg   60
acaccactcc cggctaattt tttgtatttt t                              91

<210> SEQ ID NO 53
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 53
gcatggccag tccattgatc ttgcacgctt gcctagtacg ctcctcaacc tatcctccta   60
gcccgttact tggtgccacc ggcg                                      84

<210> SEQ ID NO 54
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 54

Arg Asp Val Leu Pro Gly Thr
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 55

Arg Asp Val Val Pro Gly Gly
1               5

<210> SEQ ID NO 56
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

```
<400> SEQUENCE: 56
uauuuccuaa uuggguctt                                                19

<210> SEQ ID NO 57
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 57
cggaauagca gccaagutt                                                19

<210> SEQ ID NO 58
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 58
cccuggaguu ggaggcutt                                                19

<210> SEQ ID NO 59
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: dT
<222> LOCATION: (18)..(18)
<220> FEATURE:
<221> NAME/KEY: dT
<222> LOCATION: (19)..(19)

<400> SEQUENCE: 59
gcuuuaaucg augggaatt                                                19

<210> SEQ ID NO 60
<211> LENGTH: 32
<212> TYPE: PRT
<213> ORGANISM: Artificial Sequence
<220> FEATURE:
<223> OTHER INFORMATION: synthesized polypeptide

<400> SEQUENCE: 60

Asp Arg Gln Ile Lys Ile Trp Phe Gln Asn Arg Arg Met Lys Trp Lys
1               5                   10                  15

Lys Arg Asp Val Leu Pro Gly Thr Cys Val Trp Ser Ile Ala Ser Glu
            20                  25                  30
```

```
<210> SEQ ID NO 61
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 61

Arg Asp Val Leu Pro Gly Thr Cys Val Trp Ser Ile Ala Ser Glu
1               5                   10                  15
```

US 9,453,226 B2

PROTECTION OF CELLS FROM ALU-RNA-INDUCED DEGENERATION AND INHIBITORS FOR PROTECTING CELLS

RELATED APPLICATIONS

This application claims priority from International Patent Application No. PCT/US2012/046928 filed Jul. 16, 2012, which claims priority to U.S. Provisional Application Ser. No. 61/508,867 filed Jul. 18, 2011 and U.S. Provisional Application Ser. No. 61/543,038 filed Oct. 4, 2011, the entire disclosures of each of which are incorporated herein by this reference.

GOVERNMENT INTEREST

This invention was made with government support under R01EY018350, R01EY018836, R01EY020672, R01EY022238, R21EY019778, RC1EY020442 awarded by the National Eye Institute of the National Institutes of Health. The government has certain rights in the invention.

TECHNICAL FIELD

The presently-disclosed subject matter relates to inhibition of inflammosome, MyD88, IL-18, VDAC1, VDAC2, Caspase-8, and NFκB; inhibitors of inflammosome, MyD88, IL-18, VDAC1, VDAC2, Caspase-8, and NFκB, methods protecting a cell, and screening methods for identifying inhibitors.

INTRODUCTION

Age-related macular degeneration (AMD), which is as prevalent as cancer in industrialized countries, is a leading cause of blindness worldwide. In contrast to the neovascular form of AMD, for which many approved treatments exist, the far more common atrophic form of AMD remains poorly understood and without effective clinical intervention. Extensive atrophy of the retinal pigment epithelium (RPE) leads to severe vision loss and is termed geographic atrophy, the pathogenesis of which is unclear. Geographic atrophy causes blindness in millions of people worldwide and there is currently no approved treatment.

The present inventors have shown a dramatic reduction of the RNase DICER1 in the retinal pigmented epithelium (RPE) of human eyes with geographic atrophy (Kaneko et al. Nature 2011, which is incorporated herein by this reference). The present inventors have also demonstrated that DICER1 deficiency leads to an accumulation of Alu RNA transcripts, which is also observed in the RPE of human eyes with geographic atrophy. These Alu RNA transcripts induce cell death of human RPE cells and RPE degeneration in mice. The precise mechanisms of cytotoxicity of Alu transcripts are unknown.

As described herein the present inventors have now found that DICER1 deficit or Alu RNA exposure activates the NLRP3 inflammasome and triggers toll-like receptor-independent MyD88 signalling via IL-18 both in the RPE of mice and in human and mouse RPE cells.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods for identifying MyD88 inhibitors, and methods and compositions for inhibiting MyD88 and uses thereof. The presently-disclosed subject matter includes methods for identifying inflammasome inhibitors, and methods and compositions for inhibiting an inflammasome and uses thereof. The presently-disclosed subject matter includes methods for identifying inhibitors of components of inflammasome, and methods and compositions for inhibiting a component of inflammasome and uses thereof. Components of inflammasome include, for example, NLRP3, PYCARD, and Caspase-1. The presently-disclosed subject matter includes methods for identifying IL-18 inhibitors, and methods and compositions for inhibiting IL-18 and uses thereof. The presently-disclosed subject matter includes methods for identifying VDAC1 and VDAC2 inhibitors, and methods and compositions for inhibiting VDAC1 and VDAC2 and uses thereof. The presently-disclosed subject matter includes methods for identifying caspase-8 inhibitors, and methods and compositions for inhibiting caspase-8 and uses thereof. The presently-disclosed subject matter includes methods for identifying NFkB inhibitors, and methods and compositions for inhibiting NFkB and uses thereof. Also provided are methods and compositions for imaging activated caspase-1 in an eye of a subject.

The presently-disclosed subject matter includes methods including inhibiting one or more of an inflammasome, MyD88, and IL-18 of a cell. In some embodiments, the presently-disclosed subject matter includes methods including inhibiting one or more of MyD88, IL-18, VDAC1, VDAC2, NFκB, caspase-8, caspase-1, NLRP-3, PYCARD, and an inflammasome, including a component of an inflammasome (e.g., caspase 1, NLRP-3, PYCARD) of a cell. In some embodiments, the presently-disclosed subject matter includes methods including administering one or more inhibitors selected from inhibitors of MyD88, IL-18, VDAC1, VDAC2, NFκB, caspase-8, caspase-1, NLRP-3, PYCARD, and an inflammasome, including a component of an inflammasome (e.g., caspase 1, NLRP-3, PYCARD).

In some embodiments of the method, the cell is selected from an RPE cell, a retinal photoreceptor cell, or a choroidal cell. In some embodiments, the cell is an RPE cell. In some embodiments, the cell is the cell of a subject. In some embodiments, the cell is a cell of a subject having, suspected of having, or at risk of having a condition of interest. In some embodiments, the cell is a cell of a subject having, suspected of having, or at risk of having age-related macular degeneration. In some embodiments, the cell is a cell of a subject having, suspected of having, or at risk of having geographic atrophy. In some embodiments, the cell is a cell of a subject having, suspected of having, or at risk of having geographic atrophy and the cell is an RPE cell. In some embodiments, a subject having age-related macular degeneration can be treated using methods and compositions as disclosed herein.

In some embodiments of the method the cell is protected against Alu-RNA-induced degeneration.

No significant difference in miRNA abundance between MyD88 inhibitor and control peptide-treated Dicer1 depleted cells. n=3 (A,B,F-H). Densitometry values normalized to Vinculin are shown in parentheses (A,C). Degeneration outlined by blue arrowheads. n=8 (E,F). *p<0.05 by Student t-test (G,I). Images representative of 3 experiments (A,B,C,D,H). See also FIG. 12.

Figure 7:
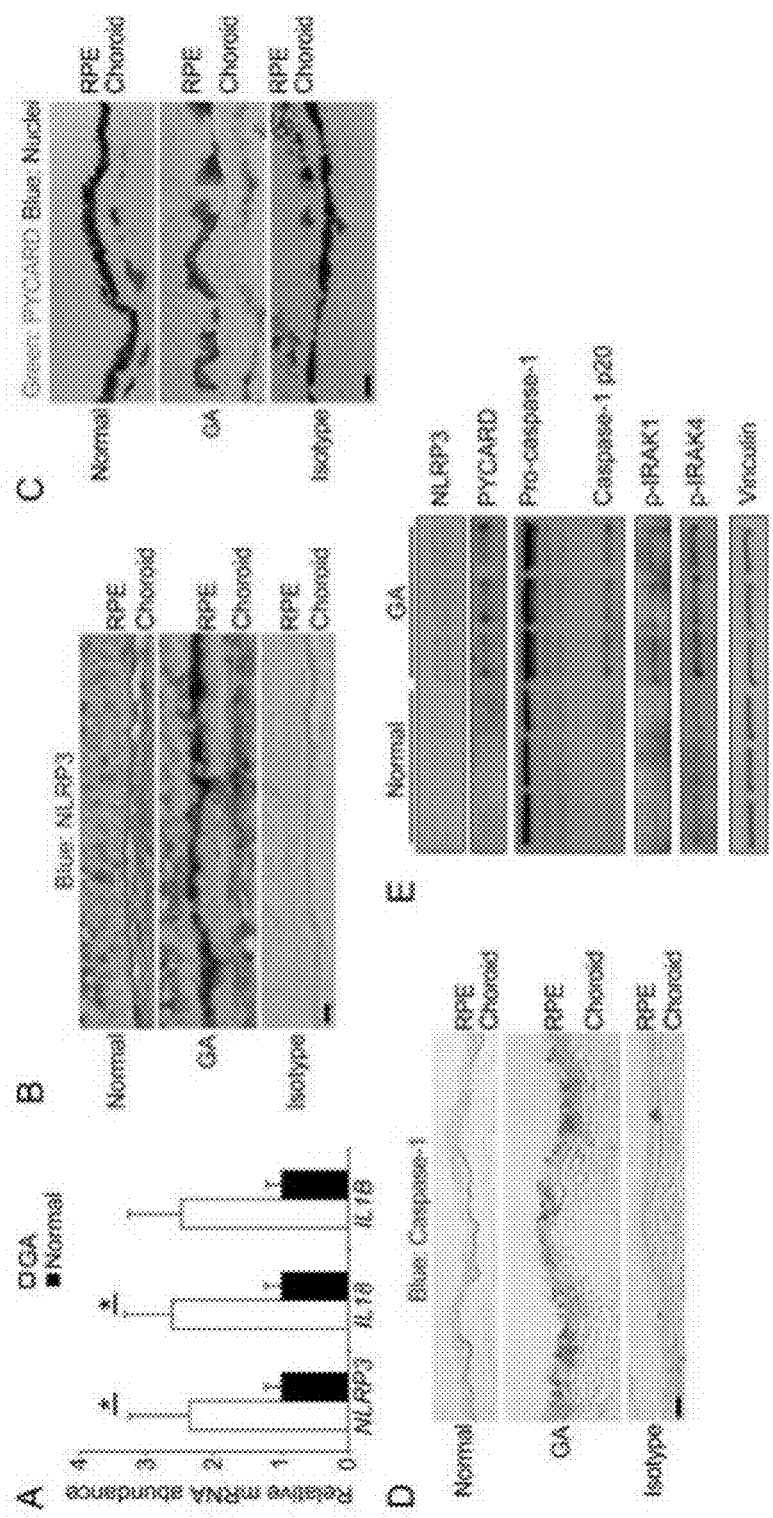

FIG. 7. NLRP3 Inflammasome and MyD88 activation in human GA (A) NLRP3 and IL18 abundance was significantly elevated in macular GA RPE (n=13) compared to normal age-matched controls (n=12). *p<0.05 by Mann-Whitney U-test. There was no significant difference between groups (p=0.32 by Mann-Whitney U-test) in IL1B abundance. (B-D) Increased immunolocalization of NLRP3 (B), PYCARD (C) and Caspase-1 (D) in macular GA RPE compared to age-matched normal controls. Scale bar, 20 µm. (E) Western blots of macular RPE lysates from individual human donor eyes show that abundance of NLRP3, PYCARD, and phosphorylated IRAK1/4, normalized to the levels of the housekeeping protein Vinculin, is reduced in geographic atrophy (GA) compared to age-matched normal controls. Data are represented as mean+/−SEM (A). Representative images shown. n=6 (B-E). See also FIG. 13.

Figure 8:
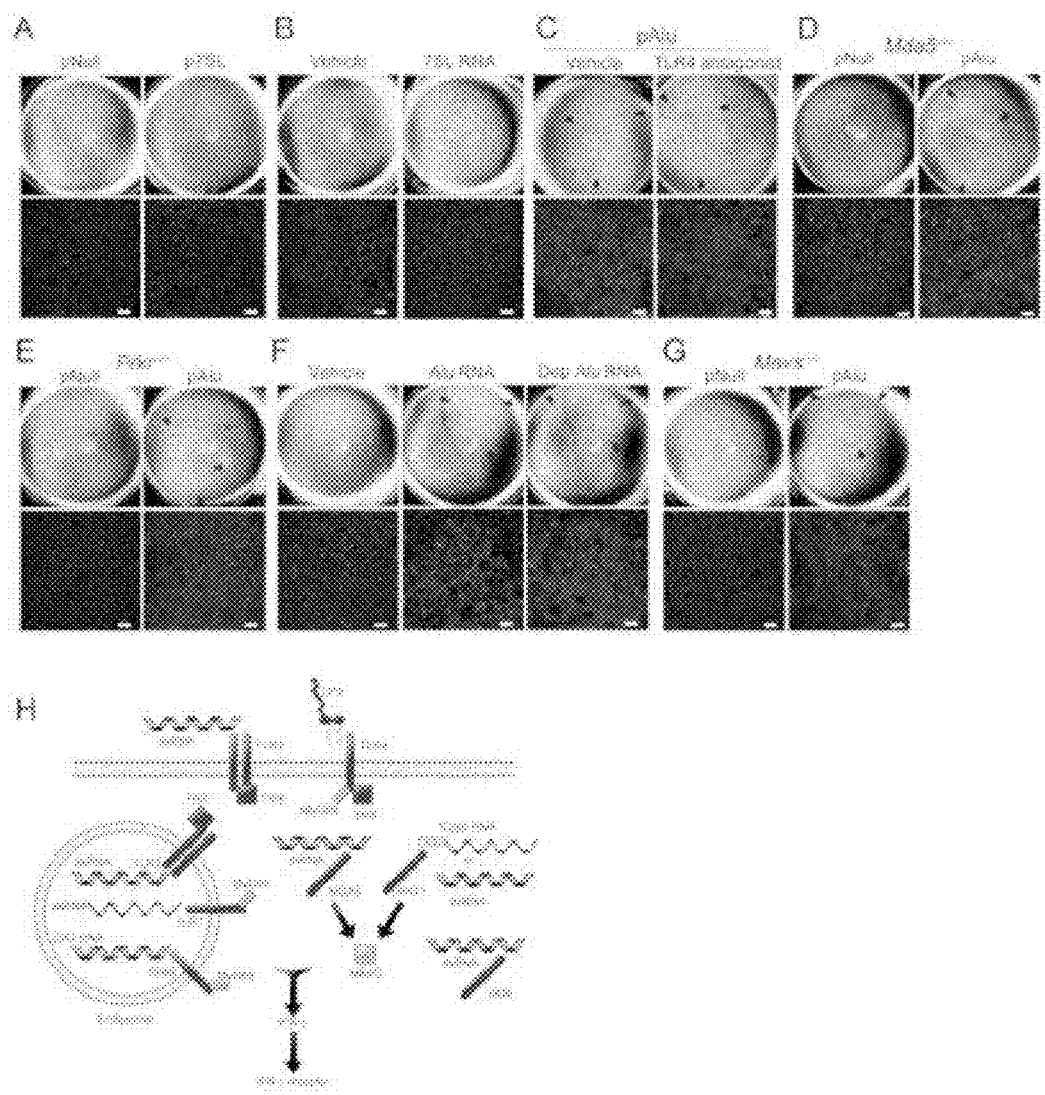

FIG. 8. Alu RNA does not activate several RNA sensors. (A and B) p7SL (a 7SL expression vector) (A) and in vitro synthesized 7SL RNA (B) do not induce RPE degeneration in wild-type mice. (C) RPE degeneration induced by subretinal injection of pAlu in wild-type mice is not blocked by a TLR4 antagonist. (D-E) Mice deficient in Mda5 (D) or Prkr (E) are susceptible to pAlu-induced RPE degeneration. (F) Dephosphorylated (Dep) Alu RNA induces RPE degeneration in wild-type mice just as well as Alu RNA. (G) Mice deficient in Mavs are susceptible to pAlu-induced RPE degeneration. pNull does not induce RPE degeneration in any strain of mice. Degeneration outlined by blue arrowheads. Fundus photographs, top rows; ZO-1 stained (red) RPE flat mounts, bottom rows. n=8 (A-G). (H) A schematic of the innate immune pathways that are not activated by Alu RNA.

Figure 9:
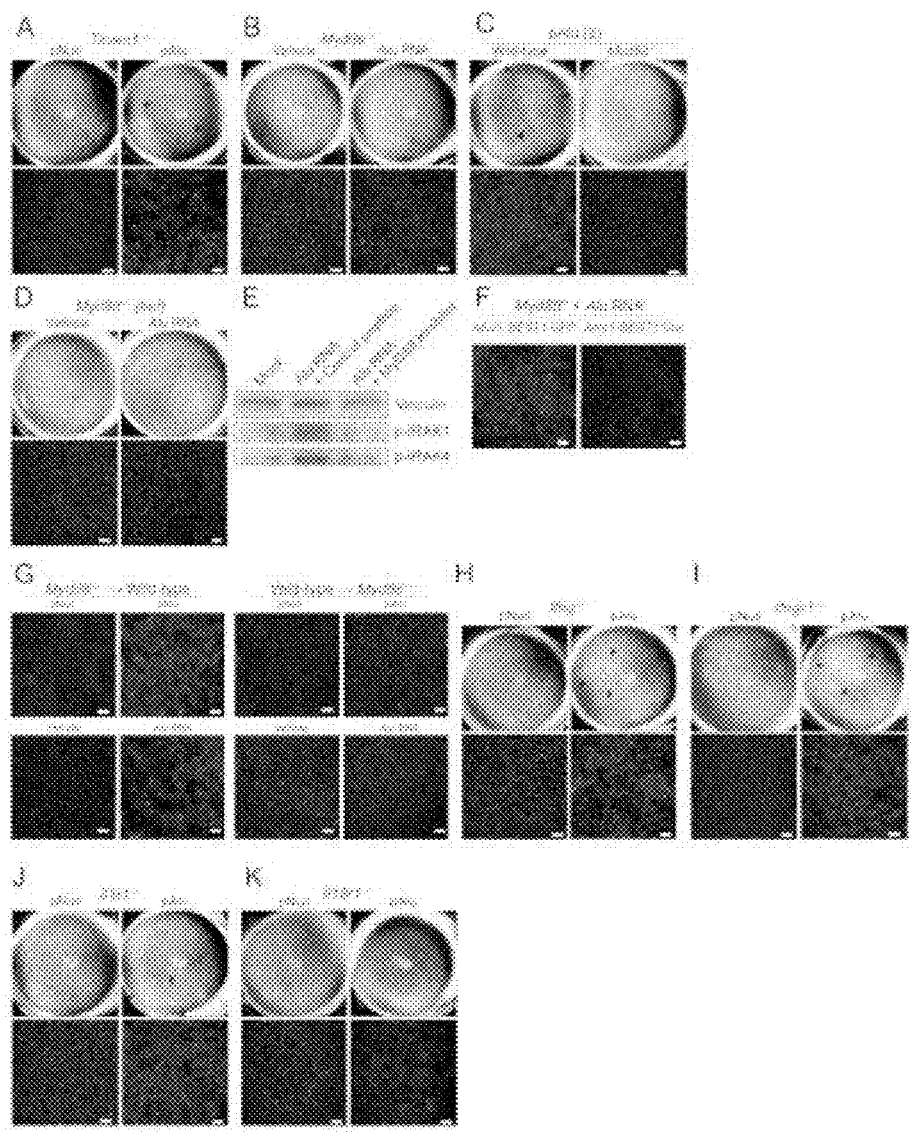

FIG. 9. Alu RNA induces RPE degeneration via MyD88, not TRIF or IFNγ, (A) Subretinal administration of pAlu induces RPE degeneration in Ticam1$^{-/-}$ mice. (B) Alu RNA does not induce RPE degeneration in Myd88$^{-/-}$ mice. (C) Subretinal administration of a different Alu expression plasmid (pAlu(2)) also induces RPE degeneration in wild-type but not Myd88$^{-/-}$ mice. (D) Alu RNA does not induce RPE degeneration in Myd88$^{+/-}$ heterozygous (het) mice. (E) MyD88 inhibitory peptide reduces Alu RNA-induced phosphorylation of IRAK1/4, normalized to Vinculin expression. (F) Subretinal injection of AAV1-BEST1-Cre, but not AAV1-BEST1-GFP, protects Myd88$^{f/f}$ mice from Alu RNA-induced RPE degeneration. (G) pAlu and Alu RNA induces RPE degeneration in wild-type mice receiving Myd88$^{-/-}$ bone marrow (Myd88$^{-/-}$→wild-type) but did not do so in Myd88$^{-/-}$ mice receiving wild-type bone marrow (wild-type→Myd88$^{-/-}$). (H-K) Subretinal administration of pAlu induces RPE degeneration in Ifng$^{-/-}$ (H), Ifngr1$^{-/-}$ (I), and Il1r1$^{-/-}$ mice (J) but not in Il18r1$^{-/-}$ mice (K). pNull administration does not induce RPE degeneration in any strain of mice. Degeneration outlined by blue arrowheads. Fundus photographs, top rows; ZO-1 stained (red) RPE flat mounts, bottom rows. n=8 (A-D, F-K).

Figure 10:
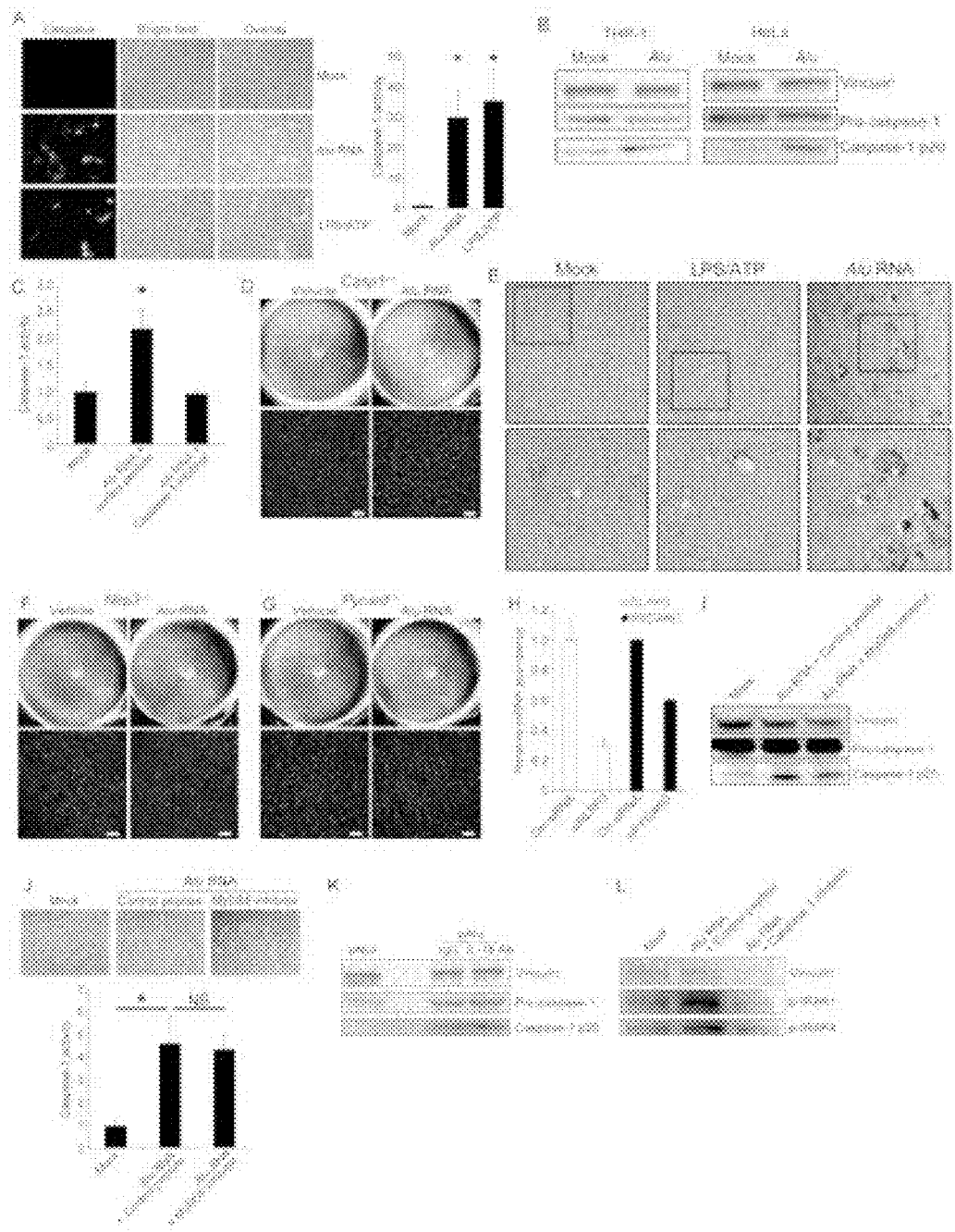

FIG. 10. Alu RNA induces RPE degeneration via NLRP3 inflammasome activation, (A) Alu RNA or LPS+ATP induce activation of Caspase-1 in human RPE cells as assessed by increased cleavage of Caspalux®1 (green, left panel), a fluorescent-linked peptide substrate as compared to mock treatment. Fluorescence quantification shown in right panel. (B) Western blot of Alu RNA-induced Caspase-1 activation (p20 subunit) in THP-1 and HeLa cells, normalized to Vinculin expression. (C) Caspase-1 inhibitor peptide blocks Alu RNA-induced substrate cleavage in human RPE cells. n=3. (D) Subretinal injection of Alu RNA does not induce RPE degeneration in Casp1$^{-/-}$ mice. (E) Alu RNA or LPS+ATP induce the appearance of a brightly fluorescent cluster of GFP-PYCARD visible in the cytoplasm of human RPE cells. Area in insets shown in higher magnification. Images representative of 3 experiments. (F and G) Subretinal injection of Alu RNA does not induce RPE degeneration in Nlrp3$^{-/-}$ (F) or Pycard$^{-/-}$ (G) mice. (H) The abundance of NLRP3 in HEK293 cells transfected with an NLRP3 expression vector and of PYCARD in human RPE cells is reduced by transfection of siRNAs targeting these genes, compared to control (Ctrl) siRNAs. n=3, *p<0.05 compared to Ctrl siRNAs by Student t-test. (I) Alu RNA-induced Caspase-1 activation (p20 subunit) in human RPE cells is unaffected by MyD88 inhibitory peptide, normalized to Vinculin expression. (J) MyD88 inhibitory peptide does not reduce Alu RNA-induced cleavage activity of Caspase-1 in human RPE cells (top panel). Fluorescence quantification (bottom panel). (K) Caspase-1 activation (p20 subunit) in RPE cell lysates of wild-type mice treated with subretinal pAlu administration is unimpaired by intravitreous administration of anti-IL-18 neutralizing antibodies. (L) Alu RNA-induced phosphorylation of IRAK1/4 is reduced by Caspase-1 inhibitory peptide in human RPE cells, normalized to Vinculin expression. Vehicle control injections also do not damage the RPE. Fundus photographs, top rows; ZO-1 stained (red) RPE flat mounts, bottom rows. n=8 (D,F,G). Images representative of 3 experiments (A,B,I,J-L).

Figure 11:
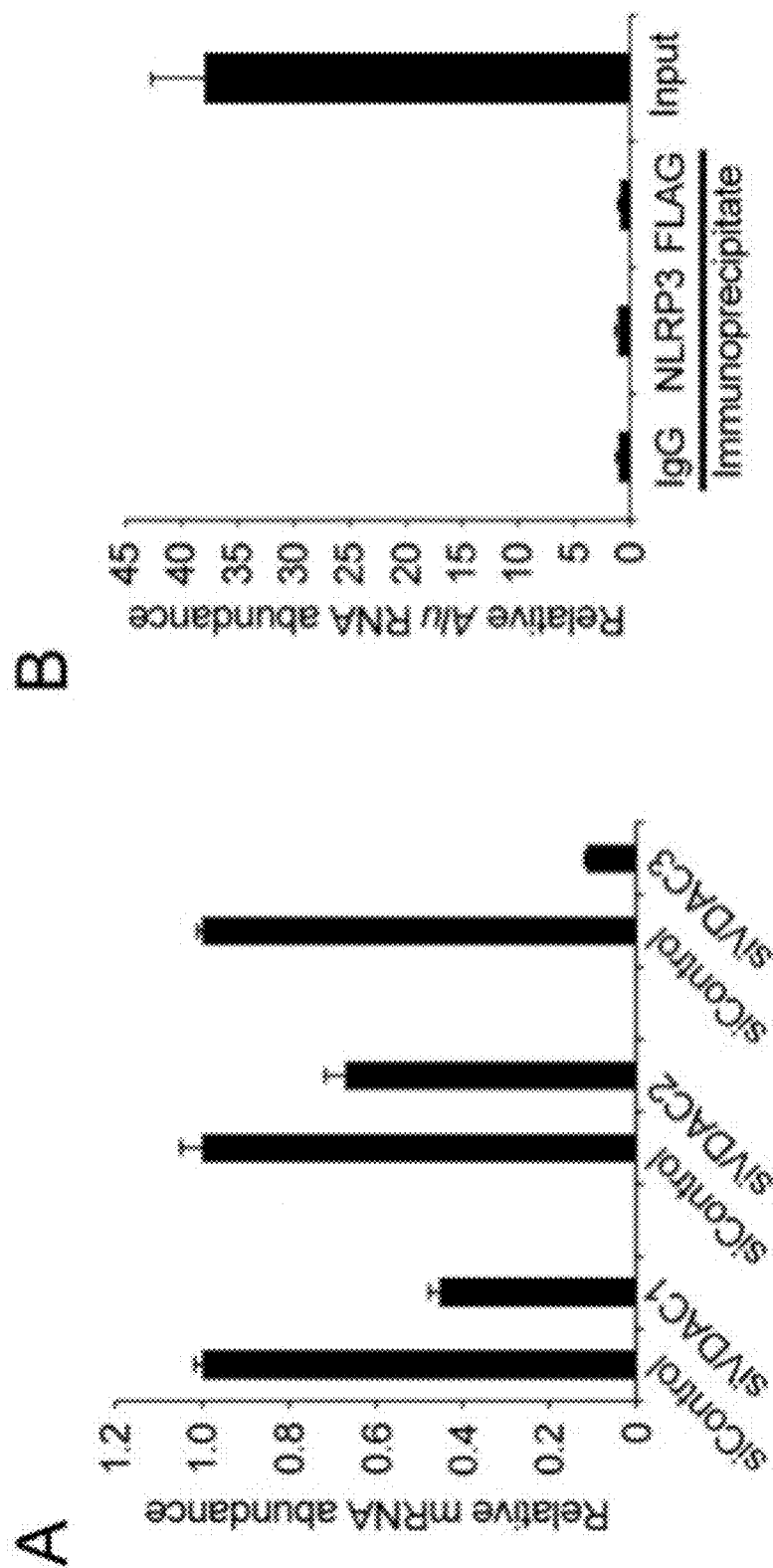

FIG. 11. NLRP3 does not physically interact with Alu RNA, and VDAC knockdown by siRNA. (A) RNA-binding protein immunoprecipitation (RIP) assay in human RPE cells transfected with pAlu and pNLRP3-FLAG Immunoprecipitation of protein-RNA complexes with antibodies against NLRP3 or FLAG did not reveal interaction between NLRP3 and Alu RNA. RNA isolated from an equal amount of cell lysate (not subjected to IP) was used as input for Alu PCR. Relative abundance of Alu RNA in the immunoprecipitate, assessed by real-time RT-PCR using Alu-specific primers, was normalized to levels obtained with control IgG immunoprecipitation. N=3. (B) The abundance of VDAC1, VDAC2, and VDAC3 mRNAs in human RPE cells is reduced by transfection of siRNAs targeting these genes compared to control (targeting Luc) siRNA. N=3. *p<0.05 compared to Control siRNA by Student t-test.

Figure 12:
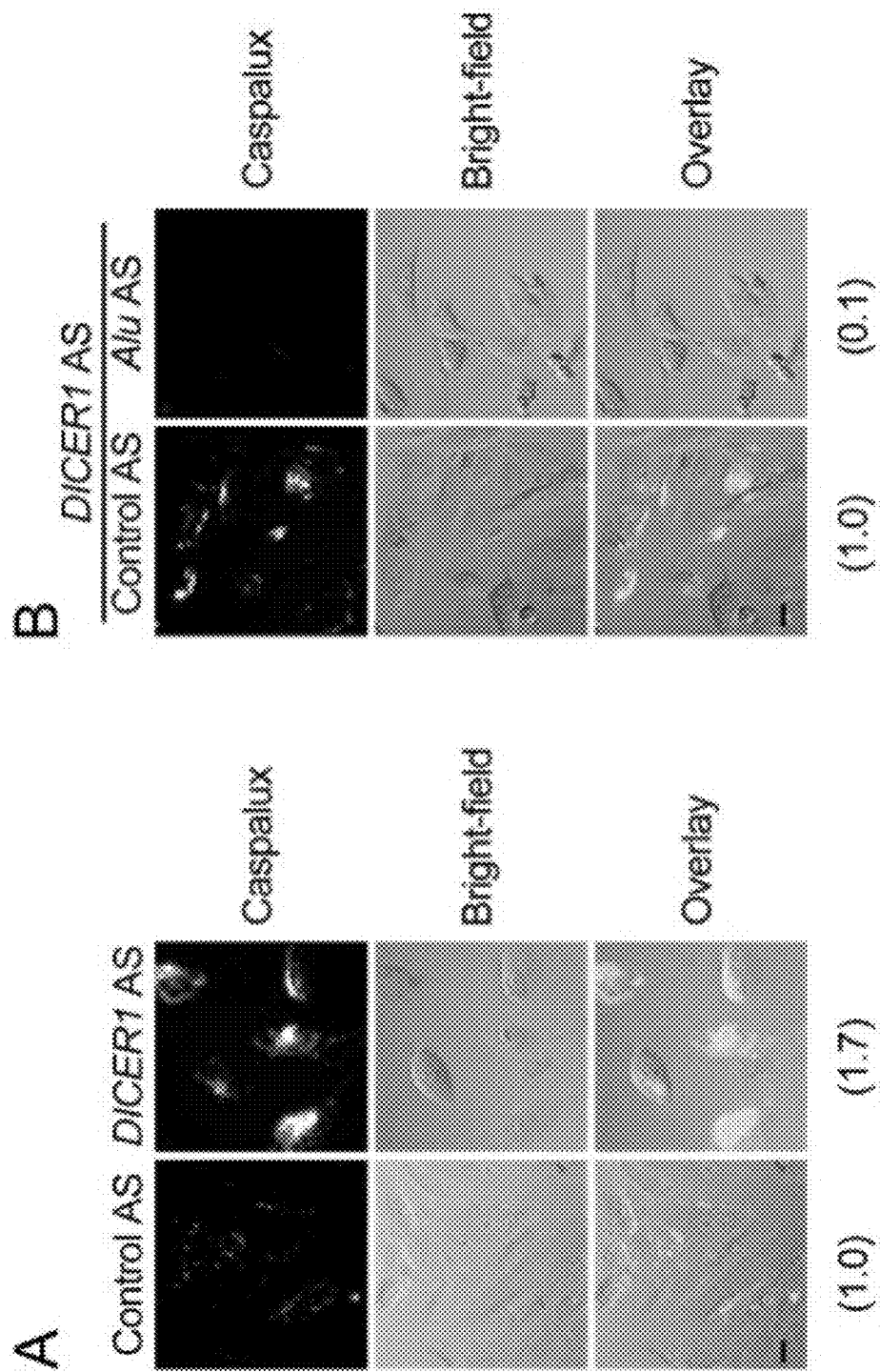

FIG. 12. DICER1 is a negative regulator of Caspase-1 activation by Alu RNA, (A) Knockdown of DICER1 by antisense oligonucleotides (AS) in human RPE cells increases cleavage activity of Caspase-1, as monitored by Caspalux, a fluorescent (green in overlay) reporter of substrate cleavage compared to control AS treatment. (B) Inhibition of Alu RNA by AS treatment reduces Caspalux fluorescence in human RPE cells treated with DICER1 AS. Mean values of Caspalux fluorescence shown in parentheses. Images representative of 3 experiments.

Figure 13:
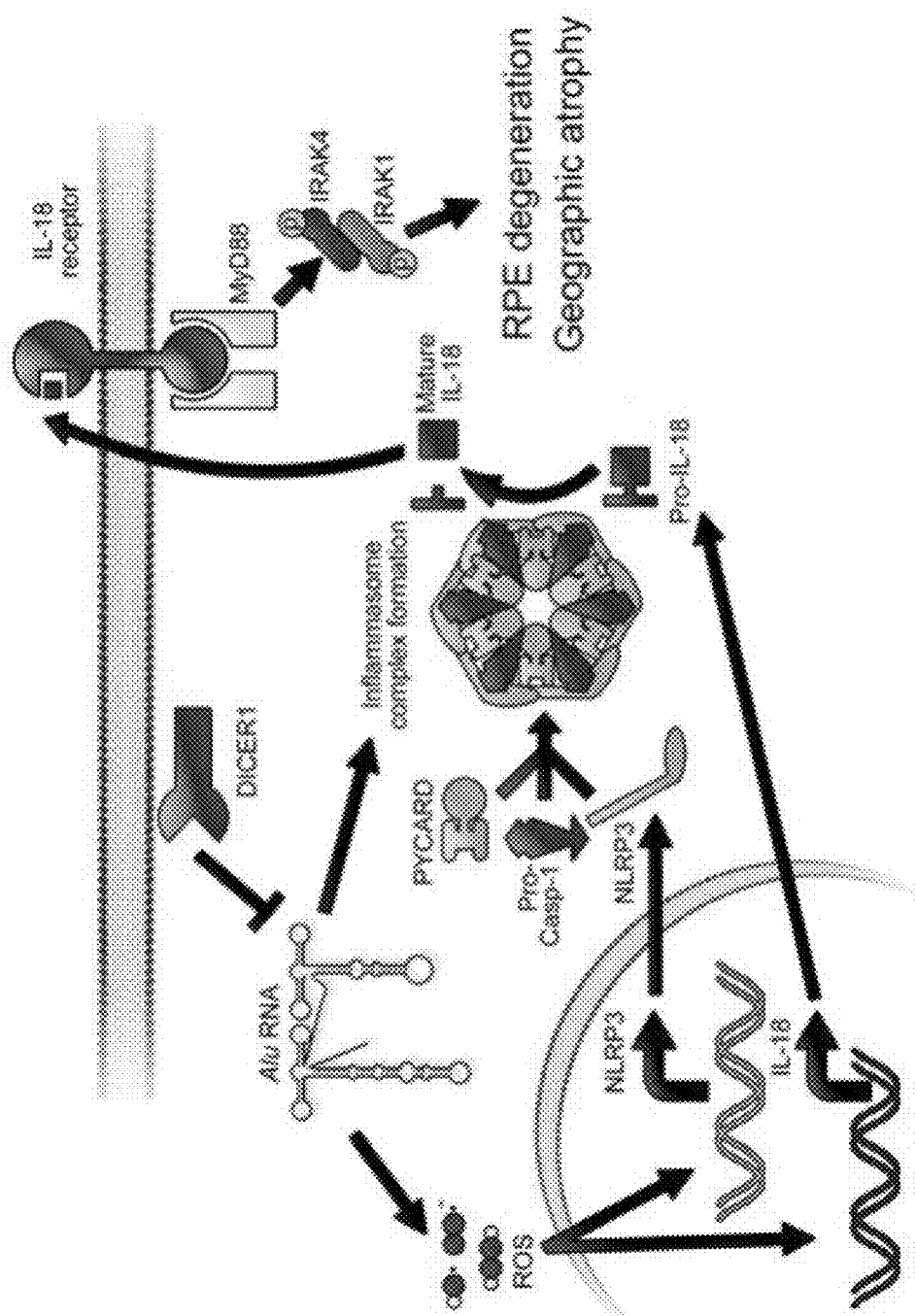

FIG. 13. Schematic representation of proposed model of NLRP3 inflammasome activation by DICER1 deficit-induced Alu RNA that leads to RPE degeneration and geographic atrophy. Alu RNA induces priming of NLRP3 and IL18 mRNAs via generation of reactive oxygen species (ROS). Activation of the NLRP3 inflammasome triggers cleavage of pro-IL-18 by activated Caspase-1 to mature IL-18. IL-18 signals via MyD88 to phosphorylate IRAK1 and IRAK4, which leads to RPE cell death.

Figure 14:
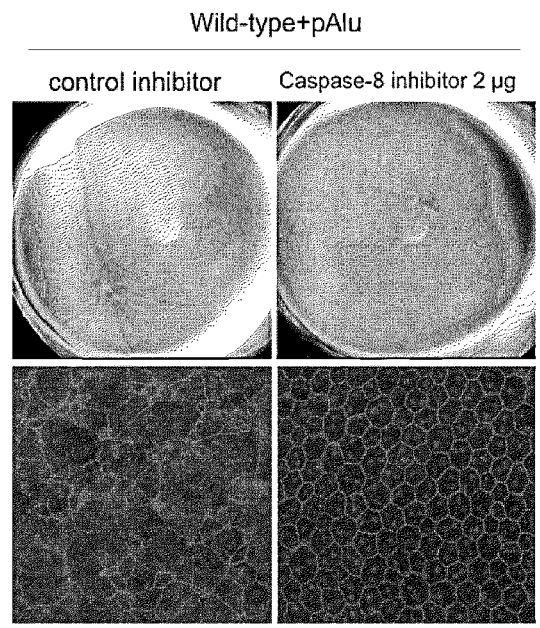

FIG. 14. Intravitreous administration of Caspase-8 inhibitor protects wild-type mice from pAlu-induced RPE degeneration. Representative images shown. n=8-12. Fundus photographs, top row; ZO-1 stained (red) flat mounts, bottom row.

Figure 15:
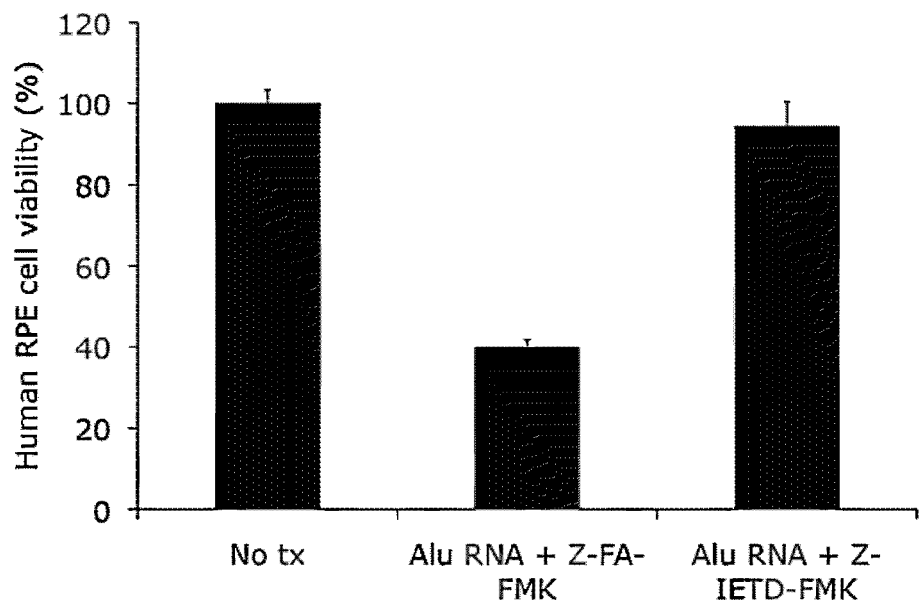

FIG. 15. Caspase-8 inhibitor protects human RPE cells from Alu induced cytotoxicity. Caspase-8 inhibitory peptide Z-IETD-FMK (100 µM) but not the control peptide Z-FA-FMK (100 µM) protects human RPE cells from Alu RNA-induced cytotoxicity.

Figure 16:
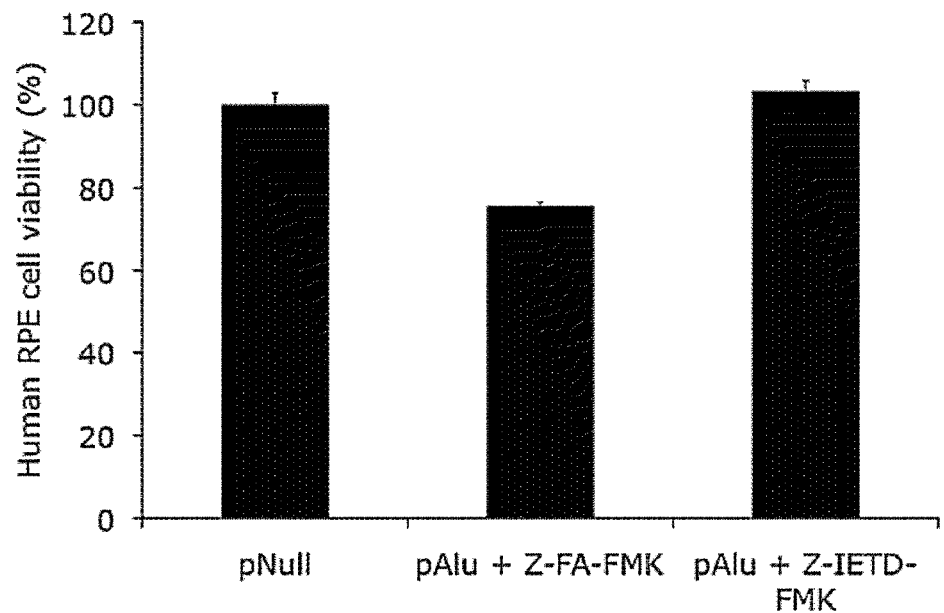

FIG. 16. Caspase-8 inhibitor protects human RPE cells from pAlu-induced cytotoxicity. Caspase-8 inhibitory peptide Z-IETD-FMK (100 µM) but not the control peptide Z-FA-FMK (100 µM) protects human RPE cells from pAlu-induced cytotoxicity.

Figure 17:
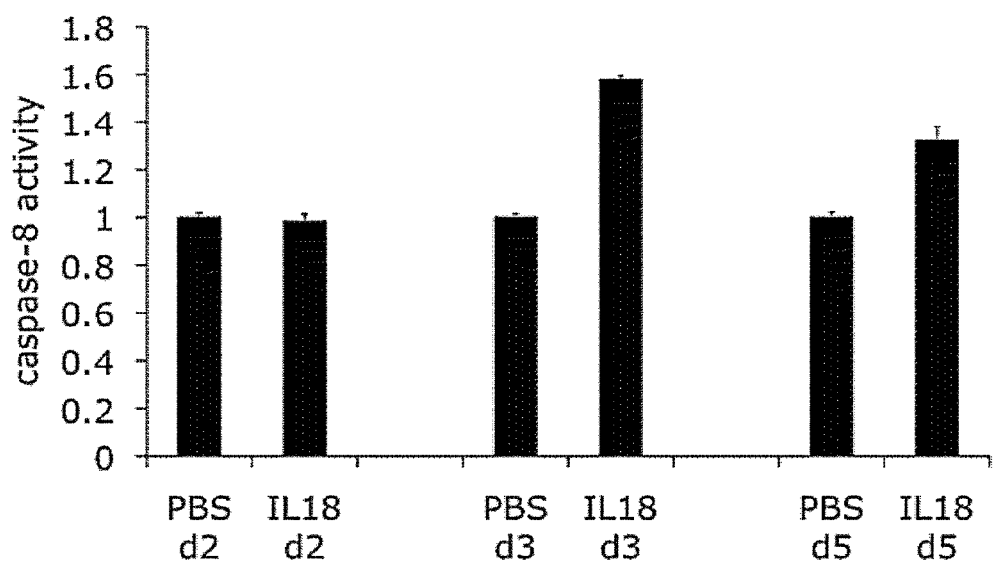

FIG. 17. IL-18 induced caspase-8 activation. Subretinal injection of IL-18 in wild-type mice induced activation of caspase-8, as monitored by fluorometric plate assay.

Figure 18:
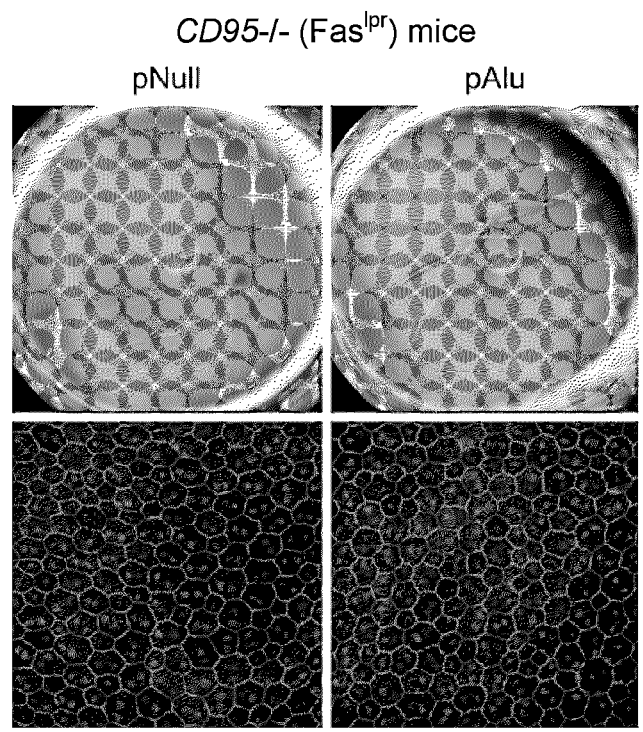

FIG. 18. pAlu does not induce RPE degeneration in CD95−/− mice. Representative images shown. n=8-12. Fundus photographs, top row; ZO-1 stained (red) flat mounts, bottom row.

Figure 19:
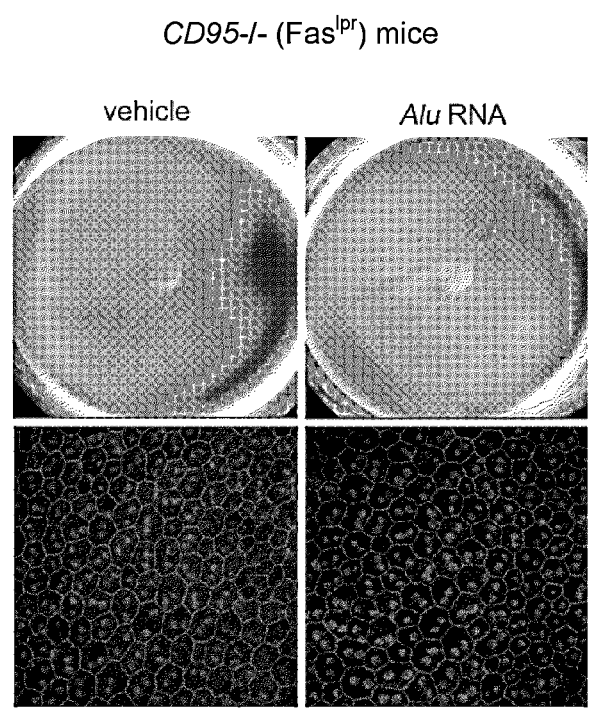

FIG. 19. Alu RNA does not induce RPE degeneration in CD95−/− mice. Representative images shown. n=8-12. Fundus photographs, top row; ZO-1 stained (red) flat mounts, bottom row.

Figure 20:
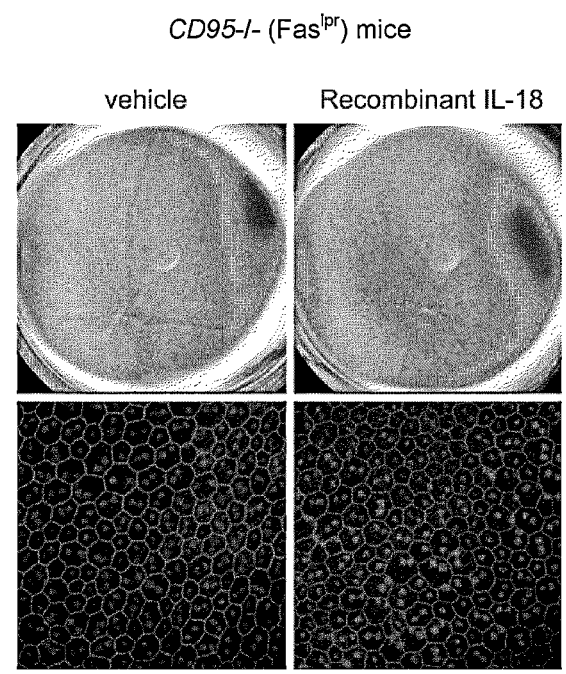

FIG. 20. Recombinant IL-18 does not induce RPE degeneration in CD95−/− mice. Representative images shown. n=8-12. Fundus photographs, top row; ZO-1 stained (red) flat mounts, bottom row.

Figure 21:
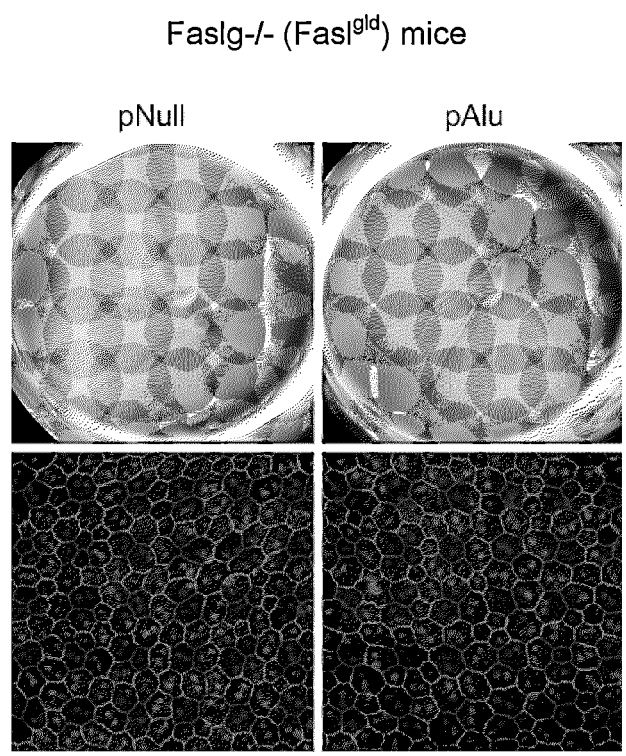

FIG. 21. pAlu does not induce RPE degeneration in Faslg mice. Representative images shown. n=8-12. Fundus photographs, top row; ZO-1 stained (red) flat mounts, bottom row.

Figure 22:
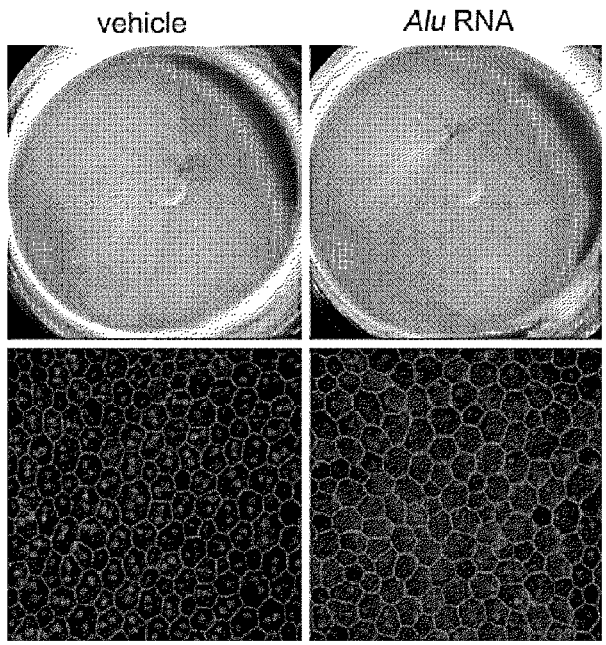

FIG. 22. Alu RNA does not induce RPE degeneration in Faslg mice. Representative images shown. n=8-12. Fundus photographs, top row; ZO-1 stained (red) flat mounts, bottom row.

Figure 23:
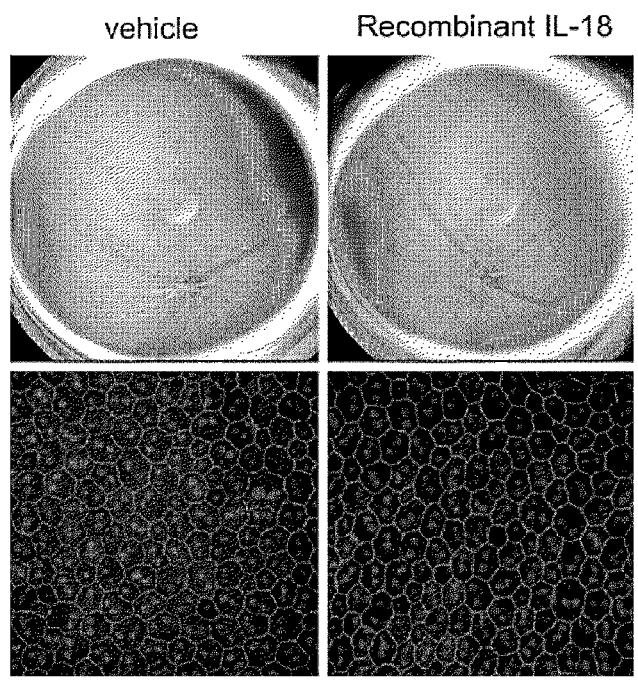

FIG. 23. Recombinant IL-18 does not induce RPE degeneration in Faslg mice. Representative images shown. n=8-12. Fundus photographs, top row; ZO-1 stained (red) flat mounts, bottom row.

Figure 24:
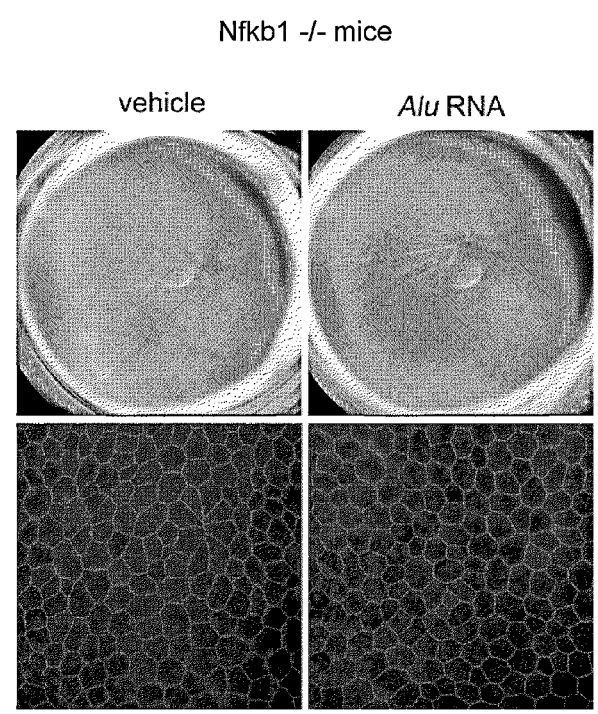

FIG. 24. Alu RNA does not induce RPE degeneration in Nfkb1−/− mice. Representative images shown. n=8-12. Fundus photographs, top row; ZO-1 stained (red) flat mounts, bottom row.

Figure 25:
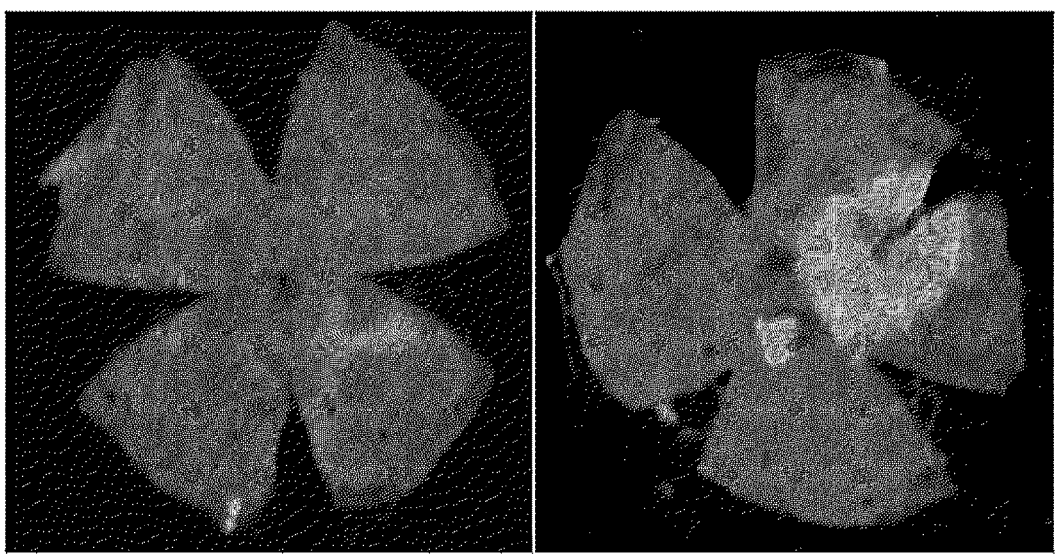

FIG. 25. Alu RNA or vehicle (PBS) was injected into the subretinal space of fellow eyes of a wild-type mouse. 3-days later, DyeLight782-VAD-FMK3 was injected into the vitreous humor of both eyes. 24-hours later, RPE flat mount preparations were visualized under fluorescent microscopy to visualize areas of bioactive caspase (green fluorescence), which corresponded to the area of Alu RNA injection.

Figure 26:
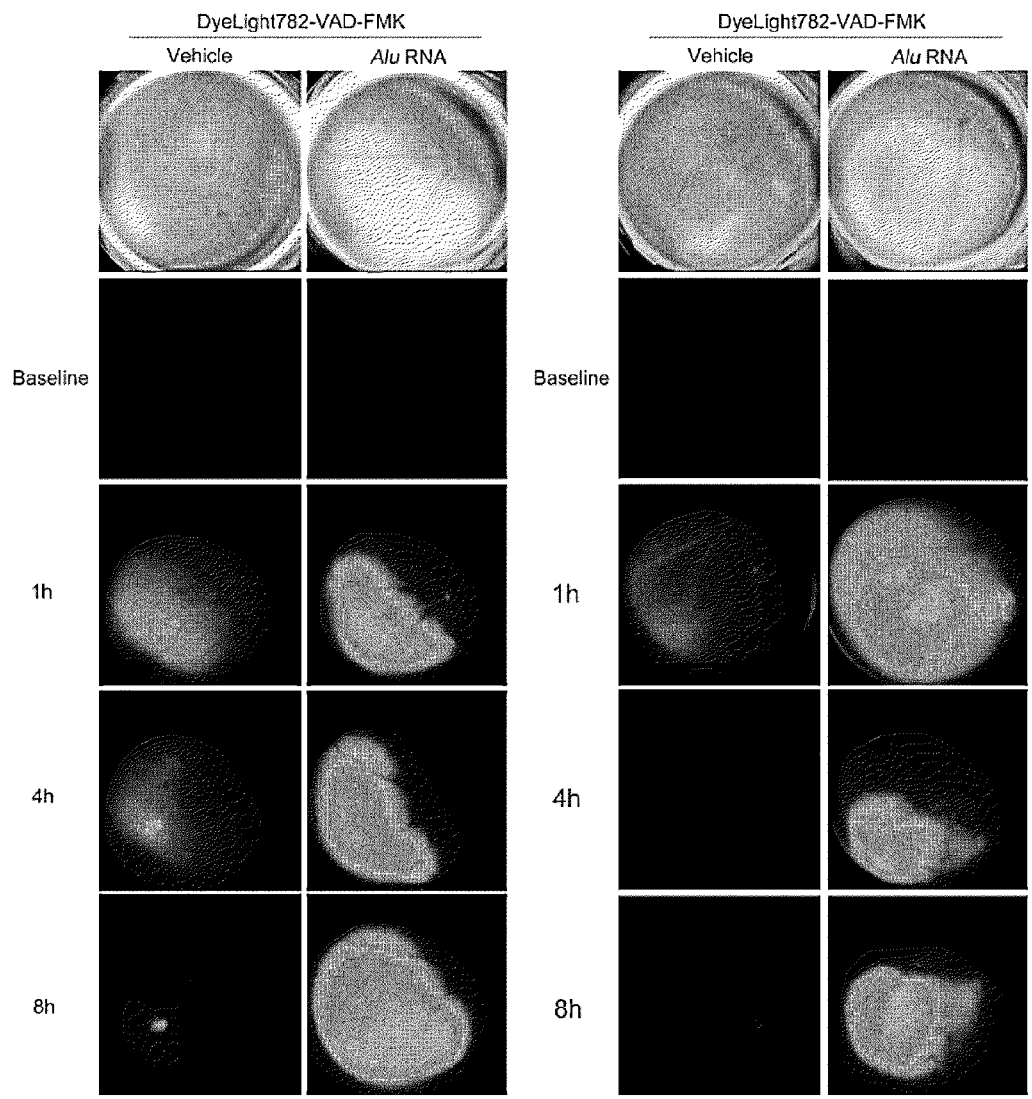

FIG. 26. Alu RNA or vehicle (PBS) was injected into the subretinal space of fellow eyes of two wild-type mice (left and right panels). 3-days later, DyeLight782-VAD-FMK3 was injected into the vitreous humor of both eyes. From baseline (0 hours) to 8 hours thereafter, photographs of the fundus (retina) were taken through the ICG filter of a Topcon 50IX camera. In the Alu RNA-injected eye, white fluorescent areas corresponding to bioactive caspase generation were observed in the area of Alu RNA injection. No such widespread areas were observed in the vehicle-injected eye.

Figure 27:
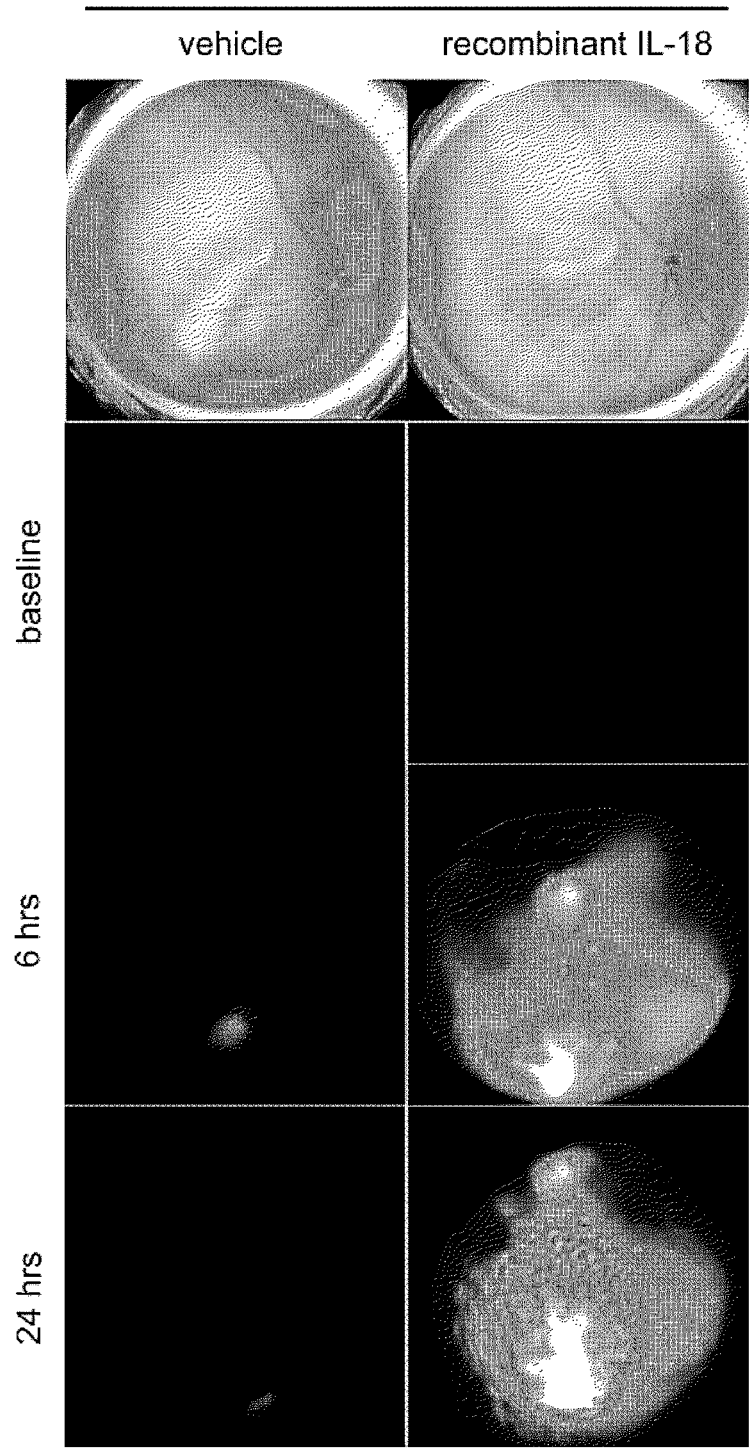

FIG. 27. Recombinant IL-18 or vehicle (PBS) was injected into the subretinal space of fellow eyes of a wild-type mouse. 2-days later, DyeLight782-VAD-FMK3 was injected into the vitreous humor of both eyes. From baseline (0 hours) to 24 hours thereafter, photographs of the fundus (retina) were taken through the ICG filter of a Topcon 50IX camera. In the IL-18-injected eye, white fluorescent areas corresponding to bioactive caspase generation were observed in the area of IL-18 injection. No such widespread areas were observed in the vehicle-injected eye.

Figure 28:
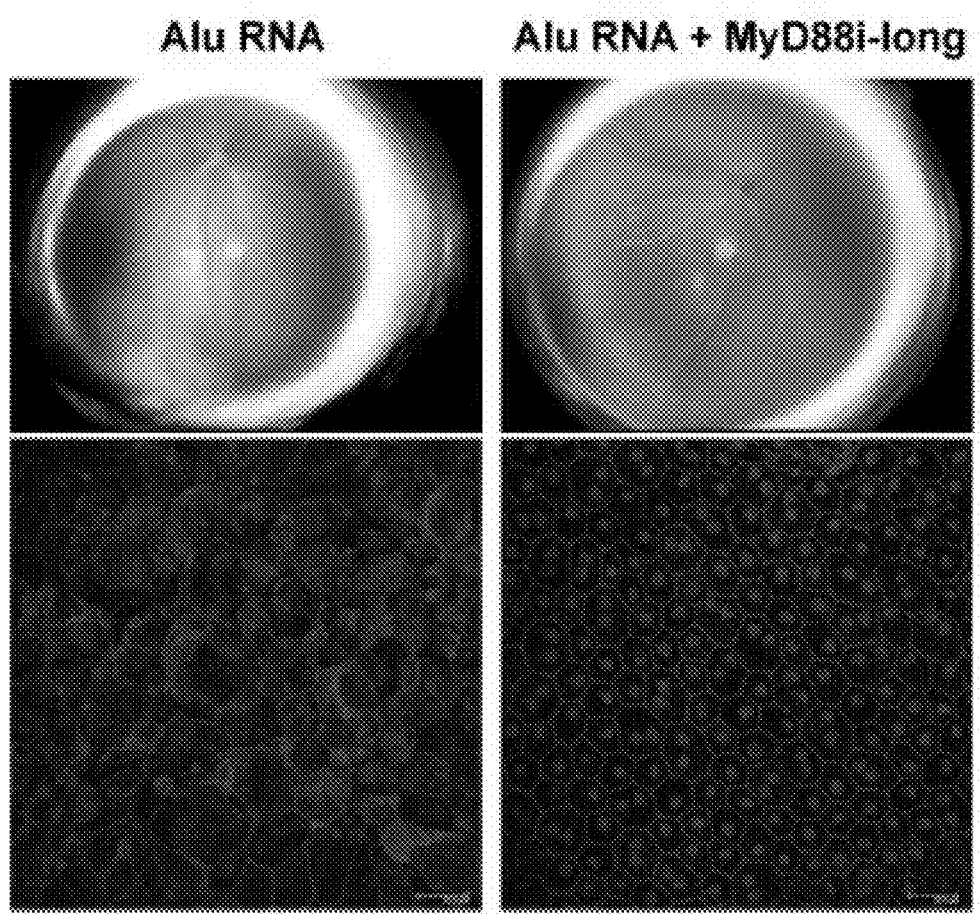

FIG. 28. Representative images show that subretinally injected Alu RNA (1 µg)-induced RPE degeneration is blocked by intravitreous administration of the MyD88 peptide inhibitor DRQIKIWFQNRRMKWKKRDV-LPGTCVWSIASE (2 µg). Top panels show color fundus photographs. Bottom panels show retinal flat mount preparations stained with an anti-ZO1 antibody (red). Alu RNA-induced RPE degeneration (left panels) is evidenced by depigmentation seen on color photos (top left) and dysmorphic appearing RPE cells (bottom left). Treatment with the MyD88 peptide inhibitor prevents those degenerative changes and preserves normal RPE anatomy.

BRIEF DESCRIPTION OF THE SEQUENCE LISTING

SEQ ID NO: 1. IMG-2005-1 peptide sequence: DRQIKIWFQNRRMKWKKRDVLPGT, wherein the last 7 amino acids are required for inhibition of MyD88 homodimerization, while the preceding amino acid sequence is an Antennopedia cell permeation sequence that enables the inhibitory peptide to enter the cell, so that it can block MyD88.

SEQ ID NO: 2. Control peptide sequence: DRQIKIWFQNRRMKWKK

SEQ ID NO: 3. MyD88 siRNA #1 sense: 5'-GAGAAGCCUUUACAGGUdTdT-3'

SEQ ID NO: 4. MyD88 siRNA #1 antisense: 5'-ACCUGUAAAGGCUUCUCdTdT-3'

SEQ ID NO: 5. MyD88 siRNA #2 sense: 5'-CAGAGCAAGGAAUGUGAdTdT-3'

SEQ ID NO: 6. MyD88 siRNA #2 antisense: 5'-UCACAUUCCUUGCUCUGdTdT-3'

SEQ ID NO: 7 NLRP3 siRNA—5'-GUUUGACUAUCUGUUCUdTdT-3'

SEQ ID NO: 8: NLRP3 siRNA—5'-GGAUCAAACUACUCUGUGA-3'

SEQ ID NO: 9: NLRP3 siRNA—5'-UGCAAGAUCUCUCAGCAAA-3'

SEQ ID NO: 10: NLRP3 siRNA—5'-GAAGUGGGGUUCAGAUAAU-3'

SEQ ID NO: 11: NLRP3 siRNA—5'-GCAAGACCAAGACGUGUGA-3'

SEQ ID NO: 12: PYCARD siRNA—5'-GAAGCUCUUCAGUUUCAdTdT-3'

SEQ ID NO: 13: PYCARD siRNA—5'-GGCUGCUGGAUGCUCUGUACGGGAA-3'

SEQ ID NO: 14: PYCARD siRNA—5'-UUCCCGUACAGAGCAUCCAGCAGCC-3'.

SEQ ID NO: 15: siRNA of the human Pyrin coding sequence: GCTGGAGCAGGTGTACTACTTC.

SEQ ID NO: 16: siRNA of the human NLRP3 coding sequence CAGGTTTGACTATCTGTTCT.

SEQ ID NO: 17: siRNA of the 3' UTR of the human caspase-1 GTGAAGAGATCCTTCTGTA.

SEQ ID NO: 18: Oligonucleotide primer for human MB, forward 5'-TTAAAGCCCGCCTGACAGA-3'.

SEQ ID NO: 19: Oligonucleotide primer for human MB, reverse 5'-GCGAATGACAGAGGGTTTCTTAG-3').

SEQ ID NO: 20: Oligonucleotide primer for human IL18, forward 5'-ATCACTTGCACTCCGGAGGTA-3'.

SEQ ID NO: 21: Oligonucleotide primer for human IL18, reverse 5'-AGAGCGCAATGGTGCAATC-3'.

SEQ ID NO: 22: Oligonucleotide primer for human NLRP3, forward 5'-GCACCTGTTGTGCAATCTGAA-3'.

SEQ ID NO: 23: Oligonucleotide primer for human NLRP3, reverse 5'-TCCTGACAACATGCTGATGTGA-3'.

SEQ ID NO: 24: Oligonucleotide primer for human PYCARD, forward 5'-GCCAGGCCTGCACTTTATAGA-3'.

SEQ ID NO: 25: Oligonucleotide primer for human PYCARD, reverse 5'-GTTTGTGACCCTCGCGATAAG-3'.

SEQ ID NO: 26: Oligonucleotide primer for human VDAC1, forward 5'-ACTGCAAAATCCCGAGTGAC-3'.

SEQ ID NO: 27: Oligonucleotide primer for human VDAC1, reverse 5'-CTGTCCAGGCAAGATTGACA-3'.

SEQ ID NO: 28: Oligonucleotide primer for human VDAC2, forward 5'-CAGTGCCAAATCAAAGCTGA-3'.

SEQ ID NO: 29: Oligonucleotide primer for human VDAC2, reverse 5'-CCTGATGTCCAAGCAAGGTT-3').

SEQ ID NO: 30: Oligonucleotide primer for human VDAC3, forward 5'-TTGACACAGCCAAATCCAAA-3'.

SEQ ID NO: 31: Oligonucleotide primer for human VDAC3, reverse 5'-GCCAAAACGGGTGTTGTTAC-3'.

SEQ ID NO: 32: Oligonucleotide primer for human 18S rRNA, forward 5'-CGCAGCTAGGAATAATGGAATAGG-3'.

SEQ ID NO: 33: Oligonucleotide primer for human 18S rRNA, reverse 5'-GCCTCAGTTCCGAAAACCAA-3'.

SEQ ID NO: 34: Oligonucleotide primer for mouse Myd88, forward 5'-CACCTGTGTCTGGTCCATTG-3'.

SEQ ID NO: 35: Oligonucleotide primer for mouse Myd88, reverse 5'-AGGCTGAGTGCAAACTTGGT-3'.

SEQ ID NO: 36: Oligonucleotide primer for mouse Nlrp3, forward 5'-ATGCTGCTTCGACATCTCCT-3'.

SEQ ID NO: 37: Oligonucleotide primer for mouse Nlrp3, reverse 5'-AACCAATGCGAGATCCTGAC-3'.

SEQ ID NO: 38: Oligonucleotide primer for mouse Il18, forward 5'-GACAGCCTGTGTTCGAGGAT-3'.

SEQ ID NO: 39: Oligonucleotide primer for mouse Il18, reverse 5'-TGGATCCATTTCCTCAAAGG-3'.

SEQ ID NO: 40: Oligonucleotide primer for mouse 18S rRNA, forward 5'-TTCGTATTGCGCCGCTAGA-3'.

SEQ ID NO: 41: Oligonucleotide primer for mouse 18S rRNA, reverse 5'-CTTTCGCTCTGGTCCGTCTT-3'.

SEQ ID NO: 42: Mouse miR-184-5'-TGGACGGAGAACTGATAAGGGT-3;

SEQ ID NO: 43: Mouse miR-221/222-5'-AGCTACATCTGGCTACTGGGT-3;

SEQ ID NO: 44: Mouse miR-320a-5'-AAAAGCTGGGTTGAGAGGGCGA-3', and

SEQ ID NO: 45: Mouse mouse miR-484-5'-TCAGGCTCAGTCCCCTCCCGAT-3'.

SEQ ID NO: 46: U6 snRNA-5'-AAATTCGTGAAGCGTTCC-3'.

SEQ ID NO: 47: VDAC1 siRNA sense-5'-CGGAAUAGCAGCCAAGUdTdT-3'.

SEQ ID NO: 48: VDAC2 siRNA sense-5'-CCCUGGAGUUGGAGGCUdTdT-3'.

SEQ ID NO: 49: VDAC3 siRNA sense-5'-GCUUUAAUCGAUGGGAAdTdT-3'.

SEQ ID NO: 50: DICER1 antisense oligonucleotide (AS)-5'-GCUGACCTTTTTGCTUCUCA-3'.

SEQ ID NO: 51: Control for DICER1 AS-5'-TTGGTACGCATACGTGTTGACTGTGA-3'.

SEQ ID NO: 52: Alu AS-5'-CCCGGGTTCACGCCATTCTCCTGCCTCAGCCTCA-CGAGTAGCTGGGACTACAGGCGCCCGACAC-CACTCCCGGCTAATTTTTTGTATTTTT-3'.

SEQ ID NO: 53: Control for Alu AS-5'-GCATGGCCA-GTCCATTGATCTTGCACGCTTGCC-TAGTACGCTCCTCAACCTATCCTCCTAGCCCGT-TACTTGGTGCCACCGGCG-3'.

SEQ ID NO: 54: Oligopeptide for inhibiting MyD88 homodimerization: RDVLPGT.

SEQ ID NO: 55: Oligopeptide for inhibiting MyD88 homodimerization: RDVVPGG.

SEQ ID NO: 56. MyD88 siRNA: UUAUUUCCUAAWGGGUCdTdT.

SEQ ID NO: 57. VDAC1 siRNA sense (5'-CGGAAUAGCAGCCAAGUdTdT-3').

SEQ ID NO: 58. VDAC2 siRNA sense (5'-CCCUGGAGUUGGAGGCUdTdT-3').

SEQ ID NO: 59. VDAC3 siRNA sense (5'-GCUUUAAUCGAUGGGAAdTdT-3').

SEQ ID NO: 60. MyD88 inhibitor: DRQIKIWFQNRRMKWKKRDVLPGTCVWSIASE.

SEQ ID NO: 61. MyD88 inhibitor: RDVLPGTCVWSIASE.

DESCRIPTION OF EXEMPLARY EMBODIMENTS

The presently-disclosed subject matter includes methods for identifying MyD88 inhibitors, and methods and compositions for inhibiting MyD88 and uses thereof. The presently-disclosed subject matter includes methods for identifying inflammasome inhibitors, and methods and compositions for inhibiting an inflammasome and uses thereof. The presently-disclosed subject matter includes methods for identifying inhibitors of components of inflammasome, and methods and compositions for inhibiting a component of inflammasome and uses thereof. Components of inflammasome include, for example, NLRP3, PYCARD, and Caspase-1. The presently-disclosed subject matter includes methods for identifying IL-18 inhibitors, and methods and compositions for inhibiting IL-18 and uses thereof. The presently-disclosed subject matter includes methods for identifying VDAC1 and VDAC2 inhibitors, and methods and compositions for inhibiting VDAC1 and VDAC2 and uses thereof. The presently-disclosed subject matter includes methods for identifying caspase-8 inhibitors, and methods and compositions for inhibiting caspase-8 and uses thereof. The presently-disclosed subject matter includes methods for identifying NFkB inhibitors, and methods and compositions for inhibiting NFkB and uses thereof. Also provided are methods and compositions for imaging activated caspase-1 in an eye of a subject.

The presently-disclosed subject matter includes methods including inhibiting one or more of an inflammasome, MyD88, and IL-18 of a cell. In some embodiments, the presently-disclosed subject matter includes methods including inhibiting one or more of MyD88, IL-18, VDAC1, VDAC2, NFκB, caspase-8, caspase-1, NLRP-3, PYCARD, and an inflammasome, including a component of an inflammasome (e.g., caspase 1, NLRP-3, PYCARD) of a cell.

In some embodiments of the method, the cell is selected from an RPE cell, a retinal photoreceptor cell, or a choroidal cell. In some embodiments, the cell is an RPE cell. In some embodiments, the cell is the cell of a subject. In some embodiments, the cell is a cell of a subject having, suspected of having, or at risk of having a condition of interest. In some embodiments, the cell is a cell of a subject having, suspected of having, or at risk of having age-related macular degeneration. In some embodiments, the cell is a cell of a subject having, suspected of having, or at risk of having geographic atrophy. In some embodiments, the cell is a cell of a subject having, suspected of having, or at risk of having geographic atrophy and the cell is an RPE cell. In some embodiments, a subject having age-related macular degeneration can be treated using methods and compositions as disclosed herein.

As used herein, the term "subject" refers to a target of treatment. The subject of the herein disclosed methods can be a vertebrate, such as a mammal, a fish, a bird, a reptile, or an amphibian. Thus, the subject of the herein disclosed methods can be a human or non human. Thus, veterinary therapeutic uses are provided in accordance with the presently disclosed subject matter.

In some embodiments, the inhibiting one or more of an inflammasome, MyD88, IL-18, VDAC1, VDAC2, NLRP3, PYCARD, caspase-1, caspase-8, and NFκB of a cell includes administering an inhibitor to the cell, or to a subject wherein the cell is the cell of a subject. Such inhibitors can be administered, for example, by intraocular injection (e.g., localized interocular therapy); intravitreous injection; sub-retinal injection; episcleral injection; sub-Tenon's injection; retrobulbar injection; peribulbar injection; transscleral administration; topical administration, e.g., topical eye drop application; suprachoroidal administration; release from a sustained release delivery device that is sutured to or attached to or placed on the sclera, or injected into the vitreous humor, or injected into the anterior chamber, or implanted in the lens bag or capsule; oral administration; or intravenous administration.

As used herein the term "inhibit" or "inhibiting" refers to suppressing, reducing, decreasing, or substantially eliminating the biological activity of a polypeptide, such as MyD88, IL-18, VDAC1, VDAC2, caspase-8, NFκB, or a polypeptide of an inflammasome (e.g., NLRP3, PYCARD, caspase-1). As used herein with reference to a polypeptide being inhibited, "of a cell" refers to a polypeptide that is inside the cell (inside the cell membrane), on the cell (in the cell membrane, presented on the cell membrane, otherwise on the cell), or outside of a cell, but insofar as the polypeptide is outside of the cell, it is in the extracellular mileu such that one of ordinary skill in the art would recognize the polypeptide as being associated with the cell. For example, VDAC1, VDAC2, caspase-8, NFκB, or a polypeptide of an inflammasome (e.g., NLRP3, PYCARD, caspase-1 of a cell could be in the cell. For another example MyD88 could be in the cell or on the cell. For yet another example, IL-18 could be outside the cell because it is secreted, but it would be recognized by one or ordinary skill in the art as being associated with the cell.

As will be understood by those skilled in the art upon studying this application, inhibition of an inflammasome, MyD88, IL-18, VDAC1, VDAC2, caspase-1, caspase-8, and NFκB of a cell can be achieved in a number of manners. In some embodiments the inhibition can be achieved by affecting the transcription or translation of the polypeptide, by degrading the polypeptide, by scavenging the polypeptide, or otherwise impacting the biological activity of the polypeptide Inhibition comprises administering an inhibitor. An inhibitor is a compound that affects such inhibition of the biological activity of a polypeptide. Such compounds can be, for example, a polypeptide (including oligonucleotide, and including a polypeptide that binds to the polypeptide-of-interest to affect inhibition), a small molecule (including a small chemical compound), a compound for RNA interference (including siRNA, miRNA, shRNA), an antibody (e.g., a neutralizing antibody against polypeptide of interest, an antibody that blocks polypeptide of interest from binding to a receptor), an aptamer, a dominant negative plasmid or vector, or a virus-encoded inflammasome.

The terms "polypeptide", "protein", and "peptide", which are used interchangeably herein, refer to a polymer of the 20 protein amino acids, or amino acid analogs, regardless of its size. The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, from internal portions of the reference polypeptide, or a combination thereof. A fragment can also be a "functional fragment," in which case the fragment retains some or all of the activity of the reference polypeptide as described herein.

The terms "modified amino acid", "modified polypeptide", and "variant" refer to an amino acid sequence that is different from the reference polypeptide by one or more amino acids, e.g., one or more amino acid substitutions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. The term functional variant includes a functional variant of a functional fragment of a reference polypeptide.

In some embodiments, the methods and compositions of the presently-disclosed subject matter can be used in a subject having, suspected of having, or at risk of having a condition of interest. In some embodiments, methods and compositions of the presently-disclosed subject matter can be used for treating a condition of interest. Examples of conditions of interest include, but are not limited to: Geographic atrophy (Kaneko, Dridi et al. 2011); Macular degeneration (Kaneko, Dridi et al. 2011); Keratitis (Guo, Gao et al. 2011); Gout (Chen, Shi et al. 2006); Acne vulgaris (Terhorst, Kalali et al. 2010); Crohn's disease (Reuter and Pizarro 2004; Abreu, Fukata et al. 2005; Medvedev, Sabroe et al. 2006); Ulcerative colitis (Reuter and Pizarro 2004; Abreu, Fukata et al. 2005; Medvedev, Sabroe et al. 2006); irritable bowel disease/irritable bowel syndrome (McKernan, Nolan et al. 2009); Type I diabetes (Devaraj, Tobias et al. 2011; von Herrath, Filippi et al. 2011); Type 2 diabetes (Hutton, Soukhatcheva et al. 2010; Nogueira-Machado, Volpe et al. 2011); Insulin resistance (Ghanim, Mohanty et al. 2008; Tilich and Arora 2011); Obesity (Fresno, Alvarez et al. 2011); Hemolytic-Uremic Syndrome (Batsford, Duermueller et al. 2011); Polyoma virus infection (Batsford, Duermueller et al. 2011); Immune complex renal disease (Anders, Banas et al. 2004; Anders and Schlondorff 2007); Acute tubular injury (Anders, Banas et al. 2004; Anders and Schlondorff 2007); Lupus nephritis (Anders, Banas et al. 2004; Anders and Schlondorff 2007); Familial cold autoinflammatory syndrome (Mariathasan, Weiss et al. 2006; Meng, Zhang et al. 2009); Muckle-Wells syndrome and neonatal onset multisystem inflammatory disease (Mariathasan, Weiss et al. 2006; Meng, Zhang et al. 2009); Chronic infantile neurologic cutaneous and articular auto-inflammatory diseases, Renal ischemia-perfusion injury (El-Achkar and Dagher 2006; Robson 2009); Glomerulonephritis (El-Achkar and Dagher 2006; Robson 2009); Cryoglobulinemia (Banas, Banas et al. 2008); Systemic vasculitides (Weyand, Ma-Krupa et al. 2005; Hurtado, Jeffs et al. 2008; Summers, Steinmetz et al. 2011); IgA nephropathy (Lim, Lee et al. 2011); Atherosclerosis (Curtiss and Tobias 2009); HIV/AIDS (Brichacek, Vanpouille et al. 2010); Malaria (Franklin, Ishizaka et al. 2011); Helminth parasites (Babu, Blauvelt et al. 2005; Venugopal, Nutman et al. 2009); Sepsis and septic shock (Knuefermann, Nemoto et al. 2002; Opal and Huber 2002; Cristofaro and Opal 2003; Chen, Koustova et al. 2007); Allergic asthma (Slater, Paupore et al. 1998; Park, Gold et al. 2001); Hay fever (Slater, Paupore et al. 1998; Park, Gold et al. 2001); Chronic obstructive pulmonary disease (Geraghty, Dabo et al. 2011); Drug-induced lung inflammation (Liu, Yang et al. 2010); Contact dermatitis (Martin, Dudda et al. 2008; Yokoi, Niizeki et al. 2009); Leprosy (Krutzik, Tan et al. 2005; Terhorst, Kalali et al. 2010); *Burkholderia cenocepacia* infection (Ventura, Balloy et al. 2009); Respiratory syncitial virus infection (Aeffner, Traylor et al. 2011); Psoriasis (Zuany-Amorim, Hastewell et al. 2002; Barrat and Coffman 2008; Li, Zhou et al. 2009); Systemic lupus erythematosus (Zuany-Amorim, Hastewell et al. 2002; Barrat and Coffman 2008; Li, Zhou et al. 2009); Scleroderma (Zuany-Amorim, Hastewell et al. 2002; Barrat and Coffman 2008; Li, Zhou et al. 2009); Reactive arthritis (Zuany-Amorim, Hastewell et al. 2002; Barrat and Coffman 2008; Li, Zhou et al. 2009); Cystic fibrosis, Syphilis, Sjögren's syndrome (Zuany-Amorim, Hastewell et al. 2002; Barrat and Coffman 2008; Li, Zhou et al. 2009); Rheumatoid arthritis (Zuany-Amorim, Hastewell et al. 2002; Barrat and Coffman 2008; Li, Zhou et al. 2009); Inflammatory joint disease (O'Neill 2008); Non-alcoholic fatty liver disease (Tan, Fiel et al. 2009); Cardiac surgery (peri-/post-operative inflammation) (Cremer, Martin et al. 1996; Taylor 1996; Dybdahl, Wahba et al. 2002); Acute and chronic organ transplant rejection (Alegre, Leemans et al. 2008; Miller, Rossini et al. 2008; Taylor, Ehrhardt et al. 2008; Krams, Wang et al. 2010; Wang, Schmaderer et al. 2010; Shin and Harris 2011; Testro, Visvanathan et al. 2011); Acute and chronic bone marrow transplant rejection (Alegre, Leemans et al. 2008; Miller, Rossini et al. 2008; Taylor, Ehrhardt et al. 2008; Krams, Wang et al. 2010; Wang, Schmaderer et al. 2010; Shin and Harris 2011; Testro, Visvanathan et al. 2011); Alzheimer's disease; and Tumor angiogenesis (Frantz, Vincent et al. 2005; Schmid, Avraamides et al. 2011).

As used herein, the terms treatment or treating relate to any treatment of a condition of interest, including but not limited to prophylactic treatment and therapeutic treatment. As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

In some embodiments, the methods and compositions of the presently-disclosed subject matter are useful for protecting the cell against Alu-RNA-induced degeneration. As such, in some embodiments, a method includes administering an inhibitor, wherein the cell is protected against Alu-RNA-induced degeneration.

Inhibiting Inflammasome

In some embodiments, the presently-disclosed subject matter includes a method of protecting a cell, comprising: inhibiting an inflammasome of the cell. The method of any one of the prior claims, wherein the inflammasome is selected from NLRP3 inflammasome, NLRP1 inflammasome, NLRC4 inflammasome, AIM2 inflammasome, and IFI16 inflammasome. In some embodiments, the inflammasome is the NLRP3 inflammasome.

In some embodiments the inhibiting the inflammasome includes inhibiting a component of the inflammasome. In some embodiments the inflammasome components can include a polypeptide encoded by PYCARD. In some embodiments the inflammasomse components can include a caspase. In some embodiments the inflammasome components can include PYCARD, NLRP3, and caspase-1.

In some embodiments, the inhibiting the inflammasome comprises administering an inflammasome inhibitor. The inflammasome inhibitor can be an inhibitor of a component of the inflammasome. In some embodiments, the inflammosome As noted above, in some embodiments, inhibiting a polypeptide of interest to the presently-disclosed subject matter comprises administering an oligonucleotide or a small RNA molecule. Such small RNA molecule can target, for example, NLRP3 and/or PYCARD. Such nucleotides can target and degrade NLRP3 and/or PYCARD. In this regard, the presently-disclosed subject matter includes a isolated double-stranded RNA molecule that inhibits expression of NLRP3 and/or PYCARD, wherein a first strand of the double-stranded RNA comprises a sequence as set forth in Table A, and includes about 14 to 25 nucleotides. As noted above, in some embodiments, inhibiting comprises administering an inflammasome inhibitor that is a dominant negative vector. In some embodiments, inhibiting inflammasome comprises administering an inhibitor of Caspase-1. In some embodiments the inhibitor of Caspase-1 is a peptide inhibitor.

Examples of inflammasome inhibitors that can be used in accordance with the presently-disclosed subject matter include, but are not limited to those set forth in Table A. As such, embodiments of the presently-disclosed subject matter can include administering an inflammasome inhibitor set forth in Table A.

TABLE A

Examples of Inflammasome Inhibitors

Ion channel inhibitors, for example, glybenclamide/glyburide (CAS Number: 10238-21-8) (Lamkanfi, et al., 2009).

IkB-α inhibitors, for example, BAY11-7082 (CAS Number: 195462-67-7; also known as (E)-3-(4-Methylphenylsulfonyl)-2-propenenitrile) (Juliana, et al., 2010).

Compounds similar to BAY11-7082, for example, other related vinyl sulfone compounds, as set forth in Lamkanfi, et al., 2009; Juliana, et al., 2010; deRivero Vaccari, et al., 2008; and Newman, et al., 2011, which are incorporated herein by this reference.

TABLE A-continued

Examples of Inflammasome Inhibitors

Antibodies, for example, Anti-ASC and Anti-NALP1 and antibodies based on protein
sequences selected from: ASC: ALR QTQ PYL VTD LEQ S; NALP1: MEE SQS KEE SNT
EG-cys (deRivero Vaccari, et al., 2008); and Anti-NALP1 (Abcam, Cambridge, MA), anti-
IL-1β (Cell Signaling Technology, Beverly, MA), anti-IL-18 (R & D Systems, Minneapolis,
MN), anti-caspase-1 (Millipore, Billerica, MA), anti-caspase-1 (Santa Cruz Biotechnology,
Santa Cruz, CA), anti-caspase-11 (Alexis Biochemicals, San Diego, CA), anti-caspase-11
(Santa Cruz Biotechnology).

Direct inhibitors of Caspase-1 and/or NLRP3, for example, parthenolide (Juliana, et al.,
2010).

Caspase-1 inhibitors, such as estrogen binding B-box protein (Munding et al., 2006); COP
(Lee, et al., 2001); ICEBERG (Humke, et al., 2000); and Z-WEHD-FMK (R&D Systems).

Caspase 1 and/or 4 inhibitors, for example, Ac-YVAD-CHO (Ac-Tyr-Val-Ala-Asp-CHO)
and Ac-YVAD-CMK (CAS Number: 178603-78-6; N-acetyl-L-tyrosyl-L-valyl-N-[(1S)-
1-(carboxymethyl)-3-chloro-2-oxo-propyl]-L-alaninamide) (Hilbi, et al., 1997).

Caspase-12 inhibitors (Saleh, et al., 2006).

Host-derived inhibitors of Caspase-1, for example, cellular PYRIN domain (PYD)-only
proteins (POP) family: cPOP1 and cPOP2 (Stehlik, et al., 2003; Dorfleutner, et al., 2007);
serpin proteinase inhibitor 9 (PI-9) (Young, et al., 2000); BCL-2 and BCL-xL (Young, et al.,
2000).

Inhibitors of Nlrp1b inflammasome, for example, auranofin (Newman, et al., 2011).

Virus expressed inhibitors of the inflammasome, for example, PYD homologs M13L-PYD,
S013L (Benedict, et al., 2005; Dorfleutner, et al., 2007; Johnston, et al., 2005); SPI-2
homologs CrmA, Serp2, SPI-2, (Komiyama, et al., 1994; Kettle, et al., 1997; Messud-Petit, et
al., 1998); NS1 (Stasakova, et al., 2005); Kaposi Sarcoma-associated Herpesvirus Orf63

(Gregory, et al., 2011).

Potassium chloride (KCl) (CAS Number: 7447-40-7 (Schorn, et al. 2011).

Cathepsin-B inhibitors, for example, CA-074 Me (L-3-trans-(Propylcarbamoyl)oxirane-2-
Carbonyl)-L-Isoleucyl-L-Proline Methyl Ester (Li, et al., 2009).

Cytochalasin D (Dostert, et al., 2008).

ROS inhibitors, for example, N-acetyl-L-cysteine (NAC), and (2R,4R)-4-aminopyrrolidine-
2,4-dicarboxylate (APDC) (Dostert, et al., 2008).

ASC-1 inhibitors, for example, cellular pyrin domain (PYD) superfamily proteins, also
known as M013 (Rahman, et al., 2009).

NLRP3 inflammasome pan-caspase inhibitors, for example, Z-VAD-FMK (Dostert, et al.,
2009).

Microtubules, for example, colchicine (CAS Number: 64-86-8) (Martinon, et al., 2006).

An isolated double-stranded RNA molecule that inhibits expression of NLRP3, and which
can be conjugated to cholesterol or not, and at least one strand including the sequence:
GUUUGACUAUCUGUUCUdTdT (SEQ ID NO: 7).

An isolated double-stranded RNA molecule that inhibits expression of NLRP3, at least one
strand of which includes a sequence selected from: 5'-GGAUCAAACUACUCUGUGA-3'
(SEQ ID NO: 8); 5'-UGCAAGAUCUCUCAGCAAA-3' (SEQ ID NO: 9); 5'-
GAAGUGGGUUCAGAUAAU-3' (SEQ ID NO: 10); and 5'-
GCAAGACCAAGACGUGUGA-3')(SEQ ID NO: 11) (Wong, et al., 2011).

An isolated double-stranded RNA molecule that inhibits expression of PYCARD, at least one
strand of which includes the sequence of: 5'-GAAGCUCUUCAGUUUCAdTdT-3' (SEQ ID
NO: 12).

An isolated double-stranded RNA molecule that inhibits expression of PYCARD, at least one
strand of which includes a sequence selected from: 5'-GAAGCUCUUCAGUUUCAdTdT-3'
(SEQ ID NO: 12); 5'-GGCUGCUGGAUGCUCUGUACGGGAA-3' (SEQ ID NO: 13); and
5'-UUCCCGUACAGAGCAUCCAGCAGCC-3' (SEQ ID NO: 14). (Stealth siRNA oligos
were designed and obtained with Lipofectamine 2000).

Further information regarding Caspase-1 inhibitors and probes can be found in Table B. Information found at the links set forth in Table B as of the filing date of this application is incorporated herein by this reference.

including about 14 to 25 nucleotides: 5'-GUUUGAC-UAUCUGUUCUdTdT-3' (SEQ ID NO: 7); 5'-GGAU-CAAACUACUCUGUGA-3' (SEQ ID NO: 8); 5'-UG-CAAGAUCUCUCAGCAAA-3' (SEQ ID NO: 9);

TABLE B

| Peptide Sequence | Application | Link | Notes |
| --- | --- | --- | --- |
| GWEHDGK | fluorescent in vivo | http://www.ncbi.nlm.nih.gov/pmc/articles/PMC1502090/ | Gly-Trp-Glu-His-Asp-Gly-Lys |
| YVADAPV | fluorescent | http://www.ncbi.nlm.nih.gov/pubmed/8012123 | DABCYL-Tyr-Val-Ala-Asp-Ala-Pro-Val-EDANS |
| GFEVD | fluorescent | http://www.ncbi.nlm.nih.gov/pmc/articles/PMC1221285/pdf/10947972.pdf | Abz-GXEVD-GVY(NO2)D |
| GYEVD | fluorescent | http://www.ncbi.nlm.nih.gov/pmc/articles/PMC1221285/pdf/10947972.pdf | Abz-GXEVD-GVY(NO2)D |
| YVAD | fluorescent | http://www.sciencedirect.com/science/article/pii/S1074552199800519 | BFP-YVAD-GFP |
|  | fluorescent | http://www.jbc.org/content/286/37/32513.full | Ac-YVAD-CHO |
|  | inhibitor | http://www.jbc.org/content/273/49/32608.long |  |
| WEHD | fluorescent | http://jem.rupress.org/content/191/11/1819/T1.expansion.html | KDPC₅G-WEHD-GINGC₅PKGY |
|  | Inhibitor | http://www.jbc.org/content/273/49/32608.long |  |
| YVHDAP | fluorescent | http://www.funakoshi.co.jp/data/datasheet/ONC/CPL1RE-5.pdf | Caspalux |
| YVADAP | fluorescent | http://www.ncbi.nlm.nih.gov/pubmed/8012123 | DABCYL-YVADAP-EDANS |
| YEVD | fluorescent | http://www.jbc.org/content/272/15/9677.long | Ac-YVED-pNA |
| YVHDAPVR | Kinetic substrate | http://www.jbc.org/content/272/11/7223/T1.expansion.html |  |

| Small molecule Sequence | Application | Link | Notes |
| --- | --- | --- | --- |
| VX-765 | Inhibitor | http://www.medkoo.com/Anticancer-trials/VX-765.htm | Vertex Pharmaceuticals, Reversible, clinical trials |
| ML132 | Inhibitor | http://www.ncbi.nlm.nih.gov/books/NBK56241/ | Reversible(?), based on VX-765 |
| VX-740 | Inhibitor | http://www.ncbi.nlm.nih.gov/pubmed/17393315 | Vertex Pharmaceuticals, common name: Pralnacasan clincal trials halted (liver abnormalities) |
| VRT-018858 | Inhibitor | http://www.ncbi.nlm.nih.gov/pubmed/17845807 | Active metabolite of VX-740 |
| CM-269 | Reporter | http://www.sciencedirect.com/science/article/pii/S1074552110003091#sec5.1 | Luciferase based reporter |

The presently-disclosed subject matter further includes compositions useful for inhibiting an inflammasome. Such compositions include an inhibitor. As noted above, such inhibitors can be, for example, a nucleotide, a polypeptide, a small (chemical) molecule, etc. In some embodiments, a composition can include an isolated RNA molecule.

The presently-disclosed subject matter includes isolated RNA molecules that inhibit expression of a component of inflammasome, e.g., NLRP3, caspase-1 and/or PYCARD. In some embodiments, a first strand of the double-stranded RNA comprises a sequence selected from the following, and including about 14 to 25 nucleotides: 5'-GAAGUGGGGUUCAGAUAAU-3' (SEQ ID NO: 10); 5'-GCAAGACCAAGACGUGUGA-3' (SEQ ID NO: 11); 5'-GAAGCUCUUCAGUUUCAdTdT-3' (SEQ ID NO: 12); 5'-GGCUGCUGGAUGCUCUGUACGGGAA-3' (SEQ ID NO: 13); and 5'-UUCCCGUACAGAGCAUCCAGCA-GCC-3' (SEQ ID NO: 14).

The presently-disclosed subject matter includes isolated RNA molecules that inhibit expression of an inflammasome component. In some embodiments, the RNA molecule comprises a sequence selected from the following:

```
GCTGGAGCAGGTGTACTACTTC,                             (SEQ ID NO: 15)

(SEQ ID NO: 16)
CAGGTTTGACTATCTGTTCT,
and (SEQ ID NO: 17)
GTGAAGAGATCCTTCTGTA.
```

The presently-disclosed subject matter further includes methods of screening candidate inhibitors to identify inflammasome inhibitors. In some embodiments, a method of identifying an inflammasome inhibitor makes use of a cultured cell wherein a cell based-system is provided, which measures PYCARD aggregation, Caspase-1 cleavage, or cleavage/secretion of IL-1β or IL-18 in response to an activator of the inflammasome (e.g., Alu RNA, lipopolysaccharide+ATP).

In some embodiments, a screening method for inflammasome inhibitors includes stimulating cells (e.g., RPE cells) or a cell line (e.g., THP-1 or RAW macrophages) that has been transfected with a plasmid encoding a fluorescent-tagged PYCARD with Alu RNA or LPS+ATP; monitoring the aggregation of fluorescent PYCARD into a "speck"—an aggregosome focus using fluorescent microscopy; and testing the candidate molecules for the degree of inhibition of PYCARD "speck" formation.

In some embodiments, a screening method for inflammasome inhibitors includes stimulating cells (e.g., RPE cells) or a cell line (e.g., THP-1 or RAW macrophages with Alu RNA or LPS+ATP; monitoring Caspase-1 activity using CaspaLux®1-E2D2 assay (OncoImmunin, Inc.); and testing the candidate molecules for the degree of inhibition of Caspaslux fluorescence.

In some embodiments, a screening method for inflammasome inhibitors includes stimulating cells (e.g., RPE cells) or a cell line (e.g., THP-1 or RAW macrophages with Alu RNA or LPS+ATP; monitoring Caspase-1 activity by measuring the abundance of cleaved Caspase-1 (p10 or p20 isoforms) by Western blotting using an anti-Caspase-1 antibody; and testing the candidate molecules for the degree of inhibition of Caspase-1 cleaved fragments (p10 or p20).

In some embodiments, a screening method for inflammasome inhibitors includes stimulating HEK-Blue™ IL-1β Cells (Invivogen) with Alu RNA or LPS+ARP to detect bioactive IL-1β formation using QUANT1-Blue™ (Invivogen); and testing the candidate molecule for degree of inhibition of colometric signal.

Inhibiting MyD88

In some embodiments, the presently-disclosed subject matter includes a method of protecting a cell, comprising: inhibiting MyD88 of the cell. In some embodiments, the inhibiting MyD88 comprises administering a MyD88 inhibitor.

As noted above, in some embodiments, inhibiting a polypeptide of interest to the presently-disclosed subject matter comprises administering an oligonucleotide or a small RNA molecule. Such small RNA molecule can target MyD88. Such nucleotides can target and degrade MyD88. In this regard, the presently-disclosed subject matter includes a isolated double-stranded RNA molecule that inhibits expression of MyD88, wherein a first strand of the double-stranded RNA comprises a sequence as set forth in Table C, and includes about 14 to 25 nucleotides. Examples of MyD88 inhibitors that can be used in accordance with the presently-disclosed subject matter include, but are not limited to those set forth in Table C. As such, embodiments of the presently-disclosed subject matter can include administering a MyD88 inhibitor set forth in Table C.

TABLE C

```
Examples of MyD88 Inhibitors

A inhibitor comprising the polypeptide sequence of IMG-2005-1 peptide sequence:
DRQIKIWFQNRRMKWKKRDVLPGT (SEQ ID NO: 1), including about 29 to 100
nucleotides.
Oligopeptide for inhibiting MyD88 homodimerization: RDVLPGT (SEQ ID NO: 54)
Oligopeptide for inhibiting MyD88 homodimerization: RDVVPGG (SEQ ID NO: 55)
Loiarro et al. J Biol Chem 2005; 280:15809-14.

DRQIKIWFQNRRMKWKKRDVLPGTCVWSIASE (SEQ ID NO: 60).

RDVLPGTCVWSIASE (SEQ ID NO: 61).

An isolated double-stranded RNA molecule that inhibits expression of MyD88, at least
one strand of which is about 14 to 25 nucleotides and includes a sequence selected
from: 5'-GAGAAGCCUUUACAGGUdTdT-3' (SEQ ID NO: 3);
5'-ACCUGUAAAGGCUUCUCdTdT-3' (SEQ ID NO: 4);
5'-CAGAGCAAGGAAUGUGAdTdT-3' (SEQ ID NO: 5);
5'-UCACAUUCCUUGCUCUGdTdT-3' (SEQ ID NO: 6); and
5'-UAUUUCCUAAWGGGUCdTdT-3' (SEQ ID NO: 56).

A homodimerization inhibitor, such as Pepinh-MYD (Invitrogen).

A a dominant negative or splice variant of MyD88, such as a MyD88 splice variants that
lack exon 2 (also known as the "intermediate domain" (e.g., having sequences set for at
accession numbers NM_001172566.1 and NM_001172568.1), or other splice variants of MyD88
(e.g., having sequences set for at accession numbers NM_002468.4 and NM_001172569.1).
```

As noted above, in some embodiments, inhibiting MyD88 comprises administering an MyD88 inhibitor that is a dominant negative vector against MyD88, e.g., a dominant negative inhibitory form of MyD88 (pMyD88-dn) that contains the truncated ΔMyD88 (amino acids 152-296) lacking the death domain of MyD88 (Muzio et al. IRAK (Pelle) Family Member IRAK-2 and MyD88 as Proximal Mediators of IL-1 Signaling. *Science* 1997; 278:1612-1615).

As noted above, in some embodiments, inhibiting MyD88 comprises administering an MyD88 inhibitor that is a small molecule (e.g., (1) hydrocinnamoyl-L-valyl pyrrolidine, referred to as compound 4a in Bartfai et al. "A low molecular weight mimic of the Toll/IL-1 receptor/resistance domain inhibits IL-1 receptor-mediated responses." *PNAS* 2003; 100: 7971-7976; or (2) ST2825 as described in Carminati, P., Gallo, G., Ruggiero, V., Sassano, M., Mastroianni, D. "MyD88 homodimerization inhibitors" Patent No. WO2006067091 and characterized in Loiarro et al "Inhibition of MyD88 dimerization and recruitment of IRAK1 and IRAK4 by a novel peptidomimetic compound." *Journal of Leukocyte Biology.* 2007; 82:801-810; or (3) 4-[(E)-2-(1-hexylpyridin-1-ium-2-yeethenyl]-N,N-dimethylaniline iodide, also known as 4-[(E)-2-(1-hexylpyridin-6-yl)ethenyl]-N,N-dimethyl-aniline Iodide, also known as Chemical Structure CID 5716367 in PubChem which blocks MyD88 interactions, or (4) the compounds referred to as 50-F12 and 26-J10 in Lee et al. "Application of β-Lactamase Enzyme Complementation to the High-Throughput Screening of Toll-Like Receptor Signaling Inhibitors." *Molecular Pharmacology* 2007; 72:868-875), or a natural product (malyngamide F acetate as described in Villa et al. "Selective MyD88-dependent pathway inhibition by the cyanobacterial natural product malyngamide F acetate." *European Journal of Pharmacology* 2010; 629:140-146), or a DNA or RNA aptamer generated by SELEX or other screening technology that binds or blocks MyD88.

The presently-disclosed subject matter further includes compositions useful for inhibiting MyD88. Such compositions include an inhibitor. As noted above, such inhibitors can be, for example, a nucleotide, a polypeptide, a small (chemical) molecule, etc. In some embodiments, a composition can include an isolated RNA molecule.

The presently-disclosed subject matter includes isolated RNA molecules that inhibit expression of MyD88. In some embodiments, a first strand of the double-stranded RNA comprises a sequence selected from the following, and including about 14 to 25 nucleotides: 5'-GAGAAGC-CUUUACAGGUdTdT-3' (SEQ ID NO: 3); 5'-ACCU-GUAAAGGCUUCUCdTdT-3' (SEQ ID NO: 4); 5'-CA-GAGCAAGGAAUGUGAdTdT-3' (SEQ ID NO: 5); and 5'-UCACAUUCCUUGCUCUGdTdT-3' (SEQ ID NO: 6).

The presently-disclosed subject matter includes isolated polypeptide molecules that inhibit expression of MyD88. In some embodiments, the polypeptide molecule comprises a sequence selected from the following: DRQIKIWFQN-RRMKWKKRDVLPGT (SEQ ID NO: 1), including about 29 to 100 amino acids. In some embodiments, the polypeptide molecule comprises a sequence selected from the following: RDVLPGT (SEQ ID NO: 54) and RDVVPGG (SEQ ID NO: 55).

In some embodiments, a method of identifying a MyD88 inhibitor makes use of a cultured cell wherein MyD88 is upregulated. Candidate compounds can be screened using the cultured cell to determine efficacy in modulating MyD88. Candidate compounds include, for example, small molecules, biologics, and combinations thereof, such as compositions including multiple compounds. The term small molecules is inclusive of traditional pharmaceutical compounds. The term biologics is inclusive of polypeptides and nucleotides, and including siRNAs, antibodies, aptamers, and dominant negative plasmids or vectors.

In some embodiments, the screening method includes providing a cell in culture wherein MyD88 is upregulated; and contacting a candidate compound with the cell. The method can further include identifying a change in MyD88. For example, a measurable change in MyD88 levels can be indicative of efficacy associated with the candidate compound. In some embodiments, wherein the change in the MyD88 is a measurable decrease in MyD88, the change is an indication that the candidate compound is a MyD88 inhibitor. Such MyD88 inhibitors can have utility for therapeutic applications as disclosed herein.

In some embodiments, the MyD88 can be upregulated using Alu RNA or lipopolysaccharide (LPS), for example, by stimulating cells (macrophages or RPE cells) with Alu RNA or LPS. In some embodiments, the MyD88 can be upregulated using CpG nucleotides, for example, by stimulating cells (macrophages or RPE cells) with synthetic oligonucleotides containing unmethylated CpG dinucleotides, such as 5'-tcg tcg ttt tgt cgt ttt gtc gtt-3' or 5'-ggG GGA CGA TCG TCg ggg gg-3'. In some embodiments, the MyD88 can be upregulated using interleukin-1 beta or interleukin 18, for example, by stimulating cells (macrophages or RPE cells) with recombinant forms of interleukin-1 beta or interleukin 18.

In some embodiments of the method for identifying a MyD88 inhibitor, a change in the MyD88 can be monitored by measuring cell viability, measuring the expression of genes known to be induced by MyD88 signaling (e.g., Cox-2, Socs3, TNF-alpha) or using other criteria that would be recognized by one of ordinary skill in the art, using methods known to one of ordinary skill in the art. In some embodiments, the cultured cell is an RPE cell. In some embodiments, the cell is a retinal photoreceptor cell. In some embodiments, the cell is a choroidal cell.

In some embodiments, a method of identifying a MyD88 inhibitor includes providing a cultured cell wherein MyD88 is upregulated or undergoes oligomerization or induces phosphorylation of IRAK1 or of IRAK4; and contacting the cell with a candidate compound; and determining whether the candidate compound results in a change in the MyD88 levels, or a change in the abundance of dimerized or oligomerized MyD88, or a change in the abundance of phosphorylated IRAK1 or of phosphorylated IRAK4. In some embodiments, the MyD88 is upregulated by: Alu RNA, lipopolysacharide, CpG nucleotides, single-stranded RNA, interleukin-1 beta, or interleukin 18. In some embodiments, the MyD88 is monitored by measuring cell viability, or measuring the expression of a gene known to be induced by MyD88 signaling. In some embodiments, the gene known to be induced by MyD88 signaling is selected from Cox-2, Socs3, and TNF-α.

In some embodiments of a screening method for MyD88 inhibitors, cells or cell lines can be stimulated with a known activator of MyD88, e.g., Alu RNA, or LPS. The RNA levels of genes such as Cox2, Socs3, or TNF-α can be measured using quantitative real-time RT-PCR. Candidate molecules can be tested for degree of inhibition of these gene transcripts.

In some embodiments of a screening method for MyD88 inhibitors, cells or cell lines can be stimulated with a known activator of MyD88, e.g., Alu RNA, or LPS. The abundance of dimerized or oligomerized MyD88 can be measured by Western blotting under non-reducing conditions using an anti-MyD88 antibody. The candidate molecule can be tested for degree of inhibition of MyD88 dimerization or oligomerization.

In some embodiments of a screening method for MyD88 inhibitors, cells or cell lines that have been transfected with plasmids coding for a fusion MyD88 protein tagged to fragments of YFP (yellow fluorescent protein) can be stimulated with a known activator of MyD88, e.g., Alu RNA, or LPS. The fluorescent signal can be measured using bimolecular fluorescence complementation techniques. The candidate molecule can be tested for degree of inhibition of fluorescent signal.

In some embodiments of a screening method for MyD88 inhibitors, cells or cell lines can be stimulated with a known activator of MyD88, e.g., Alu RNA, or LPS. The abundance of phosphorylated forms of IRAK1 or IRAK4 can be measured by Western blotting under reducing conditions using an anti-phosphoIRAK1 or anti-phosphoIRAK4 antibodies. The candidate molecule can be tested for degree of inhibition of IRAK1 or IRAK4 phosphorylation.

Inhibiting IL-18

In some embodiments, the presently-disclosed subject matter includes a method of protecting a cell, comprising: inhibiting IL-18 of the cell. In some embodiments, the inhibiting IL-18 comprises administering an IL-18 inhibitor.

As noted above, in some embodiments, inhibiting a polypeptide of interest to the presently-disclosed subject matter comprises administering a binding protein or an antibody. Such antibodies can include a neutralizing antibody against IL-18, or an antibody that blocks IL-18 binding to the IL-18 receptor. In some embodiments, the IL-18 inhibitor can be an IL-18 binding protein (Novick, et al., 1999).

Examples of IL-18 inhibitors that can be used in accordance with the presently-disclosed subject matter include, but are not limited to those set forth in Table D. As such, embodiments of the presently-disclosed subject matter can include administering an IL-18 inhibitor set forth in Table D.

TABLE D

Examples of IL-18 Inhibitors

A neutralizing antibody against IL-18, or an antibody that blocks IL-18 binding to the IL-18 receptor, e.g., IL-18 neutralizing antibody (MBL International); IL-18 neutralizing antibody (R&D Systems); or IL-18R1 neutralizing antibody (R&D Systems); or IL-18R1 neutralizing antibody (Genetex).
An IL-18 binding protein as described by Novick, et al., 1999.
IL18BP (an endogenous, naturally occurring IL-18 binding protein)

The presently-disclosed subject matter further includes compositions useful for inhibiting IL-18. Such compositions include an inhibitor. As noted above, such inhibitors can be, for example, a nucleotide, a polypeptide, a small (chemical) molecule, etc. In some embodiments, a composition can include an isolated RNA molecule. In some embodiments, a composition can include an antibody or a binding protein.

The presently-disclosed subject matter further includes methods of screening candidate inhibitors to identify IL-18 inhibitors. In some embodiments, a method of identifying an IL-18 inhibitor includes plating recombinant IL-18R1 on a solid state surface suitable for surface plasmon resonance (SPR); exposing the plated recombinant IL-18R1 to fluorescence-labeled recombinant IL-18; further exposing the system to a putative IL-18 inhibitor which would displace IL-18:IL-18R1 binding; and measuring fluorescence to determine degree of inhibition.

In some embodiments, a method of identifying an IL-18 inhibitor includes stimulating cells (e.g., RPE cells) or a cell line (e.g., THP-1 or RAW macrophages) with recombinant IL-18; measuring MyD88 activation, e.g., by measuring increased MyD88 dimerization (through Western blotting) or by measuring increased phosphorylation of IRAK1 or of IRAK4.

Inhibiting VDAC1 and/or VDAC2

In some embodiments, the presently-disclosed subject matter includes a method of protecting a cell, comprising: inhibiting VDAC1 and/or VDAC2 of the cell. In some embodiments, the inhibiting VDAC1 and/or VDAC2 comprises administering an VDAC1 and/or VDAC2 inhibitor.

As noted above, in some embodiments, inhibiting a polypeptide of interest to the presently-disclosed subject matter comprises administering an oligonucleotide or a small RNA molecule. Such small RNA molecule can target VDAC1 and/or VDAC2. Such nucleotides can target and degrade VDAC1 and/or VDAC2. In this regard, the presently-disclosed subject matter includes a isolated double-stranded RNA molecule that inhibits expression of VDAC1 and/or VDAC2, wherein a first strand of the double-stranded RNA comprises a sequence as set forth in Table E, and includes about 14 to 25 nucleotides. Examples of VDAC1 and/or VDAC2 inhibitors that can be used in accordance with the presently-disclosed subject matter include, but are not limited to those set forth in Table E. As such, embodiments of the presently-disclosed subject matter can include administering a VDAC1 and/or VDAC2 inhibitor set forth in Table E.

TABLE E

Examples of VDAC1 and/or VDAC2 Inhibitors

An isolated double-stranded RNA molecule that inhibits expression of VDAC1, at least one strand of which is about 14 to 25 nucleotides and includes the sequence of: 5'-CGGAAUAGCAGCCAAGUdTdT-3' (SEQ ID NO: 47).

An isolated double-stranded RNA molecule that inhibits expression of VDAC2, at least one strand of which is about 14 to 25 nucleotides and includes the sequence of: 5'-CCCUGGAGUUGGAGGCUdTdT-3' (SEQ ID NO: 48).

Any phosphorothioate oligonucleotide randomer (Trilink Industries), which all inhibit VDAC (Stein & Marco Colombini. Specific VDAC inhibitors: phosphorothioate oligonucleotides. J Bioenerg Biomembr 2008; 40:157-62; Tan et al. Phosphorothioate oligonucleotides block the VDAC channel. Biophys J. 2007; 93:1184-91)

Cyclosporin A-blocks VDAC1

Superoxide dismutase 1-blocks VDAC1

4,4'-diisothiocyanatostilbene-2,2'-disulfonic acid (DIDS)-blocks VDAC1

Bcl-x(L) BH4(4-23)-blocks VDAC

TRO19622-blocks VDAC

The presently-disclosed subject matter further includes compositions useful for inhibiting VDAC1 and/or VDAC2. Such compositions include an inhibitor. As noted above, such inhibitors can be, for example, a nucleotide, a polypeptide, a small (chemical) molecule, etc. In some embodiments, a composition can include an isolated RNA molecule.

The presently-disclosed subject matter includes isolated RNA molecules that inhibit expression of VDAC1 and/or VDAC2. In some embodiments, a first strand of the double-stranded RNA comprises a sequence selected from the following, and including about 14 to 25 nucleotides: 5'-CGGAAUAGCAGCCAAGUdTdT-3' (SEQ ID NO: 47) and 5'-CCCUGGAGUUGGAGGCUdTdT-3' (SEQ ID NO: 48).

The presently-disclosed subject matter further includes methods of screening candidate inhibitors to identify VDAC1 and/or VDAC2 inhibitors. In some embodiments, cell or cell line-based methods are used.

Inhibiting Caspase-8

In some embodiments, the presently-disclosed subject matter includes a method of protecting a cell, comprising: inhibiting caspase-8 of the cell. In some embodiments, the inhibiting caspase-8 comprises administering a caspase-8 inhibitor.

Examples of caspase-8 inhibitors that can be used in accordance with the presently-disclosed subject matter include, but are not limited to those set forth in Table F. As such, embodiments of the presently-disclosed subject matter can include administering a caspase 8 inhibitor set forth in Table F.

TABLE F

Examples of Caspase-8 Inhibitors

Z-IETD-FMK (BD Biosciences)
Ac-Ala-Ala-Val-Ala-Leu-Leu-Pro-Ala-Val-Leu-Leu-Ala-Leu-Leu-Ala-Pro-Ile-Glu-Thr-Asp-CHO (EMD Millipore)
Z-Ile-Glu(OMe)-Thr-Asp(OMe)-CH$_2$F (EMD Millipore)
Cellular fas-associated death domain-like interleukin-1-β-converting enzyme-inhibitory protein (L), i.e. c-FLIP(L), a.k.a. FLICE, a.k.a. MACH, a.k.a. Mch5

The presently-disclosed subject matter further includes compositions useful for inhibiting caspase-8. Such compositions include an inhibitor. As noted above, such inhibitors can be, for example, a nucleotide, a polypeptide, a small (chemical) molecule, etc. In some embodiments, a composition can include an isolated RNA molecule.

The presently-disclosed subject matter further includes methods of screening candidate inhibitors to identify caspase-8 inhibitors. In some embodiments, cell or cell line-based methods are used.

Inhibiting NFκB

In some embodiments, the presently-disclosed subject matter includes a method of protecting a cell, comprising: inhibiting NFκB of the cell. In some embodiments, the inhibiting NFκB comprises administering a caspase-8 inhibitor.

Examples of NFκB inhibitors that can be used in accordance with the presently-disclosed subject matter include, but are not limited to those set forth in Table G. As such, embodiments of the presently-disclosed subject matter can include administering a NFκB inhibitor set forth in Table G.

TABLE G

Examples of NFKB Inhibitors
Any one or more of the following NFKB inhibitors

Antioxidants that have been shown to inhibit activation of NF-kB

| | |
|---|---|
| a-Lipoic acid | Sen et al, 1998; Suzuki et al, 1992 |
| a-tocopherol | Islam et al, 1998 |
| Aged garlic extract (allicin) | Ide & Lau, 2001; Lang et al, 2004; Hasan et al, 2007 |
| 2-Amino-1-methyl-6-phenylimidazo[4,5-b]pyridine (PhIP) | Yun et al, 2005 |
| N-acetyldopamine dimers (from P. cicadae) | Xu et al, 2006 |
| Allopurinol | Gomez-Cabrera et al, 2006 |
| Anetholdithiolthione | Sen et al, 1996 |
| Apocynin | Barbieri et al, 2004 |
| Apple juice/extracts | Shi & Jiang, 2002; Daviset al, 2006; Jung et al, 2009 |
| Aretemsia p7F (5,6,3',5'-tetramethoxy 7,4'-hydroxyflavone) | Lee et al, 2004 |
| Astaxanthin | Lee et al, 2003 |
| Autumn olive extracts; olive leaf extracts | Wang et al, 2007; Wanget al, 2008 |
| Avenanthramides (from oats) | Guo et al, 2007; Sur et al, 2008 |
| Bamboo culm extract | Lee et al, 2008 |
| Benidipine | Matsubara & Hazegawa, 2004 |
| bis-eugenol | Murakami et al, 2003 |
| Bruguiera gymnorrhiza compounds | Homhual et al, 2006 |
| Butylated hydroxyanisole (BHA) | Israel et al, 1992; Schulze-Osthoff et al, 1993 |
| Cepharanthine | Okamoto et al, 1994;Tamatani et al, 2007 |
| Caffeic Acid Phenethyl Ester (3,4-dihydroxycinnamic acid, CAPE) | Natarajan et al, 1996;Nagasaka et al, 2007 |
| Carnosol | Lo et al, 2002; Huang et al, 2005 |
| beta-Carotene | Bai et al, 2005;Guruvayoorappan & Kuttan, 2007 |
| Carvedilol | Yang et al, 2003 |
| Catechol Derivatives | Suzuki & Packer, 1994;Zheng et al, 2008 |
| Centaurea L (Asteraceae) extracts | Karamenderes et al, 2007 |
| Chalcone | Liu et al, 2007 |
| Chlorogenic acid | Feng et al, 2005 |
| 5-chloroacetyl-2-amnio-1,3-selenazoles | Nam et al, 2008 |
| Cholestin | Lin et al, 2007 |
| Chroman-2-carboxylic acid N-substituted phenylamides | Kwak et al, 2008 |
| Cocoa polyphenols | Lee et al, 2006 |
| Coffee extract (3-methyl-1,2-cyclopentanedione) | Chung et al, 2007 |
| Crataegus pinnatifida polyphenols | Kao et al, 2007 |

TABLE G-continued

Examples of NFKB Inhibitors
Any one or more of the following NFKB inhibitors

| | |
|---|---|
| Curcumin (Diferulolylmethane); dimethoxycurcumin; EF24 analog | Singh & Aggarwal, 1995;Pae et al, 2008; Kasinskiet al, 2008 |
| Dehydroepiandrosterone (DHEA) and DHEA-sulfate (DHEAS) | Iwasaki et al, 2004; Liu et al, 2005 |
| Dibenzylbutyrolactone lignans | Cho et al, 2002 |
| Diethyldithiocarbamate (DDC) | Schreck et al, 1992 |
| Diferoxamine | Sappey et al, 1995;Schreck et al, 1992 |
| Dihydroisoeugenol; isoeugenol; epoxypseudoisoeugenol-2-methyl butyrate | Murakami et al, 1995Tark et al, 2007; Ma et al, 2008 |
| Dihydrolipoic Acid | Suzuki et al, 1992, 1995 |
| Dilazep + fenofibric acid | Sonoki et al, 2003; Yanget al, 2005 |
| Dimethyldithiocarbamates (DMDTC) | Pyatt et al, 1998 |
| Dimethylsulfoxide (DMSO) | Kelly et al, 1994 |
| Disulfiram | Schreck et al, 1992 |
| Ebselen | Schreck et al, 1992 |
| Edaravone | Kokura et al, 2005; Ariiet al, 2007; Yoshida et al, 2007 |
| EPC-K1 (phosphodiester compound of vitamin E and vitamin C) | Hirano et al, 1998 |
| Epigallocatechin-3-gallate (EGCG; green tea polyphenols) | Lin & Lin, 1997; Yang et al,1998; Hou et al, 2007; Jiang et al, 2012 |
| Ergothioneine | Rahman et al, 2003 |
| Ethyl Pyruvate (Glutathione depletion) | Song et al, 2004; Tsung et al, 2005; Jimenez-Lopezet al, 2008 |
| Ethylene Glycol Tetraacetic Acid (EGTA) | Janssen et al, 1999 |
| Eupatilin | Lee et al, 2008 |
| Exercise | Goto et al, 2007 |
| Fisetin | Park et al, 2006; Sung et al, 2007 |
| Flavonoids (Cmtaegus; Boerhaavia diffusa root; xanthohumol; Eupatorium arnottianum; genistein; kaempferol; quercetin, daidzein; flavone; isorhamnetin; naringenin; pelargonidin; finestin; Sophora flavescens; Seabuckthorn fruit berry) | Zhang et al, 2004; Chenet al, 2004; Pandey et al, 2005; Albini et al, 2005;Colgate et al, 2006;Clavin et al, 2007; Hamalainen et al, 2008;Zheng et al, 2008; Junget al, 2008; Mishra et al, 2008 |
| Flavonoid-7-glycosides (chamomile flowers extract) | Bulgari et al, 2012 |
| Folic acid | Au-Yeung et al, 2006 |
| Gamma-glutamylcysteine synthetase (gamma-GCS) | Manna et al, 1999 |
| Ganoderma lucidum polysaccharides | Zhang et al, 2003; Ho et al, 2007 |
| Garcinol (from extract of Garcinia indica fruit rind) | Liao et al, 2004 |
| Ginkgo biloba extract | Chen et al, 2003 |
| Glutathione | Cho et al, 1998; Schrecket al, 1992; Wang et al, 2007 |
| Guaiacol (2-methoxyphenol) | Murakami et al, 2007 |
| Hematein | Choi et al, 2003 |
| Hinokitiol | Byeon et al, 2008 |
| HMCO5 herbal extract | Kim et al, 2007 |
| Hydroquinone | Pyatt et al, 1998; Yang et al, 2006 |
| 23-hydroxyursolic acid | Shin et al, 2004 |
| IRFI 042 (Vitamin E-like compound) | Altavilla et al, 2001 |
| Iron tetrakis | Kang et al, 2001 |
| Isosteviol | Xu et al, 2008 |
| Isovitexin | Lin et al, 2005 |
| Isoliquiritigenin | Kumar et al, 2007; Kimet al, 2008; Kim et al, 2008 |
| Justicia gendarussa root extract | Kumar et al, 2011 |
| Kallistatin | Shen et al, 2008 |
| Kangen-karyu extract | Satoh et al, 2005;Yokozawa et al, 2007 |
| L-cysteine | Mihm et al, 1991 |
| Lacidipine | Cominacini et al, 1997 |
| Lazaroids | Marubayashi et al, 2002 |
| Ligonberries | Wang et al, 2005 |
| Lupeol | Saleem et al, 2004; Lee et al, 2007 |
| Lutein | Kim et al, 2008 |
| Magnolol | Chen et al, 2002; Ou et al, 2006; Kim et al, 2007 |
| Maltol | Yang et al, 2006 |
| Manganese superoxide dismutase (Mn-SOD) | Manna et al, 1998 |
| Extract of the stem bark of Mangifera indica L. | Leiro et al, 2004; Garridoet al, 2005 |
| Melatonin | Gilad et al, 1998; Mohanet al, 1995; Li et al, 2005 |
| 21 (alpha, beta)-methylmelianodiol | Zhou et al, 2007 |
| Mulberry anthocyanins | Chen et al, 2006 |
| N-acetyl-L-cysteine (NAC) | Schreck et al, 1991 |
| Nacyselyn (NAL) | Antonicelli et al, 2002 |
| Nordihydroguaiaritic acid (NDGA) | Brennan & O'Neill, 1998;Israel et al,1992; Schulze-Osthoff et al, 1993; Staalet al, 1993 |
| Ochnaflavone | Suh et al, 2006 |
| Onion extract (2,3-dihydro-3,5-dihydroxy-6-methyl-4H-pyranone) | Ban et al, 2007; Tang et al, 2008 |
| Orthophenanthroline | Schreck et al, 1992 |
| N-(3-oxo-dodecanoyl) homoserine lactone | Kravchenko et al, 2008 |
| Paricalcitol | Tan et al, 2008 |
| Phenolic antioxidants (Hydroquinone and tert-butyl hydroquinone) | Ma et al, 2003 |
| Olive oil phenols (extra-virgin olive oil) | Sangiovanni et al, 2012 |
| alkenylphenols from Piper obliquum | Valdivia et al, 2008 |

TABLE G-continued

Examples of NFKB Inhibitors
Any one or more of the following NFKB inhibitors

| | |
|---|---|
| alpha-phenyl-n-tert-butyl-nitron (PBN) | Kotake et al, 1998;Lin et al, 2006 |
| Phenylarsine oxide (PAO, tyrosine phosphatase inhibitor) | Arbault et al, 1998 |
| Phyllanthus urinaria | Chularojmontri et al, 2005; Shen et al, 2007 |
| Phytosteryl ferulates (rice bran) | Islam et al, 2008; Jung et al, 2008 |
| Piper longum Linn. extract | Singh et al, 2007 |
| Pitavastatin | Tounai et al, 2007; Wang& Kitajima, 2007 |
| Prodelphinidin B2 3, 3' di-O-gallate | Hou et al, 2007 |
| Pterostilbene | Cichocki et al, 2008; Pan et al, 2009 |
| Pyrrolinedithiocarbamate (PDTC) | Schreck et al, 1992 |
| Quercetin | Musonda & Chipman, 1998; Shih et al, 2004;Garcia-Mediavilla et al, 2006; Ruiz et al, 2007;Min et al, 2007; Kim et al, 2007 |
| Red orange extract | Cimini et al, 2008 |
| Red wine | Blanco-Colio et al, 2000;Cui & He, 2004 |
| Ref-1 (redox factor 1) | Ozaki et al, 2002 |
| Rg(3), a ginseng derivative | Keum et al, 2003 |
| Rotenone | Schulze-Osthoff et al, 1993 |
| Roxithromycin | Ueno et al, 2005; Ou et al, 2008 |
| Rutin | Kyung et al, 2008 |
| S-allyl-cysteine (SAC, garlic compound) | Geng et al, 1997 |
| Salogaviolide (Centaurea ainetensis) | Ghantous et al, 2008 |
| Sauchinone | Lee et al, 2003; Hwang et al, 2003 |
| Schisandrin B | Giridharan et all, 2011 |
| Silybin | Gazak et al, 2007 |
| Spironolactone | Han et al, 2006 |
| Strawberry extracts | Wang et al, 2005 |
| Sulfuretin | Lee et al, 2012 |
| Taxifolin | Wang et al, 2005 |
| Tempol | Cuzzocrea et al, 2004 |
| Tepoxaline (5-(4-chlorophenyl)-N-hydroxy-(4-methoxyphenyl)-N-methyl-1H-pyrazole-3-propanamide) | Kazmi et al, 1995; Ritchie et al, 1995 |
| Thio avarol derivatives | Amigo et al, 2007; Amigo et al, 2008 |
| Thymoquinone | El Gazzar et al, 2007;1Sethi et al, 2008 |
| Tocotrienol (palm oil) | Wu et al, 2008 |
| 8-(Tosylamino)quinoline | Jung et al, 2012 |
| Tomato peel polysaccharide | De Stefano et al, 2007 |
| UDN glycoprotein (Ulmus davidiana Nakai) Lee & Lim, 2007 | |
| Vaccinium stamineum (deerberry) extract | Wang et al, 2007 |
| Vanillin (2-hydroxy-3-methoxybenzaldehyde) | Murakami et al, 2007 |
| Vitamin C | Staal et al, 1993; Son et al, 2004 |
| Vitamin B6 | Yanaka et al, 2005 |
| Vitamin E and derivatives Glauert, 2007 | Suzuki & Packer, 1993;Ekstrand-Hammarstrom et al, 2007; |
| a-torphryl succinate | Staal et al, 1993; Suzuki & Packer, 1993 |
| a-torphryl acetate | Suzuki & Packer, 1993 |
| PMC (2,2,5,7,8-pentamethyl-6-hydroxychromane) | Suzuki & Packer, 1993 |
| Yakuchinone A and B | Chun et al, 2002 |
| Proteasome and proteases inhibitors that inhibit Rel/NF-kB | |
| Proteasome inhibitors | |
| Peptide Aldehydes: | Palombella et al, 1994; Grisham et al, 1999; Jobin et al, 1998 |
| ALLnL (N-acetyl-leucinyl-leucynil-norleucynal,MG101) | |
| LLM (N-acetyl-leucinyl-leucynil-methional) | |
| Z-LLnV (carbobenzoxyl-leucinyl-leucynil-norvalinal,MG115) | |
| Z-LLL (carbobenzoxyl-leucinyl-leucynil-leucynal, MG132) | |
| MG262 | Pujois et al, 2012 |
| Lactacystine, beta-lactone | Fenteany & Schreiber, 1998; Grisham et al, 1999 |
| Boronic Acid Peptide | Grisham et al, 1999; Iqbal et al, 1995 |
| Dithiocarbamate complexes with metals | Cvek & Dvorak, 2007 |
| CEP-18770 | Piva et al, 2007 |
| Ubiquitin Ligase Inhibitors | Yaron et al, 1997 |
| PS-341 (Bortezomib) | Adams, 2004 |
| Salinosporamide A (1, NPI-0052) | Macherla et al, 2005; Ahn et al, 2007 |
| Cyclosporin A McCaffrey et al, 1994;Meyer et al, 1997; Wechsler et al, 1994 | Frantz et al, 1994; Kunz et al, 1995; Marienfeld et al, 1997; |
| FK506 (Tacrolimus) | Okamoto et al, 1994; Venkataraman et al, 1995 |
| Deoxyspergualin | Tepper et al, 1995 |
| Disulfiram | Lovborg et al, 2005 |
| PT-110 | Momose et al, 2007 |
| Protease inhibitors | |
| APNE (N-acetyl-DL-phenylalanine-b-naphthylester) | Higuchi et al, 1995 |
| B IEE (N-benzoyl L-tyrosine-ethylester) | Rossi et al, 1998 |
| DCIC (3,4-dichloroisocoumarin) | D'Acquisto et al, 1998 |
| DFP (diisopropyl fluorophosphate) | |
| TPCK (N-a-tosyl-L-phenylalanine chloromethyl ketone) | |

TABLE G-continued

Examples of NFKB Inhibitors
Any one or more of the following NFKB inhibitors

TLCK (N-a-tosyl-L-lysine chloromethyl ketone)
IkBa phosphorylation and/or degradation inhibitors

| Molecule | Point of Inhibition | References |
|---|---|---|
| Desloratadine; diphenhydramine Histamine H1 receptor | Wu et al, 2004; Scadding, 2005; | Roumestan et al, 2008 |
| Bikunin | LPS receptor agonists | Kobayashi, 2006; Kanayama et al, 2007 |
| Ron Tyrosine kinase receptor | Suppresses TNF production | Lentsch et al, 2007 |
| TAK-242 | TLR4 intracellular domain | Kawamoto et al, 2008 |
| Salmeterol, fluticasone propionate | beta2 agonists | Baouz et al, 2005 |
| CPU0213 | Endothelin receptor antagonist | He et al, 2006 |
| Doxazosin | alpha1-adrenergic receptor antagonist | Hui et al, 2007 |
| Erbin overexpression | NOD2 inhibitor | McDonald et al, 2005 |
| Protein-bound polysaccharide from basidiomycetes | LPS-CD14 interaction | Asai et al 2005 |
| Anti-CD146 antibody AA98 | upstream of IKK | Bu et al, 2006 |
| Calagualine (fern derivative) | upstream of IKK (TRAF2-NIK) | Manna et al, 2003 |
| NS3/4A (HCV protease) | upstream of IKK | Karayiannis, 2005 |
| golli BG21 (product of myelin basic protein) | upstream of IKK (PKC) | Feng et al 2004 |
| NPM-ALK oncoprotein | Traf2 inhibition | Horie et al, 2004 |
| NS5A (Hepatitis C virus) | Traf2 inhibition | Park et al, 2002 |
| LY29 and LY30 | PI3 Kinase inhibitors | Choi et al, 2004 |
| Shiga toxin (Enterohemorrhagic E coli) | PI3 Kinase inhibitor | Gobert et al 2007 |
| Evodiamine (Evodiae Fructus component) | AKT-IKK interaction | Takada et al 2005 |
| Rituximab (anti-CD20 antibody) | up-regulates Raf-1 kinase inhibitor | Jazirehi et al, 2005 |
| Kinase suppressor of ras (KSR2) | MEKK3 inhibitor | Channavajhala et al, 2005 |
| Cholecystokinin ocatpeptide (CCK-8)p38 kinase | | Li et al, 2007 |
| M2L (Vaccinia virus) | ERK2 inhibitor | Gedey et al, 2006; |
| Pefabloc (serine protease inhibitor)upstream of IKK | Tando et al, 2002 | Hinthong et al, 2008 |
| Rocaglamides (Aglaia derivatives) | upstream of IKK | Baumann et al, 2002 |
| Ymer | Binds to Ub-RIP | Bohgaki et al, 2007 |
| Epoxyquinol B | TAK1 crosslinker | Kamiyama et al, 2008 |
| Betaine | NIK/IKK | Go et al, 2004, 2007 |
| TNAP | NIK | Hu et al, 2005 |
| Selected peptides | NEMO binding to Ub | Wyler et al, 2007 |
| Biochanin | upstream of IKK/ phosphorylates of IκBα | Manna et al, 2012 |
| Desflurane | IKK complex formation with TNF-Rl | Li et al, 2008 |
| Geldanamycin | IKK complex formation | Chen et al, 2002 |
| Grape seed proanthocyanidins | IKKa activity | Mantena & Katiyar, 2006; Sharma et al, 2007; Cheng et al, 2007; Xu et al, 2008 |
| Laretia acaulis azorellane diterpenoids | IKKa activity | Borquez et al, 2007 |
| MC160 (Molluscum contagiosum virus) | IKKa activity | Nichols & Shisler, 2006 |
| NS5B (Hepatitis C protein) | IKKa activity | Choi et al, 2006 |
| Pomegranate fruit extract | IKKa activity | Afaq et al, 2004; Khan et al, 2006 |
| Tetrandine (plant alkaloid) | IKKa activity | Ho et al, 2004; Xue et al, 2008; Lin et al 2008 |
| BMS-345541 (4(2'-Aminoethyl)amino-1,8-dimethylimidazo(1,2-a) quinoxaline) and 4-amino derivatives IKKa and IKKb kinase activity | Burke et al, 2002; Yang et al, 2006; | Beaulieu et al, 2006 |
| 1-O-acetylbritannilactone | IKKb activity | Liu et al, 2007 |
| 2-amino-3-cyano-4-aryl-6-(2-hydroxy-phenybpyridine derivatives | IKKb activity | Murata et al, 2003, 2004, 2004 |
| Acrolein | IKKb activity/p50 DNA binding Vallacchi et al, 2005; | Lambert et al 2007 |
| Anandamide | IKKb activity | Sancho et al, 2003 |
| AS602868 | IKKb activity | Frelin et al, 2003: Griessinger et al, 2007 |
| benzoxathiole(6,6-dimethyl-2-(phenylimino)-6,7-dihydro-5H-benzo-[1,3]oxathio1-4-one (and its analogs) | IKKb activity | Venkateswararao et al, 2012 |
| Cobrotoxin | IKKb activity/p50 DNA binding Park et al, 2005 | |
| Core protein (Hepatitis C) | IKKb activity | Joo et al, 2005; Shrivastava et al, 1998 |
| 1-[2-cyano-3,12-dioxooleana-1,9(11)-dien-28-oyl]imidazole | IKKb activity | Yore et al, 2006 |
| Dihydroxyphenylethanol | IKKb activity | Guichard et al, 2006 |
| Heibimycin A | IKKb activity | Iwasaki et al, 1992; Mahon & O'Neill, 1995; Ogino et al, 2004 |
| Inhibitor 22 | IKKb activity | Baxter et al, 2004 |
| Isorhapontigenin | IKKb activity | Li et al, 2005 |
| Manumycin A | IKKb activity | Bernier et al, 2005; Frassanito et al, 2005 |
| 6-methyl-2-propolyimino-6,7-dihydro-5H-benzo[1,3]oxathiol-4-one | IKKb | Kim et al, 2008 |

TABLE G-continued

Examples of NFKB Inhibitors
Any one or more of the following NFKB inhibitors

| | | |
|---|---|---|
| MLB120 (small molecule) | IKKb activity | Nagashima et al, 2006 |
| Naphthopyrones (6-methoxycomaparvin and 6-methooxycomaparvin 5-methyl ether) | IKKb activity | Fulmer et al, 2008 |
| Novel Inhibitor | IKKb activity | Kamon et al, 2004 |
| vIRF3 (KSHV) | IKKb activity | Seo et al, 2004 |
| Nitric oxide | IKKb activity/IkB phosphorylation | Katsuyama et al, 1998; Matthews et al, 1996; Spieker & Liao, 1999; Reynaert et al, 2004 |
| SC-514 (small molecule) | IKKb activity | Kishore et al, 2003 |
| Thienopyridine | IKKb activity | Morwick et al, 2006 |
| Acetyl-boswellic acids | IKK activity | Syrovets et al, 2004, 2005 |
| Amino-pyrimidine derivative | IKK activity | Karin et al, 2004 |
| Benzoimidazole derivative | IKK activity | Karin et al, 2004 |
| BMS-345541 | IKK activity | Burke et al, 2003 |
| Butein | IKKb activity | Pandey et al, 2007 |
| Beta-carboline | IKK activity | Yoon et al, 2005 |
| CYL-19s and CYL-26z, two synthetic alpha-methylene-gamma-butyrolactone derivatives | IKK activity | Huang et al, 2004 |
| ACHP (2-amino-6-[2-(cyclopropylmethoxy)-6-hydroxyphenyl]-4-piperidin-4-yl nicotinonitrile | IKKb activity (ATP analog) | Sanda et al, 2006 |
| Berberine | IKKb activity | Hu et al, 2007; Yi et al, 2008; Pandey et al 2008 |
| Compound A | IKKb activity (ATP analog) | Ziegelbauer et al, 2005 |
| Flavopiridol | IKK activity and RelA phosphor. | Takada & Aggarwal, 2003 |
| Cyclopentones | IKKb activity | Bickley et al, 2004 |
| Dehydroascorbic acid (Vitamin C) | IKKb activity | Carcamo et al, 2004 |
| Gossypyin or Gossypium extracts | IKKb activity | Kunnumakkara et al, 2007; Ji et al, 2008 |
| M protein (SARS-Cornonavirus protein) | IKKb activity | Fang et al, 2007 |
| IMD-0354 | IKKb activity | Tanaka et al, 2004, 2006; Inayama et al 2006 |
| Jesterone dimer | IKKb activity; DNA binding | Liang et al, 2003, 2006 |
| KINK-1 | IKKb activity | Schon et al, 2008 |
| LCY-2-CHO | IKKb activity | Ho et al, 2007 |
| Prolyl hydroxylase-1 | IKKb activity | Cummins et al, 2006 |
| Naphthopyrones (Echinoderm Comanthus parvicirrus) | IKKb activity | Folmer et al, 2007 |
| Neuropeptides CGRP, PACAP and VIP | IKKb activity | Ding et al, 2007 |
| PS-1145 (MLN1145) | IKKb activity | Hideshima et al, 2002 |
| 2-[(aminocarbonyl)amino]-5-(4-fluorophenyl)-3-thiophenecarboxamides (TPCA-1) | IKKb activity | Bonafoux et al, 2005; Podolin et al, 2005 |
| 1'-Acetoxychavicol acetate (Languas galanga) | IKK activity | Ichikawa et al, 2005; Ito et al, 2005 |
| 17-Acetoxyjolkinolide B | IKK activity | Yan et al, 2008 |
| Acute alcohol exposure | IKK activity | Mandrekar et al, 2007 |
| Anacardic acid (6-nonadecyl-salicylic acid) | IKK activity | Sung et al, 2008 |
| Apigenin (plant flavinoid) | IKK activity | Shukla & Gupta, 2004; Yoon et al, 2006 |
| Asiatic acid | IKK activity | Yun et al, 2008 |
| Cardamomin | IKK activity | Lee et al, 2005 |
| CDDO-Me (synthetic triterpenoid) | IKK activity | Shishodia et al, 2006 |
| CHS 828 (anticancer drug) | IKK activity | Olsen et al, 2004 |
| CIVIL-1 | IKK activity | Mo et al, 2006 |
| Compound 5 (Uredio-thiophenecarboxamide derivative) | IKK activity | Roshak et al, 2002 |
| CT20126 | IKK activity/NIK | Lee et al, 2008 |
| Diaylpyridine derivative | IKK activity | Murata et al, 2003 |
| 3,4-dihydroxybenzalacetone (from Chaga) | IKK activity | Sung et al, 2008 |
| Diosgenin | IKK activity | Shishodia & Aggarwal, 2005; Liagre et al 2005 |
| E3-14.7K (Adenovirus) | IKK activity | Li et al, 1999 |
| E3-10.4K/14.5K (Adenovirus) | IKK activity | Friedman & Horwitz, 2002 |
| E7 (human papillomavirus) | IKK activity | Spitkovsky et al, 2002 |
| Furonaphthoquinone | IKK activity | Shin et al, 2006 |
| 3-Formylchromone | IKKb activity/p65 DNA binding | Yadav et al, 2011 |
| Guggulsterone | IKK activity | Ichikawa & Aggarwal, 2006; Deng, 2007; Lv et al, 2008; Lee et al, 2008 |
| HB-EGF (Heparin-binding epidermal growth factor-like growth factor) | IKK activity | Mehta & Besner, 2003 |
| Falcarindol | IKK activity | Shiao et al, 2005 |
| Hammerhead ribozyme to IKKa/b | IKK activity | Yang et al, 2007 |
| Hepatocyte growth factor | IKK activity | Min et al, 2005; Gong et al, 2006 |
| Honokiol | IKK activity | Tse et al, 2005; Munroe et al, 2007 |
| Humulone | IKK activity | Lee et al, 2007 |
| Hypoestoxide | IKK activity | Ojo-Amaize et al, 2001 |
| Indolecarboxamide derivative | IKK activity | Karin et al, 2004 |
| Labdane diterpenoids | IKK activity | Giron et al, 2008 |

TABLE G-continued

Examples of NFKB Inhibitors
Any one or more of the following NFKB inhibitors

| | | |
|---|---|---|
| LF15-0195 (analog of 15-deoxyspergualine) | IKK activity | Yang et al, 2003 |
| gamma-mangostin (from Garcinia mangostana) | IKK activity | Nakatani et al, 2004 |
| Garcinone B | IKK activity | Yamakuni et al, 2005 |
| (Amino)imidazolylcalboxaldehyde derivative | IKK activity | Karin et al, 2004 |
| Imidazolylquinoline-carboxaldehyde derivative | IKK activity | Karin et al, 2004 |
| Kahweol | IKK activity | Kim et al, 2004 |
| Kava (Piper methysticum) derivatives | IKK activity | Folmer et al, 2006 |
| Lead | IKK activity | Xu et al, 2006 |
| Marasmius oreades liquid extract | IKK activity | Petrova et al, 2008 |
| Menatetrenone (vitamin K2 analogue) | IKK activity | Ozaki et al, 2007 |
| Metformin | IKK activity | Huang et al, 2008 |
| Mild hypothermia | IKK activity | Han et al, 2003 |
| ML 120B | IKK activity | Catley et al, 2006 |
| Morin (3,5,7,2',4'-Pentahydroxyflavone) | IKK activity | Manna et al, 2007 |
| Morusin | IKK activity | Lee et al, 2008 |
| MX781 (retinoid antagonist) | IKK activity | Bayon et al, 2003 |
| N-acetylcysteine | IKK activity | Oka et al, 2000 |
| Nitrosylcobalamin (vitamin B12 analog) | IKK activity | Chawla-Sarkar et al 2003 |
| NSAIDs | IKK activity | Takada et al, 2004 |
| Hepatits C virus NS5B | IKK activity | Choi et al, 2006 |
| PAN1 (aka NALP2 or PYPAF2) | IKK activity | Bruey et al, 2004 |
| Pectin (citrus) | IKK activity | Chen et al, 2006 |
| Pinitol | IKK activity | Sethi et al, 2008 |
| PMX464 | IKK activity | Callister et al, 2008 |
| Pyrazolo[4,3-c]quinoline derivative | IKK activity | Karin et al, 2004 |
| Pyridooxazinone derivative | IKK activity | Karin et al, 2004 |
| N-(4-hydroxyphenyl) retinamide | IKK activity | Shishodia et al, 2005; Kuefer et al, 2007 |
| Scytonemin | IKK activity | Stevenson et al, 2002 |
| Semecarpus anacardiu extract | IKK activity | Singh et al, 2006 |
| SPC-839 | IKK activity | Palanki et al, 2002 |
| Sulforaphane and phenylisothiocyanate | IKK activity | Xu et al, 2005; Murakami et al, 2007; Liu et al, 2008: Hayes et al, 2008 |
| Survanta (Surfactant product) | IKK activity | Raychaudhuri et al, 2003 |
| Torque Teno virus ORF2 | IKK activity | Zheng et al, 2007 |
| Piceatannol | IKK activity | Islam et al, 2004 |
| Plumbagin (5-hydroxy-2-methyl-1,4-naphthoquinone) | IKK activity | Sandur et al, 2006 |
| IKKb peptide to NEMO binding domain | IKK-NEMO interaction | May et al. 2000 |
| NEMO CC2-LZ peptide | NEMO oligomerization | Agou et al, 2004 |
| AGRO100 (G-quadraplex oligodeoxynucleotide) | NEMO binding | Girvan et al, 2006 |
| PTEN (tumor suppressor) | Activation of IKK | Gustin et al, 2001 |
| Theaflavin (black tea component) | Activation of IKK | Aneja et al, 2004; Ukil et al, 2006; Kalra et al, 2007 |
| Tilianin | Activation of IKK | Nam et al, 2005 |
| Withanolides | Activation of IKK | Ichikawa et al, 2006 |
| Zerumbone | Activation of IKK | Takada et al, 2005 |
| Silibinin | IKKa activity; nuclear translocation | Dhanalakshmi et al, 2002; Singh et al, 2004; Min et al, 2007 |
| Sulfasalazine | IKKa and IKKb kinase activity | Wahl et al, 1998: Weber et al, 2000 |
| Sulfasalazine analogs | IKK kinase activity | Habens et al, 2005 |
| Quercetin | IKK activity | Peet & Li, 1999 |
| Rosmarinic acid | IKK activity | Lee et al, 2006 |
| Staurosporine | IKK activity | Peet & Li, 1999 |
| gamma-Tocotrienol | IKK activity | Shah & Sylvester, 2005; Ahn et al, 2006 |
| Wedelolactone | IKK activity | Kobori et al, 2003 |
| Betulinic acid | IKKa activity and p65 phosphorylation | Takada & Aggarwal, 2003; Rabi et al, 2008 |
| Ursolic acid | IKKa activity and p65 phosphorylation | Shishodia et al, 2003; Manu & Kuttan, 2008 |
| Thalidomide (and thalidomideanalogs) | IKK activity | Keifer et al, 2001; Ge et al, 2006; Carcache de-Blanco et al, 2007 |

TABLE G-continued

Examples of NFKB Inhibitors
Any one or more of the following NFKB inhibitors

| | | |
|---|---|---|
| Salubrinal | IKK activity/degradation | Huang et al, 2011 |
| Fas-associated factor-1 | IKK assembly | Park et al, 2007 |
| Interleukin-10 | Reduced IKKa and IKKb expression | Tabary et al, 2003 |
| MC160 (molluscum contagiosum virus) | Reduced IKKa expression | Nichols & Shisler, 2006 |
| Monochloramine and glycine chloramine (NH2C1) | Oxidizes IkB | Kim et al, 2005; Midwinter et al, 2006 |
| GS143 | Blocks IkB ubiquitylation | Nakajima et al, 2008; Hirose et al, 2008 |
| Salmonella Secreted Factor L | Blocks IkB ubiquitylation | Le Negrate et al, 2008 |
| Anethole | Phosphorylation | Chainy et al, 2000 |
| Anti-thrombin III | Phosphorylation | Oelschlager et al, 2002 |
| Artemisia vestita | Phosphorylation | Sun et al, 2006 |
| Aspirin, sodium salicylate | Phosphorylation, IKKbeta | Frantz & O'Neill, 1995; Kopp & Ghosh, 1994; Yin et al, 1998 |
| Azidothymidine (AZT) | Phosphorylation | Ghosh et al, 2003; Kurokawa et al, 2005 |
| Baoganning | Phosphorylation | Tan et al, 2005 |
| BAY-11-7082 (E3((4-methylphenyl)-sulfonyl)-2-propenenitrile) Phosphorylation | | Pierce et al, 1997 |
| BAY-117083 (E3((4-t-butylphenyl)-sulfonyl)-2-propenenitrile) Phosphorylation | | Pierce et al, 1997 |
| Benzyl isothiocyanate | Phosphorylation | Srivastava & Singh, 2004 |
| Black raspberry extracts (cyanidin 3-O-glucoside, cyanidin 3-O-(2(G)-xylosylrutinoside), cyanidin 3-O-(2(G)-xylosylrutinoside), cyanidin 3-O-rutinoside) | Phosphorylation | Huang et al, 2002; Hecht et al, 2006 |
| Buddlejasaponin IV | Phosphorylation | Won et al, 2006 |
| Cacospongionolide B | Phosphorylation | Posadas et al, 2003 |
| Calagualine | Phosphorylation | Manna et al, 2003 |
| Carbon monoxide | Phosphorylation | Sarady et al, 2002 |
| Carboplatin | Phosphorylation | Singh & Bhat, 2004 |
| Cardamonin | Phosphorylation | Israf et al, 2006 |
| Chorionic gonadotropin | Phosphorylation | Manna et al, 2000 |
| Cordycepin | Phosphorylation | Kim et al, 2006; Huang et al., 2007 |
| Crassocephalum rabens galactolipid | Phosphorylation | Hou et al., 2007 |
| Cycloepoxydon; 1-hydroxy-2-hydroxymethyl-3-pent-1-enylbenzene | Phosphorylation | Gehrt et al, 1998 |
| Cytomegalovirus | Phosphorylation | Jarvis et al, 2006 |
| Decursin | Phosphorylation | Kim et al, 2006 |
| Delphinidin | Phosphorylation | Syed et al, 2008 |
| Dexanabinol | Phosphorylation | Juttler et al, 2004 |
| Digitoxin | Phosphorylation | Srivastava et al, 2004; Jagielska et al, 2009 |
| Dihydrotestosterone | Phosphorylation | Xu et al, 2011 |
| Diterpenes (synthetic) | Phosphorylation | Chao et al, 2005 |
| Docosahexaenoic acid | Phosphorylation | Chen et al, 2005; Zand et al, 2008 |
| Entamoeba histolytica | Phosphorylation | Kammanadiminti & Chadee, 2006 |
| Extensively oxidized low density lipoprotein (ox-LDL), 4-Hydroxynonenal (HNE) | Phosphorylation | Brand et al, 1997; Page et al, 1999 |
| FBD | Phosphorylation | Lin et al, 2008 |
| FHIT (Fragile histidine triad protein) | Phosphorylation | Nakagawa & Akao, 2006 |
| Fructus Ligustrum lucidi | Phosphorylation | An et al, 2007 |
| Gabexate mesilate | Phosphorylation | Uchiba et al, 2003 |
| [6]-gingerol; casparol | Phosphorylation | Kim et al, 2005; Aktan et al, 2006; Ishiguro et al, 2007 |
| Gleditsia sinensis thorns extract | Phosphorylation | Ha et al, 2008 |
| Gleevec (Imatanib) | Phosphorylation | Wolf et al, 2005 |
| Glossogyne tenuifolia | Phosphorylation | Wu et al, 2004; Ha et al, 2006 |
| Guggulsterone | Phosphorylation | Shishodia & Aggarwal, 2004 |
| 4-hydroxy-3,6,7,8,3',4'-hexamethoxyflavone | Phosphorylation | Lai et al, 2007 |
| Hydroquinone | Phosphorylation | Kerzic et al, 2003 |
| Ibuprofen | Phosphorylation | Palayoor et al, 1998 |
| Indirubin-3'-oxime | Phosphorylation | Mak et al, 2004 |
| Inonotus obliquus ethanol extract | Phosphorylation | Kim et al, 2007 |
| Interferon-alpha | Phosphorylation | Manna et al, 2000 |
| Inhaled isobutyl nitrite | Phosphorylation | Ponnappan et al, 2004 |
| Kaempferol | Phosphorylation | Garcia-Mediavilla et al, 2006; Kim et al 2007 |
| Kushen flavonoids and kurarinone | Phosphorylation | Han et al, 2006 |
| Licorce extracts | Phosphorylation | Kim et al, 2006: Kwon et al, 2007 |
| Melatonin | Phosphorylation | Alonso et al, 2006; Tamura et al, 2009 |

TABLE G-continued

Examples of NFKB Inhibitors
Any one or more of the following NFKB inhibitors

| | | |
|---|---|---|
| Marine natural products (several) | IKKb/proteasome | Folmer et al, 2009 |
| Methotrexate | Phosphorylation | Majumdar & Aggarwal, 2001; Yozai et al 2005 |
| Monochloramine | Phosphorylation | Omori et al, 2002 |
| Nafamostat mesilate | Phosphorylation | Noguchi et al, 2003 |
| Obovatol | Phosphorylation | Lee et al, 2008 |
| Oleandrin | Phosphorylation | Manna et al, 2000; Sreeivasan et al, 2003 |
| Oleanolic acid (Aralia elata) | Phosphorylation | Suh et al, 2007 |
| Omega 3 fatty acids | Phosphorylation | Novak et al, 2003 |
| Panduratin A (from Kaempferia pandurata, Zingiberaceae) | Phosphorylation | Yun et al, 2003 |
| Petrosaspongiolide M | Phosphorylation | Posadas et al, 2003 |
| Pinosylvin | Phosphorylation | Lee et al, 2006 |
| Plagius flosculosus extract polyacetylene spiroketal | Phosphorylation | Calzado et al, 2005 |
| Phytic acid (inositol hexakisphosphate) | Phosphorylation | Ferry et al, 2002 |
| Pomegranate fruit extract | Phosphorylation | Ahmed et al, 2005 |
| Prostaglandin A1 | Phosphorylation/IKK | Rossi et al, 1997, 2000 |
| Protocatechuic Aldehyde | Phosphorylation | Xu et al, 2011 |
| 20(S)-Protopanaxatriol (ginsenoside metabolite) | Phosphorylation | Oh et al, 2004; Lee et al, 2005 |
| Rengyolone | Phosphorylation | Kim et al, 2006 |
| Rottlerin | Phosphorylation | Kim et al, 2005; Torricelli et al, 2008 |
| Saikosaponin-d | Phosphorylation; Increased IkBLeung et al, 2005; | Dang et al, 2007 |
| Saline (low Na+istonic) | Phosphorylation | Tabary et al, 2003 |
| Salvia miltiorrhizae water-soluble extract | Phosphorylation | Kim et al, 2005 |
| Sanguinarine (pseudochelerythrine, 13-methyl-[1,3]-benzodioxolo-[5,6-c]-1,3-dioxolo-4,5phenanthridinium) | Phosphorylation | Chaturvedi et al, 1997 |
| Scoparone | Phosphorylation | Jang et al, 2005 |
| Sesaminol glucosides | Phosphorylation | Lee et al, 2006 |
| Shikonins | Phosphorylation | Nam et al, 2008 |
| Silymarin | Phosphorylation | Manna et al, 1999; Saliou et al, 1998 |
| Snake venom toxin (Vipera lebetina turanica) | Phosphorylation | Son et al, 2007 |
| SOCS1 | Phosphorylation | Kinlyo et al, 2002; Nakagawa et al, 2002 |
| Spilanthol | Phosphorylation | Wu et al, 2008 |
| Statins (several) | Phosphorylation | Hilgendorff et al, 2003; Han et al, 2004; Planavila et al, 2005 |
| Sulindac | IKK/Phosphorylation | Yamamato et al, 1999 |
| THI 52 (1-naphthylethyl-6,7-dihydroxy-1,2,3,4-tetrahydroisoquinoline) | Phosphorylation | Kang et al, 2003 |
| 1,2,4-thiadiazolidine derivatives | Phosphorylation | Manna et al, 2004 |
| Tomatidine | Phosphorylation | Chiu & Lin, 2008 |
| Vesnarinone | Phosphorylation | Manna & Aggarwal, 2000; Harada et al 2005 |
| Xanthoangelol D | Phosphorylation | Sugii et al, 2005 |
| YC-1 | Phosphorylation | Huang et al, 2005 |
| YopJ (encoded by Yersinia pseudotuberculosis) | Deubiquintinase for IkBa; | Schesser et al, 1998; Zhou et al, 2005; |
| | Acetylation of IKKbeta | Mittal et al, 2006; Mukherjee & Orth, 2008 |
| Osmotic stress | IkB ubiquitination | Huangfu et al, 2007 |
| Acetaminophen | Degradation | Mancini et al, 2003 |
| Activated Protein C (APC) | Degradation | Yuksel et al, 2002 |
| Alachlor | Degradation | Shimomura-Shimizu et al, 2005 |
| Allylpyrocatechol | Degradation | Sarkar et al, 2008 |
| a-melanocyte-stimulating hormone (a-MSH) | Degradation | Manna & Aggarwal, 1998 |
| Amentoflavone | Degradation | Banerjee et al, 2002; Guruvayoorappan & Kuttan, 2007 |
| Angelica dahurica radix extract | Degradation | Kang et al, 2006 |
| Apple extracts | Degradation/proteasome | Yoon & Liu, 2007 |
| Artemisia capillaris Thunb extract (capillarisin) | Degradation | Hong et al, 2004; Kim et al, 2007; Lee et al, 2007 |
| Artemisia iwayomogi extract | Degradation | Kim et al, 2005 |
| L-ascorbic acid | Degradation | Han et al, 2004 |
| Antrodia camphorata | Degradation | Hseu et al, 2005 |
| Aucubin | Degradation | Jeong et al, 2002 |
| Baicalein | Degradation | Ma et al, 2004 |
| N-(quinolin-8-yl)benzenesulfonamindes | Degradation | Xie et al, 2007 |
| beta-lapachone | Degradation | Manna et al, 1999 |
| Blackberry extract | Degradation | Pergola et al, 2006 |

TABLE G-continued

Examples of NFKB Inhibitors
Any one or more of the following NFKB inhibitors

| | | |
|---|---|---|
| 1-Bromopropane | Degradation | Yoshida et al, 2006 |
| Buchang-tang | Degradation | Shin et al, 2005 |
| Capsaicin (8-methyl-N-vanillyl-6-nonenamide) | Degradation | Singh et al, 1996; Mori et al, 2006; Kang et al, 2007 |
| Catalposide | Degradation | Kim et al, 2004 |
| Clerodendron trichotomum Tunberg Leaves | Degradation | Park & Kim, 2007 |
| Clomipramine/imipramine | Degradation | Hwang et al, 2008 |
| Coptidis rhizoma extract | Degradation | Kim et al, 2007 |
| Cyclolinteinone (sponge sesterterpene) | Degradation | D'Acquisto et al, 2000 |
| DA-9601 (Artemisia asiatica extract) | Degradation | Choi et al, 2006 |
| Diamide (tyrosine phosphatase inhibitor) | Degradation | Toledano & Leonard, 1991; Singh & Aggarwal, 1995 |
| Dihydroarteanniun | Degradation | Li et al, 2006 |
| Dobutamine | Degradation | Loop et al, 2004 |
| Docosahexaenoic acid | Degradation | Weldon et al, 2006 |
| E-73 (cycloheximide analog) | Degradation | Sugimoto et al, 2000 |
| Ecabet sodium | Degradation | Kim et al, 2003 |
| Electrical stimulation of vagus nerve | Degradation | Guarini et al, 2003 |
| Emodin (3-methyl-1,6,8-trihydroxyanthraquinone) | Degradation | Kumar et al, 1998; Huang et al, 2004 |
| Ephedrae herba (Mao) | Degradation | Aoki et al, 2005 |
| Equol | Degradation | Kang et al, 2005 |
| Erbstatin (tyrosine kinase inhibitor) | Degradation | Natarajan et al, 1998 |
| Estrogen (E2) | Degradation/and various other steps | Sun et al, 1998; Kalaitzidis & Gilmore, 2005; Steffan et al, 2006 |
| Ethacrynic acid | Degradation (and DNA binding) | Han et al, 2004 |
| Fludarabine | Degradation | Nishioka et al, 2007 |
| Fosfomycin | Degradation | Yoneshima et al, 2003 |
| Fungal gliotoxin | Degradation | Pahl et al, 1999 |
| Gabexate mesilate | Degradation | Yuksel et al, 2003 |
| Gamisanghyulyunbueum | Degradation | Shin et al, 2005 |
| Genistein (tyrosine kinase inhibitor) | Degradation; caspase cleavage of IkBa | Natarajan et al, 1998; Baxa & Yoshimura, 2003 |
| Genipin | Degradation | Koo et al, 2004 |
| Glabridin | Degradation | Kang et al, 2004 |
| Ginsenoside Re | Degradation | Zhang et al, 2007 |
| Glimepiride | Degradation | Schiekofer et al, 2003 |
| Glucosamine (sulfate or carboxybutyrylated) | Degradation | Largo et al, 2003; Rafi et al, 2007; Rajapakse et al, 2008 |
| gamma-glutamylcysteine synthetase | Degradation | Manna et al, 1999 |
| Glutamine | Degradation | Singleton et al, 2005; Fillmann et al, 2007; Chen et al, 2008 |
| Glycochenodeoxycholate | Degradation | Bucher et al, 2006 |
| Guave leaf extract | Degradation | Choi et al, 2008 |
| Gumiganghwaltang | Degradation | Kim et al, 2005 |
| Gum mastic | Degradation | He et al, 2007 |
| Heat shock protein-70 | Degradation | Chan et al, 2004; Shi et al, 2006 |
| Herbal mixture (Cinnamomi ramulus, Anemarrheriae rhizoma, Officinari rhizoma) | Degradation | Jeong et al, 2008 |
| Hypochlorite | Degradation | Mohri et al, 2002 |
| Ibudilast | Degradation | Kiebala & Maggirwar, 1998 |
| IL-13 | Degradation | Manna & Aggarwal, 1998 |
| Incensole acetate | Degradation | Moussaieff et al, 2007 |
| Intravenous immunoglobulin | Degradation | Ichiyama et al, 2004 |
| Isomallotochromanol and isomallotochromene | Degradation | Ishii et al, 2003 |
| K1L (Vaccinia virus protein) | Degradation | Shisler & Jin, 2004 |
| Kochia scoparia fruit (methanol extract) | Degradation | Shin et al, 2004 |
| Kummerowia striata (Thunb.) Schindl (ethanol extract) | Degradation | Tao et al, 2008 |
| Leflunomide metabolite (A77 1726) | Degradation | Manna & Aggarwal, 1999 |
| Lidocaine | Degradation | Feng et al, 2007; Lahat et al, 2008 |
| Lipoxin A4 | Degradation | Zhang et al, 2007 |
| Losartan | Degradation/NF-kB expression | Chen et al, 2002; Zhu et al, 2007 |
| Low level laser therapy | Degradation | Rizzi et al, 2006 |
| LY294002 (PI3-kinase inhibitor) [2-(4-morpholinyl)-8-phenylchromone] | Degradation | Park et al 2002 |
| MC159 (Molluscum contagiosum virus) | Degradation of IkBb | Murao & Shisler, 2005 |
| Melatonin | Degradation | Zhang et al, 2004 |
| Meloxicam | Degradation | Liu et al, 2007 |
| 5'-methylthioadenosine | Degradation | Hevia et al, 2004 |
| Midazolam | Degradation | Kim et al, 2006 |
| Momordin I | Degradation | Hwang et al, 2005 |
| Morinda officinalis extract | Degradation | Kim et al, 2005 |
| Mosla dianthera extract | Degradation | Lee et al, 2006 |
| Mume fructus extract | Degradation | Choi et al, 2007 |

TABLE G-continued

Examples of NFKB Inhibitors
Any one or more of the following NFKB inhibitors

| | | |
|---|---|---|
| Murr1 gene product | Degradation | Ganesh et al, 2003 |
| Neurofibromatosis-2 (NF-2; merlin) protein | Degradation | Kim et al, 2002 |
| Opuntia ficus indica va saboten extract | Degradation | Lee et al, 2006 |
| Ozone (aqueous) | Degradation | Huth et al, 2007 |
| Paeony total glucosides | Degradation | Chen et al, 2007 |
| Pectenotoxin-2 | Degradation | Kim et al, 2008 |
| Penetratin | Degradation | Letoya et al, 2006 |
| Pervanadate (tyrosine phosphatase inhibitor) | Degradation | Singh & Aggarwal, 1995; Singh et al, 1996 |
| Phenylarsine oxide (PAO, tyrosine phosphatase inhibitor) | Degradation | Mahboubi et al, 1998; Singh & Aggarwal, 1995 |
| beta-Phenylethyl (PEITC) and 8-methylsulphinyloctyl isothiocyanates (MSO) (watercress) | Degradation | Rose et al, 2005 |
| Phenytoin | Degradation | Kato et al, 2005 |
| c-phycocyanin | Degradation | Cherng et al, 2007 |
| Platycodin saponins | Degradation | Aim et al, 2005; Lee et al, 2008 |
| Polymeric formula | Degradation | de Jong et al, 2007 |
| Polymyxin B | Degradation | Jiang et al, 2006 |
| Poncirus trifoliata fruit extract | Degradation; phosphorylation of IkBa | Shin et al, 2006; Kim et al 2007 |
| Probiotics | Degradation | Petrof et al, 2004 |
| Pituitary adenylate cyclase-activating polypeptide (PACAP) | Degradation | Delgado & Ganea, 2001 |
| Prostaglandin 15-deoxy-Delta(12,14)-PGJ(2) | Degradation | Cuzzocrea et al, 2003; Chatterjee et al, 2004 |
| Prodigiosin (Hahella chejuensis) | Degradation | Huh et al, 2007 |
| PS-341 | Degradation/proteasome | Hideshima et al, 2002 |
| Radix asari extract | Degradation | Song et al, 2007 |
| Radix clematidis extract | Degradation | Lee et al, 2009 |
| Resiniferatoxin | Degradation | Singh et al, 1996 |
| Sabaeksan | Degradation | Choi et al, 2005 |
| SAIF (Saccharomyces boulardii anti-inflammatory factor) | Degradation | Sougioultzis et al 2006 |
| Sanguis Draconis | Degradation | Choy et al, 2007 |
| San-Huang-Xie-Xin-Tang | Degradation | Shih et al, 2007 |
| Schisandra fructus extract | Degradation | Kang et al, 2006; Guo et al, 2008 |
| Scutellarin | Degradation | Tan et al, 2007 |
| Sesquiterpene lactones (parthenolide; ergolide; guaianolides; alpha-humulene; trans-caryophyllene) | Degradation | Hehner et al, 1998; Whan Han et al, 2001; Schorr et al, 2002; Medeiros et al, 2007 |
| Sevoflurane/isoflurane | Degradation | Boost et al, 2009 |
| Siegeskaurolic acid (from Siegesbeckia pubescens root) | Degradation | Park et al, 2007 |
| ST2 (IL-1-like receptor secreted form) | Degradation | Takezako et al, 2006 |
| Synadenium carinatum latex lectin | Degradation | Rogerio et al, 2007 |
| Taiwanofungus camphoratus | Degradation | Liu et al, 2007 |
| Taurene bromamine | Degradation | Tokunaga et al, 2007 |
| Thiopental | Degradation | Loop et al, 2002 |
| Tipifarnib | Degradation | Xue et al, 2005 |
| Titanium | Degradation | Yang et al, 2003 |
| TNP-470 (angiogenesis inhibitor) | Degradation | Mauriz et al, 2003 |
| Stinging nettle (Urtica dioica) plant extracts | Degradation | Riehemann et al, 1999 |
| Trichomomas vaginalis infection | Degradation | Chang et al, 2004 |
| Triglyceride-rich lipoproteins | Degradation | Kumwenda et al, 2002 |
| Tussilagone (Farfarae fins) | Degradation | Lim et al, 2008 |
| U0126 (MEK inhibitor) | Degradation | Takaya et al, 2003 |
| Ursodeoxycholic acid | Degradation | Joo et al, 2004 |
| Xanthium strumarium L. (methanol extract) | Degradation | Kim et al, 2005; Yoon et al, 2008 |
| Yulda-Hanso-Tang | Degradation | Jeong et al, 2007 |
| Zinc | Degradation | Uzzo et al, 2006; Bao et al, 2006 |
| Molluscum contagiosum virus MC159 protein | IkBbeta degradation | Murao & Shisler, 2005 |
| Vasoactive intestinal peptide | Degradation (and CBP-RelA interaction) | Delgado & Ganea, 2001; Delgado, 2002 |
| HIV-1 Vpu protein | TrCP ubiquitin ligase inhibitor Bour et al, 2001 | |
| Epoxyquinone A monomer | IKKb/DNA binding | Liang et al, 2006 |
| Ro106-9920 (small molecule) | IkBa ubiqutination inhibitor Swinney et al, 2002 | |
| Furonaphthoquinone | IKK activity | Shin et al, 2006 |
| β-TrCP | Degradation | Kanarek et al, 2012 |

Inhibitors from IMGENEX: NF-kB Pathway Inhibitory Peptides

| Cat.No | Description | Species |
|---|---|---|
| IMG-2009-2 | Antennapedia Control Peptide | N/A |
| IMG-2009-5 | Antennapedia Control Peptide | N/A |
| IMG-2000 | IKKg NEMO Binding Domain (NBD) Inhibitory Peptide Set Functions as an IKKa/IKKb decoy by binding to IKKg NBD, thereby preventing formation of the IKK complex. | H, M, R |

TABLE G-continued

Examples of NFKB Inhibitors
Any one or more of the following NFKB inhibitors

| | | |
|---|---|---|
| IMG-2000-5 | IKKg NEMO Binding Domain (NBD) Inhibitory Peptide Set Functions as an IKKa/IKKb decoy by binding to IKKg NBD, thereby preventing formation of the IKK complex. | H, M, R |
| IMG-2005-5 | MyD88 Homodimerization Inhibitory Peptide Set Functions as a decoy by binding to the MyD88 TIR domain | H, M, R, X, Z |
| IMG-2005-1 | MyD88 Homodimerization Inhibitory Peptide Set Functions as a decoy by binding to the MyD88 TIR domain | H, M, R, X, Z |
| IMG-2004 | NF-kB p50 (NLS) Inhibitory Peptide Set Functions as a p50 decoy by blocking the intracellular recognition mechanism of p50 NLS. | B, C, C, D, H, M, R, X |
| IMG-2004-5 | NF-kB p50 (NLS) Inhibitory Peptide Set Functions as a p50 decoy by blocking the intracellular recognition mechanism of p50 NLS. | B, C, C, D, H, M, R, X |
| IMG-2001 | NF-kB p65 (Ser276) Inhibitory Peptide Set Functions as a p65 decoy through phosphorylation of the Ser276 site on the peptide. | C, D, H, M, M, R |
| IMG-2001-5 | NF-kB p65 (Ser276) Inhibitory Peptide Set Functions as a p65 decoy through phosphorylation of the Ser276 site on the peptide. | C, D, H, M, M, R |
| IMG-2003 | NF-kB p65 (Ser529/536) Inhibitory Peptide Set Functions as a p65 decoy through phosphorylation of the Ser529/536 sites on the peptide. | C, D, H, M, M, R |
| IMG-2003-5 | NF-kB p65 (Ser529/536) Inhibitory Peptide Set Functions as a p65 decoy through phosphorylation of the Ser529/536 sites on the peptide. | C, D, H, M, M, R |
| IMG-2006-5 | TIRAP Inhibitory Peptide Set Functions as a TIRAP decoy by binding to TIR interacting domains on specific TLR receptors. | H, M |
| IMG-2006-1 | TIRAP Inhibitory Peptide Set Functions as a TIRAP decoy by binding to TIR interacting domains on specific TLR receptors. | H, M |
| IMG-2011 set | TLR4 Peptide Inhibitor Set: VIPER | H, M |
| IMG-2002 | TRAF6 Inhibitory Peptide Set Functions as a TRAF6 decoy by binding to the T6DP motif of RANK, thereby preventing binding of RANK to TRAF6. | H, M, R |
| IMG-2002-5 | TRAF6 Inhibitory Peptide Set Functions as a TRAF6 decoy by binding to the T6DP motif of RANK, thereby preventing binding of. RANK to TRAF6 | H, M, R |
| NF kappa B Inhibitors | | |

9-Methylstreptimidone
Z-VRPR-FMK
2-(1,8-naphthyridin-2-yl)-Phenol
5-Aminosalicylic acid
BAY 11-7082
BAY 11-7085
Caffeic acid phenethyl ester
Diethylmaleate
Ethyl 3,4-Dihydroxycinnamate
Helenalin
NFicB Activation Inhibitor II, JSH-23
NFicB Activation Inhibitor III
PPM-18
Pyrrolidinedithiocarbamic acid ammonium salt
(R)-MG-132
Rocaglamide
Sodium Salicylate The presently-disclosed subject matter further includes compositions useful for inhibiting NFκB. Such compositions include an inhibitor. As noted above, such inhibitors can be, for example, a nucleotide, a polypeptide, a small (chemical) molecule, etc. In some embodiments, a composition can include an isolated RNA molecule.

The presently-disclosed subject matter further includes methods of screening candidate inhibitors to identify NFκB inhibitors. In some embodiments, cell or cell line-based methods are used.

Imaging Caspase in an Eye of a Subject

In some embodiments, a diagnostic composition is provided for imaging activated Caspase in an eye of a subject, comprising a fluorescent molecule conjugated to a substrate of Caspase-1 or a molecule that fluoresces following cleavage by Caspase-1. In some embodiments, a method is provided for imaging activated Caspase-1 in an eye of a subject, including administering (e.g., intraocularly or intravenously) to RPE cells of the subject the diagnostic composition, and optically monitoring the spatial clustering of fluorescence.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK®/GENPEPT® accession numbers. The sequences cross-referenced in the GENBANK®/GENPEPT® database are expressly incorporated by reference as are equivalent and related sequences present in GENBANK®/GENPEPT® or other public databases. Also expressly incorporated herein by reference are all annotations present in the GENBANK®/GENPEPT® database associated with the sequences disclosed herein. Unless otherwise indicated or apparent, the references to the GENBANK®/GENPEPT® database are references to the most recent version of the database as of the filing date of this Application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1

Alu RNA accumulation due to DICER1 deficiency in the retinal pigmented epithelium (RPE) is implicated in geographic atrophy (GA), an advanced form of age-related macular degeneration that causes blindness in millions of individuals. The mechanism of Alu RNA-induced cytotoxicity is unknown. Here it is shown that DICER1 deficit or Alu RNA exposure activates the NLRP3 inflammasome and triggers TLR-independent MyD88 signaling via IL-18 in the RPE. Genetic or pharmacological inhibition of inflammasome components (NLRP3, Pycard, Caspase-1), MyD88, or IL-18 prevents RPE degeneration induced by DICER1 loss or Alu RNA exposure. These findings, coupled with the observation that human GA RPE contains elevated amounts of NLRP3, PYCARD and IL-18, and evidence of increased Caspase-1 and MyD88 activation, provide a rationale for targeting this pathway in GA. The findings also reveal a novel function of the inflammasome outside the immune system and a surprising immunomodulatory action of mobile elements.

Age-related macular degeneration (AMD) affects the vision of millions of individuals (Smith et al., 2001). AMD is characterized by degeneration of the retinal pigmented epithelium (RPE), which is situated between the retinal photoreceptors and the choroidal capillaries (Ambati et al., 2003). RPE dysfunction disrupts both photoreceptors and choroidal vasculature (Blaauwgeers et al., 1999; Lopez et al., 1996; McLeod et al., 2009; Vogt et al., 2011). These tissue disruptions lead to atrophic or neovascular disease phenotypes. Although there are therapies for neovascular AMD, there is no effective treatment for the more common atrophic form. GA, the advanced stage of atrophic AMD, is characterized by degeneration of the RPE, and is the leading cause of untreatable vision loss.

Recently it was shown that a dramatic and specific reduction of the RNase DICER1 leads to accumulation of Alu RNA transcripts in the RPE of human eyes with GA (Kaneko et al., 2011). These repetitive element transcripts, which are non-coding RNAs expressed by the highly abundant Alu retrotransposon (Batzer and Deininger, 2002), induce human RPE cell death and RPE degeneration in mice. DICER1 deficit in GA RPE was not a generic cell death response because DICER1 expression was not dysregulated in other retinal diseases. Likewise, Alu RNA accumulation did not represent generalized retrotransposon activation due to a stress response in dying cells because other retrotransposons were not elevated in GA RPE.

DICER1 is central to mature microRNA biogenesis (Bernstein et al., 2001). Yet following DICER1 deficit, the accumulation of Alu RNA and not the lack of mature microRNAs was the critical determinant of RPE cell viability (Kaneko et al., 2011). Moreover, 7SL RNA, transfer RNA, and primary microRNAs do not induce RPE degeneration (Kaneko et al., 2011), ruling out a nonspecific toxicity of excess, highly structured RNA. Still, the precise mechanisms of Alu RNA cytotoxicity are unknown.

Although the retina is exceptional for its immune privilege (Streilein, 2003), insults mediated by innate immune sensors can result in profound inflammation. The three major classes of innate immune receptors include the TLRs, RIG-1-like helicases, and NLR proteins (Akira et al., 2006). Numerous innate immune receptors are expressed in the RPE (Kumar et al., 2004), and several exogenous substances can induce retinal inflammation (Allensworth et al., 2011; Kleinman et al., 2012). However, it is not known whether this surveillance machinery recognizes or responds to host endogenous RNAs. The concept was explored that innate immune machinery, whose canonical function is the detection of pathogen associated molecular patterns and other moieties from foreign organisms, might also recognize Alu RNA.

Indeed, it was shown that Alu transcripts can hijack innate immunity machinery to induce RPE cell death. Surprisingly, the data show that DICER1 deficit or Alu RNA activates the NLRP3 inflammasome in a MyD88-dependent, but TLR-independent manner. NLRP3 inflammasome activation in vivo has been largely restricted to immune cells, although the data open the possibility that NLRP3 activity may be more widespread, as reflected by examples in cell culture studies of keratinocytes (Feldmeyer et al., 2007; Keller et al., 2008). The data also broaden the scope of DICER1 function beyond microRNA biogenesis, and identify it as a guardian against aberrant accumulation of toxic retrotransposon elements that comprise roughly 50% of the human genome (Lander et al., 2001). In sum, the findings present a novel self-recognition immune response, whereby endogenous non-coding RNA-induced NLRP3 inflammasome activation results from DICER1 deficiency in a non-immune cell.

Results

Alu RNA does not Activate a Variety of TLRs or RNA Sensors

Figure 1:
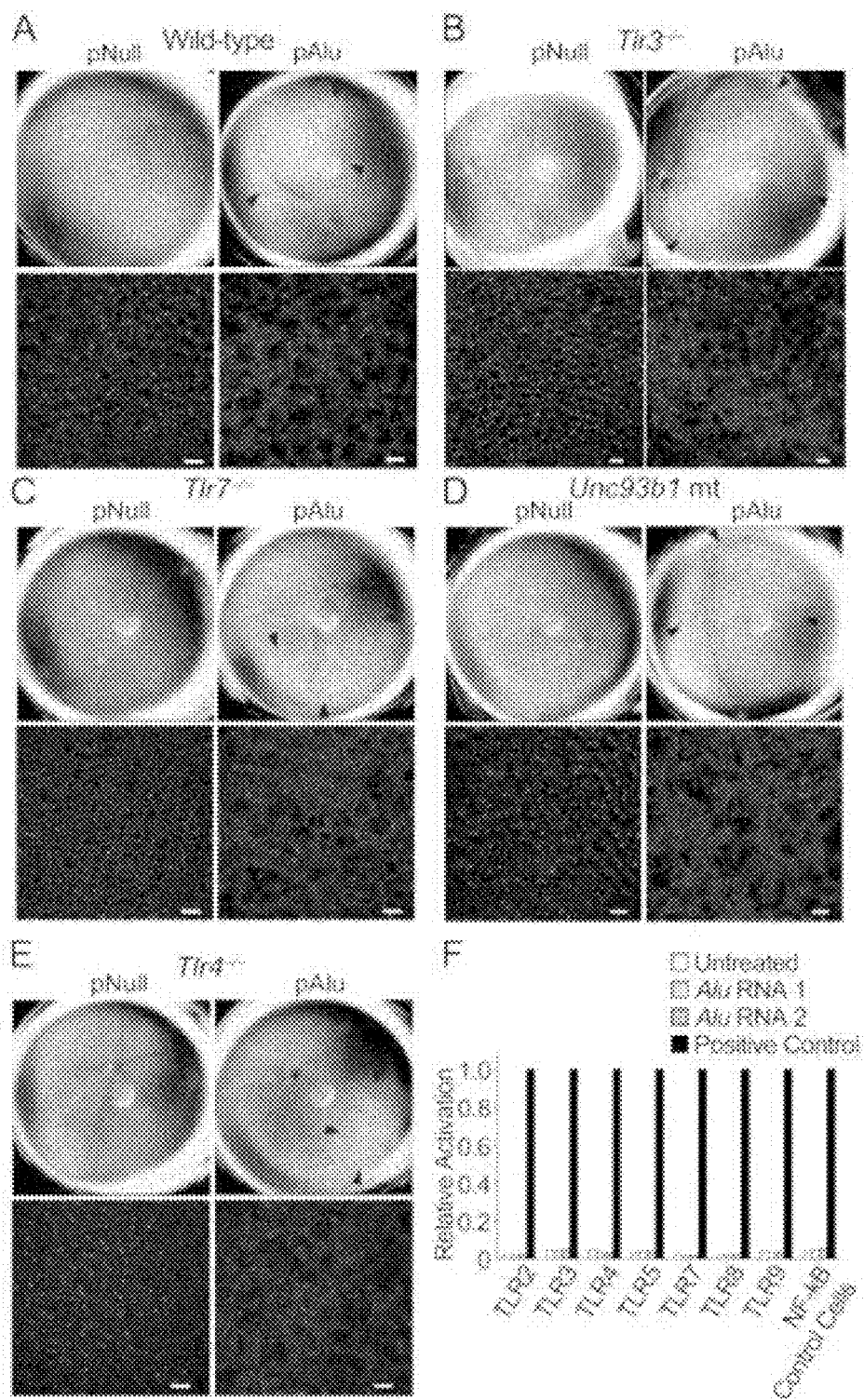
FIG. 1. Alu RNA does not activate or function via toll-like receptors (TLRs) (A-E) pAlu, but not pNull, induces RPE degeneration in WT (A), Tlr3$^{-/-}$ (B), Tlr7$^{-/-}$ (C), Unc93b1 mt mice, which are functionally deficient in TLRs-3,7,9 (D), and Tlr4$^{-/-}$ mice (E). Representative images shown. n=8-12. Fundus photographs, top row; Flat mounts stained for zonula occludens-1 (ZO-1; red), bottom row. Degeneration outlined by blue arrowheads. Scale bars, 20 µm. (F) Stimulation of HEK293 cell lines expressing various TLRs with either of two different Alu RNA sequences does not elicit NF-κB activation. Positive (+) controls using TLR-specific ligands activated NF-κB. n=3. Data are represented as mean+/−SEM. See also FIG. 8.

Alu RNA has single-stranded (ss) RNA and double-stranded (ds) RNA motifs (Sinnett et al., 1991). Thus it was tested whether Alu RNA induced RPE degeneration in mice deficient in toll-like receptor-3 (TLR3), a dsRNA sensor (Alexopoulou et al., 2001), or TLR7, a ssRNA sensor (Diebold et al., 2004; Heil et al., 2004). Subretinal delivery of a plasmid coding for Alu RNA (pAlu) induced RPE degeneration in Tlr3$^{-/-}$ and Tlr7$^{-/-}$ mice just as in wild-type (WT) mice (FIGS. 1A-C). It was previously shown that ≥21-nucleotide fully complementary siRNAs activate TLR3 on RPE cells (Kleinman et al., 2011). Lack of TLR3 activation by Alu RNA is likely due to its complex structure containing multiple hairpins and bulges that might preclude TLR3 binding. Neither 7SL RNA, the evolutionary precursor of Alu RNA, nor p7SL induced RPE degeneration in WT mice (FIGS. 8A and 8B), suggesting that Alu RNA cytotoxicity might be due to as yet unclear structural features. pAlu induced RPE degeneration in Unc93b1 mice (FIG. 1D), which lack TLR3, TLR7, and TLR9 signaling (Tabeta et al., 2006), indicating that these nucleic acid sensors are not activated by Alu RNA redundantly. pAlu induced RPE degeneration in Tlr4$^{-/-}$ mice (FIG. 1E), and the TLR4 antagonist *Rhodobacter sphaeroides* LPS (Qureshi et al., 1991) did not inhibit pAlu-induced RPE degeneration in WT mice (FIG. 8C). Thus the observed RPE cell death is not due to lipopolysaccharide contamination. Further, two different in vitro transcribed Alu RNAs (Kaneko et al., 2011) did not activate multiple TLRs (FIG. 1F).

Next it was tested whether other dsRNA sensors such as MDA5 (Kato et al., 2006) or PKR (encoded by Prkr, (Yang et al., 1995)) might mediate Alu RNA toxicity. However, pAlu induced RPE degeneration in Mda5$^{-/-}$ and Prkr$^{-/-}$ mice (FIGS. 8D and 8E). It was tested whether the 5'-triphosphate on in vitro transcribed Alu RNA, which could activate RIG-I or IFIT-1 that sense this moiety (Hornung et al., 2006; Pichlmair et al., 2011), was responsible for RPE degeneration. Dephosphorylated Alu RNA induced RPE degeneration in WT mice just as well as Alu RNA not subjected to dephosphorylation (FIG. 8F), indicating that this chemical group is not responsible for the observed cell death. Indeed a 5'-triphosphate ssRNA that activates RIG-I does not induce RPE degeneration in mice (Kleinman et al., 2011). Further, pAlu induced RPE degeneration in mice deficient in MAVS (FIG. 8G), through which RIG-I and MDA-5 signal (Kumar et al., 2006; Sun et al., 2006). Collectively these data pointed to a novel mechanism of Alu RNA-induced RPE degeneration not mediated by a wide range of canonical RNA sensors.

Alu RNA Cytotoxicity is Mediated Via MyD88 and IL-18

Figure 2:
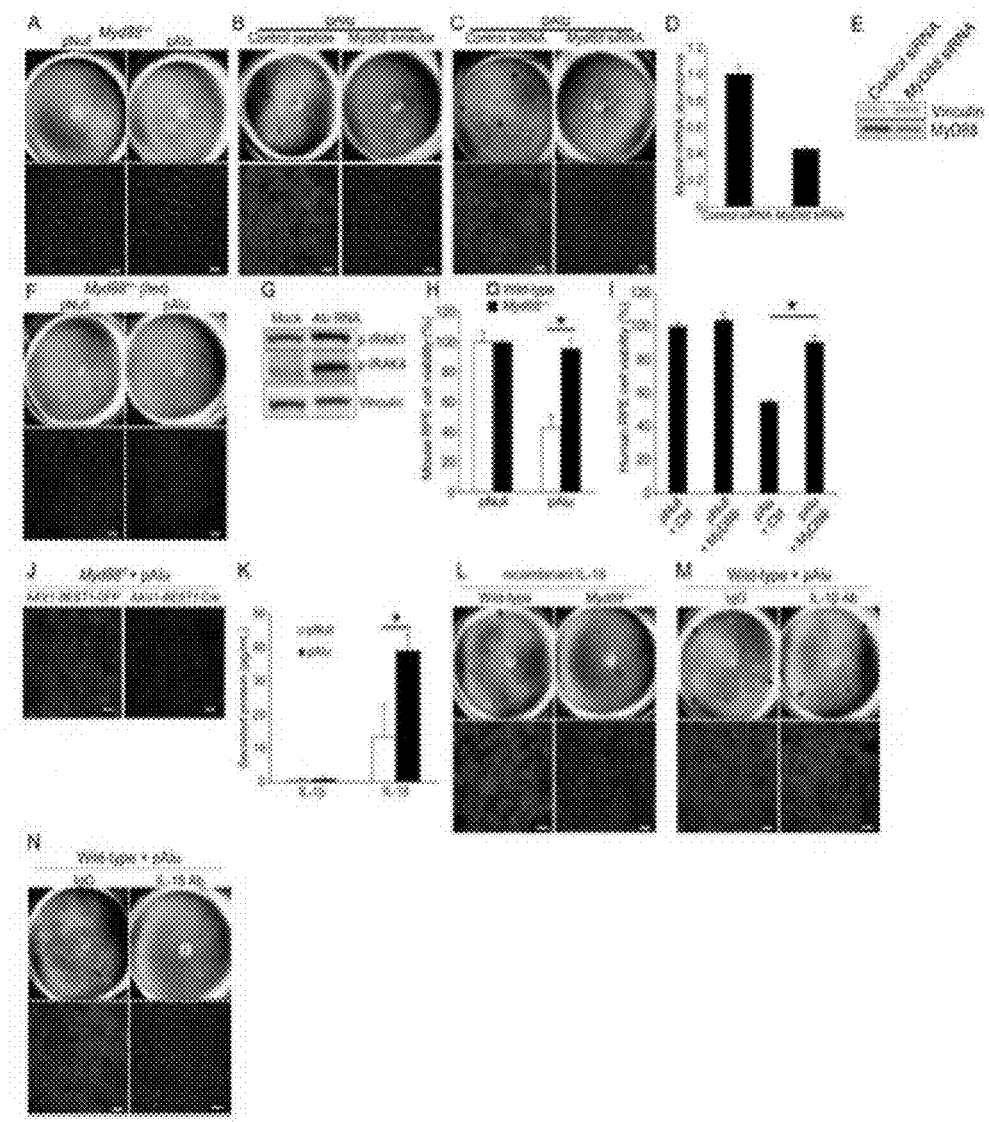
FIG. 2. Alu RNA induces RPE degeneration via MyD88 (A) pAlu does not induce RPE degeneration in Myd88$^{-/-}$ mice. (B) pAlu-induced RPE degeneration in WT mice is inhibited by a MyD88 homodimerization peptide inhibitor (MyD88i), but not by a control peptide. (C) pAlu-induced RPE degeneration in WT mice is inhibited by cholesterol-conjugated Myd88 siRNA but not control siRNA. (D and E) siRNA targeting MyD88 (siMyD88) reduces target gene (D) and protein (E) abundance in mouse RPE cells compared to control siRNA. n=3, *p<0.05 by Student t-test. (F) pAlu does not induce RPE degeneration in Myd88 heterozygous (het) mice. (G) Western blot of Alu RNA-induced IRAK1 and IRAK4 phosphorylation in human RPE cells. Image representative of 3 experiments. (H) pAlu reduces cell viability of WT but not Myd88 mouse RPE cells. (I) Loss of human RPE cell viability induced by pAlu is rescued by MyD88i. (J) AAV1-BEST1-Cre, but not AAV1-BEST1-GFP, protected Myd88$^{f/f}$ mice from pAlu-induced RPE degeneration. (K) pAlu induces IL-18 secretion from human RPE cells measured by ELISA. IL-1β secretion is barely detectable. n=3, *p<0.05 by Student t-test. (L) Recombinant IL-18 induces RPE degeneration in WT but not Myd88$^{-/-}$ mice. (M and N) pAlu-induced RPE degeneration in WT mice is rescued by IL-18 neutralizing antibody (N) but not by IL-1β neutralizing antibody (M). Representative images shown. n=8-12. Fundus photographs, top row; ZO-1 stained (red) flat mounts, bottom row. Degeneration outlined by blue arrowheads. Scale bars, 20 µm (A-C,F,J,L-N). n=3, *p<0.05 by Student t-test. Data are represented as mean+/−SEM (D,E,H,I,K). See also FIG. 9.

The involvement of TRIF (encoded by Ticam1), an adaptor for TLR3 and TLR4 (Hoebe et al., 2003; Yamamoto et al., 2003), and MyD88, an adaptor for all TLRs except TLR3 (Akira et al., 2006; Alexopoulou et al., 2001; Suzuki et al., 2003) were then tested. Alu RNA induced RPE degeneration in Ticam1$^{-/-}$ mice (FIG. 9A), consistent with findings in Tlr3$^{-/-}$ and Tlr4$^{-/-}$ mice. Unexpectedly, neither Alu RNA nor two different pAlu plasmids induced RPE degeneration in Myd88$^{-/-}$ mice (FIGS. 2A, 9B, and 9C). Intravitreous delivery of a peptide inhibitor of MyD88 homodimerization (Loiarro et al., 2005) prevented RPE degeneration induced by Alu RNA in WT mice, whereas a control peptide did not do so (FIG. 2B). A MyD88-targeting short interfering RNA (siRNA), which was shorter than 21 nucleotides in length to prevent TLR3 activation and conjugated to cholesterol to enable cell permeation (Kleinman et al., 2008), but not a control siRNA, inhibited RPE degeneration induced by pAlu in WT mice (FIGS. 2C-2E). Myd88$^{+/-}$ heterozygous mice were protected against Alu RNA-induced RPE degeneration (FIGS. 2F and 9D), corroborating the siRNA studies that partial knockdown of MyD88 is therapeutically sufficient.

MyD88-mediated signal transduction induced by interleukins leads to recruitment and phosphorylation of IRAK1 and IRAK4 (Cao et al., 1996; Kanakaraj et al., 1999; Suzuki et al., 2003; Suzuki et al., 2002). Alu RNA increased IRAK1/4 phosphorylation in human RPE cells (FIG. 2G), supporting the concept that Alu RNA triggers MyD88 signaling. The MyD88 inhibitory peptide reduced Alu RNA-induced IRAK1/4 phosphorylation in human RPE cells (FIG. 9E), confirming its mode of action.

Next it was assessed whether MyD88 activation mediates Alu RNA-induced cell death in human and mouse RPE cell culture systems. Consonant with the in vivo data, pAlu reduced cell viability in WT but not Myd88$^{-/-}$ mouse RPE cells (FIG. 2H). The MyD88-inhibitory peptide, but not a control peptide, inhibited cell death in human RPE cells transfected with pAlu (FIG. 2I). Together, these data indicate that MyD88 is a critical mediator of Alu RNA-induced RPE degeneration.

MyD88 is generally considered an adaptor of immune cells (O'Neill and Bowie, 2007). However, Alu RNA induced cell death via MyD88 in RPE monoculture. Thus, it was tested whether Alu RNA-induced RPE degeneration in mice was also dependent solely on MyD88 activation in RPE cells. Conditional ablation of MyD88 in the RPE by subretinal injection of AAV1-BEST1-Cre in Myd88$^{f/f}$ mice protected against Alu RNA-induced RPE degeneration (FIGS. 2J and 9F). Consistent with this finding, Alu RNA induced RPE degeneration in WT mice receiving Myd88$^{-/-}$ bone marrow but did not do so in Myd88$^{-/-}$ mice receiving WT bone marrow (FIG. 9G). Collectively, these results indicate that MyD88 expression in the RPE, and not in circulating immune cells, is critical for Alu RNA-induced RPE degeneration. These findings comport with histopathological studies of human GA tissue that show no infiltration of immune cells in the area of pathology (personal communication, C. A. Curcio, H. E. Grossniklaus, G. S. Hageman, L. V. Johnson).

Although MyD88 is critical in TLR signaling (O'Neill and Bowie, 2007), MyD88 activation by Alu RNA was independent of TLR activation. Thus, other mechanisms of MyD88 involvement were examined. MyD88 can regulate IFN-γ signaling by interacting with IFN-γ receptor 1 (encoded by Ifngr1) (Sun and Ding, 2006). However, pAlu induced RPE degeneration in both Ifng$^{-/-}$ and Ifngr1$^{-/-}$ mice (FIGS. 9H and 9I). MyD88 is also essential in interleukin-1 signaling (Muzio et al., 1997). Thus, it was tested whether IL-1β and the related cytokine IL-18, both of which activate MyD88 (Adachi et al., 1998), mediated Alu RNA cytotoxicity. Interestingly, whereas Alu RNA overexpression in human RPE cells increased IL-18 secretion, IL-1β secretion was barely detectable (FIG. 2K).

Recombinant IL-18 induced RPE degeneration in WT but not Myd88$^{-/-}$ mice (FIG. 2L). IL-18 neutralization protected against pAlu-induced RPE degeneration in WT mice, but IL-1β did not (FIGS. 2M and 2N). Also, pAlu induced RPE degeneration in Il1r1$^{-/-}$ mice but not Il18r1$^{-/-}$ mice (FIGS. 9J and 9K). These data indicate that IL-18 is an effector of Alu RNA-induced cytotoxicity.

Alu RNA Activates the NLRP3 Inflammasome

Figure 3:
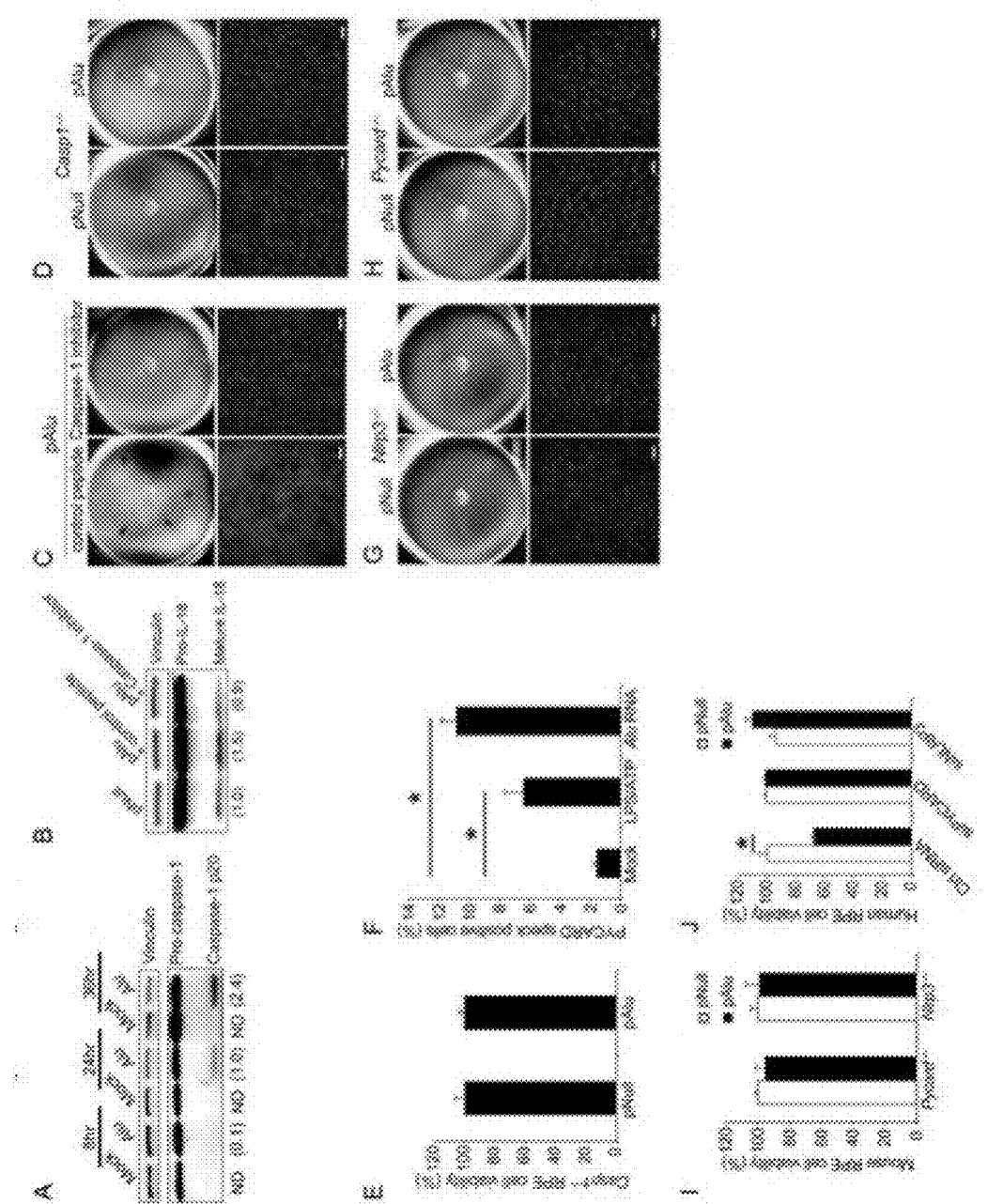
FIG. 3. Alu RNA induces RPE degeneration via NLRP3 inflammasome (A) Western blot of Caspase-1 activation (p20 subunit) by Alu RNA in human RPE cells. (B) Western blot of pAlu-induced IL-18 maturation in RPE cell lysates in wild-type mice impaired by Caspase-1 peptide inhibitor. (C) Caspase-1 peptide inhibitor protects WT mice from pAlu-induced RPE degeneration. (D and E) pAlu does not induce RPE degeneration in Casp1$^{-/-}$ mice or (E) cytotoxicity in Casp1$^{-/-}$ mouse RPE cells. (F) Alu RNA and LPS+ATP induce formation of PYCARD clusters in human RPE cells transfected with GFP-PYCARD. (G and H) pAlu does not induce RPE degeneration in Nlrp3$^{-/-}$ (G) or Pycard$^{-/-}$ (H) mice. (I) Nlrp3$^{-/-}$ and Pycard$^{-/-}$ mouse RPE cells are protected against pAlu-induced loss of cell viability. (J) siRNAs targeting NLRP3 or PYCARD rescued human RPE cells from pAlu-induced cytotoxicity, compared to control siRNA. n=3-4, *p<0.05 by Student t-test (A,B,E,F,I,J). Images representative of 3 experiments. Densitometry values normalized to Vinculin are shown in parentheses (A,B). Fundus photographs, top row; ZO-1 stained (red) flat mounts, bottom row. Degeneration outlined by blue arrowheads. n=8-12. Scale bars, 20 µm (C,D,G,H). Representative images shown. See also FIG. 11.

It was explored whether Caspase-1 (encoded by Casp1), a protease that induces maturation of interleukins into biologically active forms (Ghayur et al., 1997; Gu et al., 1997; Thornberry et al., 1992), was involved in Alu RNA-induced RPE degeneration. Alu RNA treatment of human RPE cells led to Caspase-1 activation as measured by western blotting and by a fluorescent reporter of substrate cleavage (FIGS. 3A and 10A). Indeed, Alu RNA induced Caspase-1 activation in other cell types such as HeLa and THP-1 monocytic cells (FIG. 10B), suggesting that Alu RNA cytotoxicity has potentially broad implications in many systems. Intravitreous delivery of the Caspase-1-inhibitory peptide Z-WEHD-FMK, but not a control peptide Z-FA-FMK, blocked IL-18 maturation and pAlu-induced RPE degeneration in WT mice (FIGS. 3B and 3C). The Caspase-1-inhibitory peptide blocked Alu RNA-induced substrate cleavage in human RPE cells (FIG. 10C), confirming its mode of action. Similarly, Casp1$^{-/-}$ mice treated with Alu RNA or pAlu did not exhibit RPE degeneration (FIGS. 3D and 10D). Also, pAlu did not induce cell death in Casp1$^{-/-}$ mouse RPE cells (FIG. 3E).

Caspase-1 can be activated within a multiprotein innate immune complex termed the inflammasome (Tschopp et al., 2003). The best-characterized inflammasome pathway is one that is activated by binding of NLRP3 to the caspase-1 adaptor ASC (encoded by PYCARD). One hallmark of inflammasome assembly is spatial clustering of PYCARD (Fernandes-Alnemri et al., 2007). In human RPE cells transfected with fluorescent tagged PYCARD (GFP-PYCARD), Alu RNA induced the appearance of a brightly fluorescent cytoplasmic cluster similar to treatment with LPS and ATP, which activates the NLRP3 inflammasome (FIGS. 3F and 10E) (Mariathasan et al., 2006).

Next the functional relevance of NLRP3 and PYCARD to Alu RNA cytotoxicity was tested. Neither pAlu nor Alu RNA induced RPE degeneration in either Nlrp3$^{-/-}$ or Pycard$^{-/-}$ mice (FIGS. 3G, 3H, 10F and 10G), demonstrating the critical importance of the inflammasome in Alu RNA cytotoxicity. Also, pAlu did not induce cell death in Nlrp3$^{-/-}$ or Pycard$^{-/-}$ mouse RPE cells (FIG. 3I). Moreover, knockdown of NLRP3 or PYCARD by siRNAs rescued pAlu-induced human RPE cell death (FIGS. 3J and 10H). These findings provide direct evidence that NLRP3 activation in response to Alu RNA occurs in RPE cells and does not require the presence of other immune cells.

It was determined that IL-18 and MyD88 activation indeed were downstream of Caspase-1 activation by showing (1) that whereas MyD88 inhibition reduced Alu RNA-induced IRAK1/4 phosphorylation in human RPE cells (FIG. 9E), it did not reduce Alu RNA-induced Caspase-1 cleavage or fluorescent substrate cleavage (FIGS. 10I and 10J); (2) that IL-18 neutralization did not inhibit Alu RNA-induced Caspase-1 cleavage (FIG. 10K); and (3) that Caspase-1 inhibition reduced Alu RNA-induced phosphorylation of IRAK1/4 (FIG. 10L).

Alu RNA Induces Mitochondrial ROS and NLRP3 Priming

Figure 4:
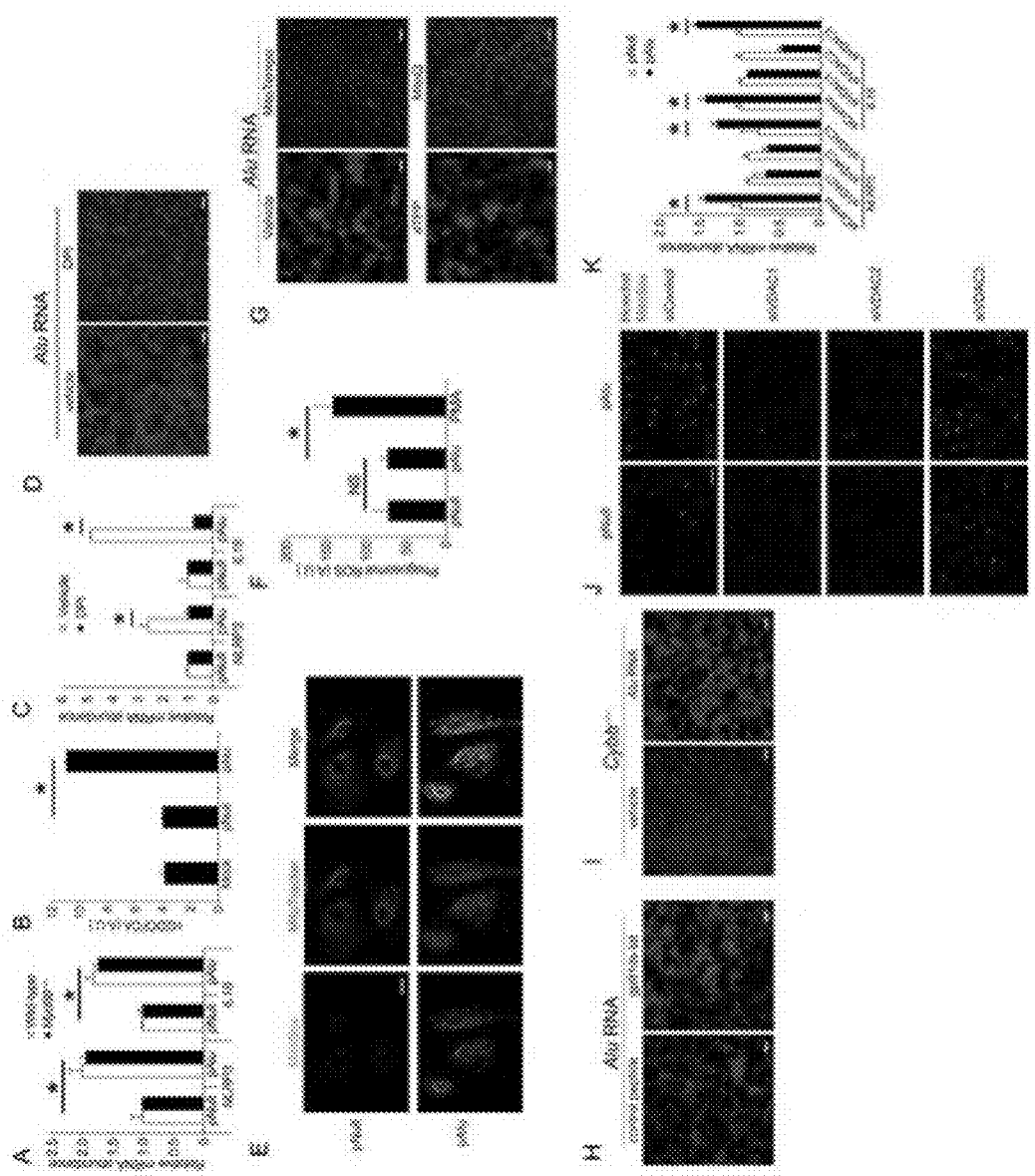
FIG. 4. Alu RNA induces mitochondrial ROS production and NLRP3 priming (A) pAlu induces NLRP3 and IL18 mRNAs in WT and Myd88$^{-/-}$ mouse RPE cells. (B) pAlu induces generation of reactive oxygen species (ROS) in human RPE cells as monitored with the fluorescent probe H$_2$DCFDA (A.U, arbitrary units). (C) DPI blocks pAlu-induced NLRP3 and IL18 mRNAs in human RPE cells. (D) DPI protects WT mice from pAlu-induced RPE degeneration. (E) pAlu induces generation of mitochondrial reactive oxygen species in human RPE cells as detected by the fluorescence of MitoSOX Red (green pseudocolor), colocalized with respiring mitochondria labeled by MitoTracker Deep Red (red). (F) PMA, but not pAlu, induces phagosomal ROS generation, as assessed by fluorescent Fc OXY-BURST Green assay in human RPE cells. (A.U, arbitrary units). (G) MitoTempo and MitoQ, but not vehicle or dTPP controls, prevent Alu RNA-induced RPE degeneration in WT mice. (H) NADPH oxidase inhibitor gp91ds-tat or a scrambled peptide do not prevent Alu RNA-induced RPE degeneration in WT mice. (I) Alu RNA induces RPE degeneration mice deficient in Cybb (which encodes the gp91$^{phox}$ subunit of NADPH oxidase). (J and K) siRNAs targeting VDAC1 and VDAC2, but not VDAC3 or scrambled control, prevent pAlu-induced mROS generation (J) and upregulation of NLRP3 and IL18 mRNAs (K) in human RPE cells. mROS visualized with MitoSox Red dye and cell nuclei with Hoechst stain. n=3-4, *p<0.05 by Student t-test (A-C, K), NS, not significant by Student t-test (F). Representative images shown. n=8-12. ZO-1 stained (red) flat mounts. Scale bars, 20 nm (D, E, G-I), n=3-4. Scale bar, 100 µm (J). See also FIG. 11.

NLRP3 inflammasome function requires two signals, the first of which is termed priming. pAlu induced inflammasome priming as it upregulated both NLRP3 and IL18 mRNAs. This priming occurred equivalently in both WT and Myd88$^{-/-}$ mouse RPE cells (FIG. 4A), further corroborating that MyD88 functions downstream of NLRP3 in this system. Akin to other inflammasome agonists that do not directly interact with NLRP3 (Tschopp and Schroder, 2010), a physical interaction between Alu RNA and NLRP3 was not observed (FIG. 11A). To determine how Alu RNA primed the inflammasome, it was studied whether it induced reactive oxygen species (ROS) production, a signal for priming (Bauernfeind et al., 2011; Nakahira et al., 2011). pAlu induced ROS generation in human RPE cells (FIG. 4B), and the ROS inhibitor diphenyliodonium (DPI) blocked pAlu-induced NLRP3 and IL18 mRNA upregulation and Alu RNA-induced RPE degeneration in WT mice (FIGS. 4C and 4D). As DPI blocks mitochondrial ROS and phagosomal ROS (Li and Trush, 1998), it was tested which pathway was triggered because there is controversy surrounding the source of ROS contributing to NLRP3 responses (Latz, 2010).

MitoSOX Red was used, which labels ROS-generating mitochondria, in combination with MitoTracker Deep Red, which labels respiring mitochondria. To monitor phagosomal ROS generation, Fc OxyBURST Green was used, which measures activation of NADPH oxidase within the phagosome. A marked increase in ROS-generating mitochondria was observed in human RPE cells transfected with pAlu (FIG. 4E). In contrast, whereas phorbol myristate acetate (PMA) induced phagosomal ROS as expected (Savina et al., 2006), pAlu did not do so (FIG. 4F). These data are consistent with the findings that NLRP3 responses are impaired by mitochondrial ROS inhibitors (Nakahira et al., 2011; Zhou et al., 2011) but are preserved in cells carrying genetic mutations that impair NADPH-oxidase-dependent ROS production (Meissner et al., 2010; van Bruggen et al., 2010).

Consonant with these reports and the observation that the principal source of cellular ROS is mitochondria (Murphy, 2009), it was found that the mitochondria-targeted antioxidants Mito-TEMPO and MitoQ (Murphy and Smith, 2007; Nakahira et al., 2011) both blocked Alu RNA-induced RPE degeneration in WT mice, whereas dTPP, a structural analog of MitoQ that does not scavenge mitochondrial ROS, did not do so (FIG. 4G). In contrast, gp91ds-tat, a cell-permeable peptide that inhibits association of two essential NADPH oxidase subunits (gp91$^{phox}$ and p47$^{phox}$) (Rey et al., 2001), did not do so (FIG. 4H). Corroborating these data, Alu RNA induced RPE degeneration in mice deficient in Cybb (which encodes gp91$^{phox}$) just as in WT mice (FIG. 4I). Next the voltage-dependent anion channels (VDAC) was studied because VDAC1 and VDAC2, but not VDAC3, are important in mitochondrial ROS produced by NLRP3 activators in macrophages (Zhou et al., 2011). Consistent with these observations, siRNA knockdown of VDAC1 and VDAC2, but not VDAC3, impaired pAlu-induced mitochondrial ROS (FIGS. 4J and 11B) and NLRP3 and IL18 mRNA induction in human RPE cells (FIG. 4K). Collectively, these data implicate mitochondrial ROS in Alu RNA-induced NLRP3 inflammasome-mediated RPE degeneration.

Alu RNA does not Induce RPE Degeneration Via Pyroptosis

Figure 5:
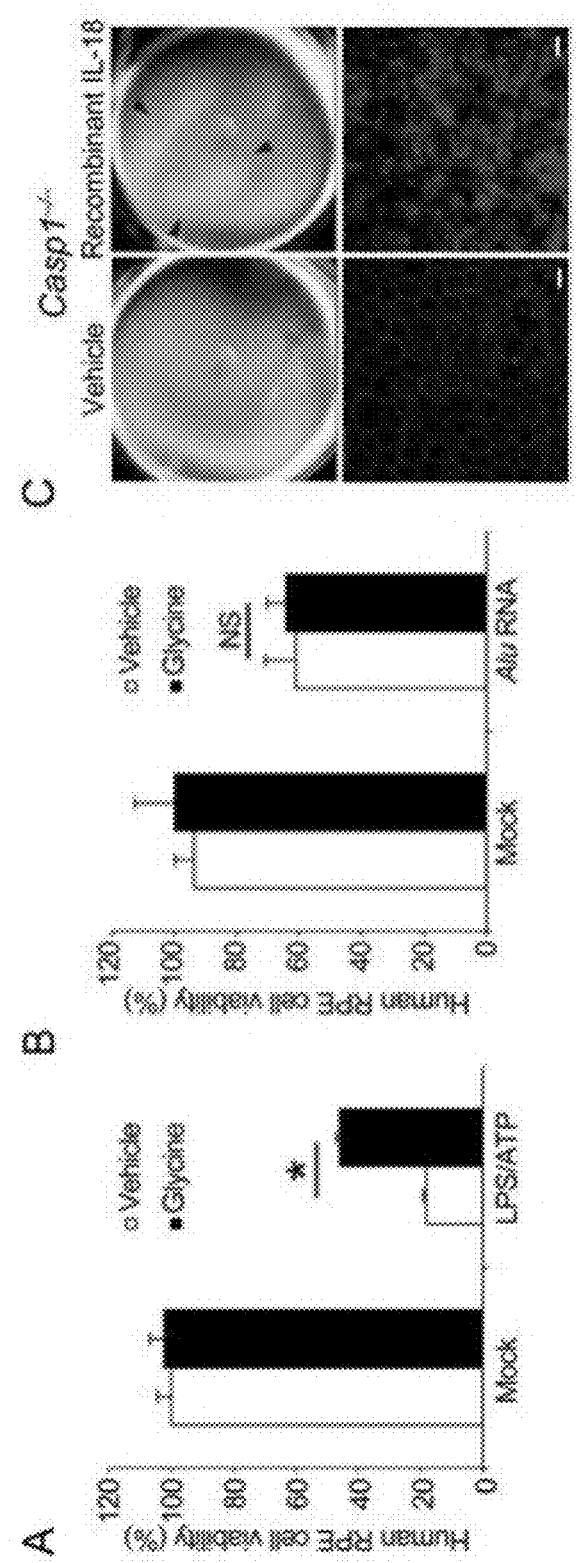
FIG. 5. RPE degeneration does not occur via pyroptosis (A and B) Glycine inhibits human RPE cell death induced by LPS+ATP (A) but not by pAlu (B). (C) Recombinant IL-18 induces RPE degeneration in Casp1$^{-/-}$ mice. n=3-4 (A,B), *p<0.05 by Student t-test. Representative images shown. n=8-12. Fundus photographs, top row; ZO-1 stained (red) flat mounts, bottom row. Degeneration outlined by blue arrowheads. Scale bars, 20 µm (C).

Alu RNA activates Caspase-1, which can trigger pyroptosis, a form of cell death characterized by formation of membrane pores and osmotic lysis (Fink and Cookson, 2006). The cytoprotective agent glycine, which attenuates pyroptosis (Fink et al., 2008; Fink and Cookson, 2006; Verhoef et al., 2005), inhibited human RPE cells death induced by LPS+ATP but not by Alu RNA (FIGS. 5A and 5B). Pyroptosis requires Caspase-1 but can proceed independent of IL-18 (Miao et al., 2010). Thus, the finding that IL-18 induced RPE degeneration in Casp1$^{-/-}$ mice (FIG. 5C), coupled with the lack of rescue by glycine, suggests that Alu RNA-induced RPE degeneration does not occur via pyroptosis.

DICER1 Loss Induces Cell Death Via Inflammasome

Figure 6:
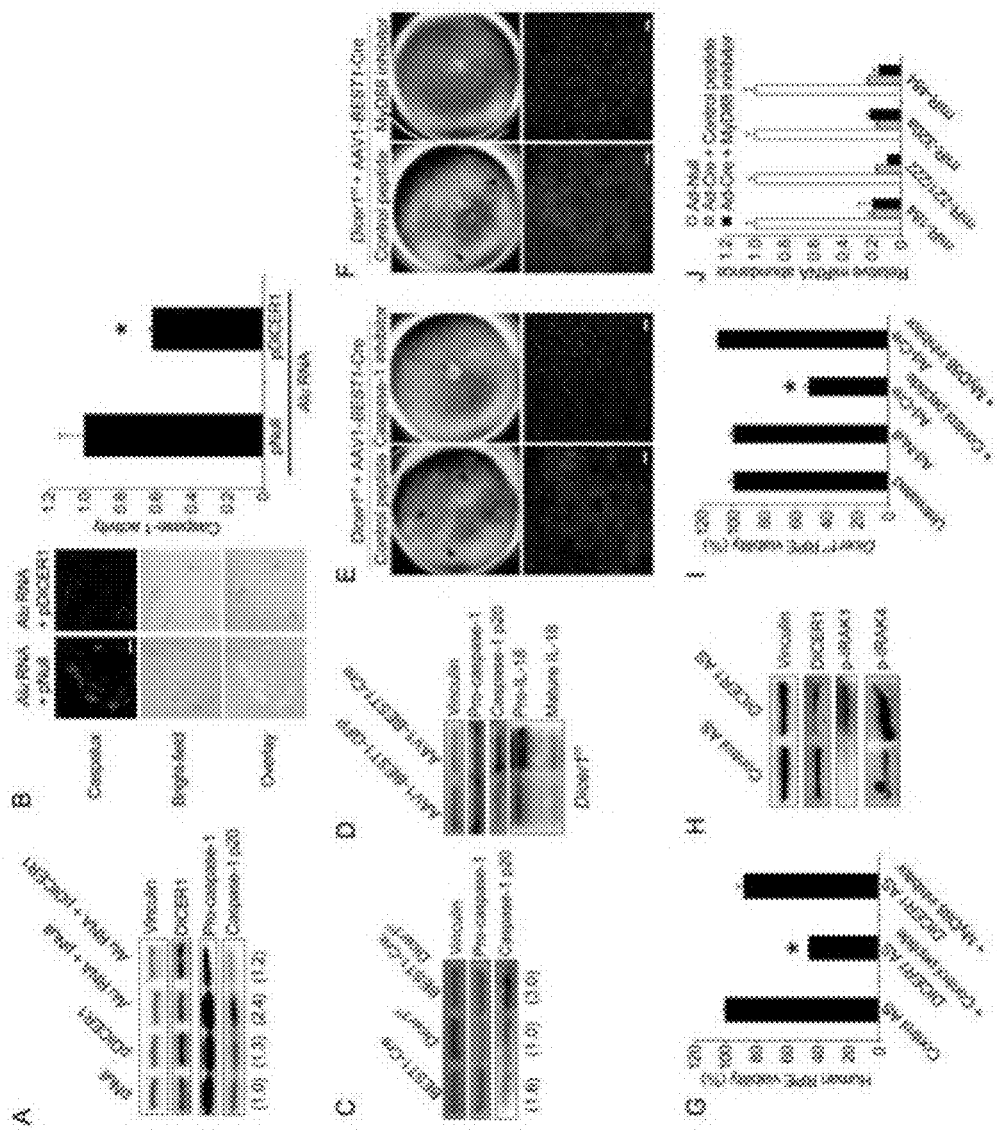
FIG. 6. DICER1 loss induces cell death via inflammasome (A) Western blot of Alu RNA-induced Caspase-1 cleavage (p20) inhibited by DICER1 overexpression in human RPE cells. (B and C) DICER1 overexpression reduces Alu RNA-induced Caspase-1 activation in human RPE cells (measured by cleavage (B left panel, green) of Caspalux®1 fluorescent substrate). Fluorescence quantification shown in right panel. (C) Western blot of increased Caspase-1 activation (p20 subunit) in RPE cell lysates of BEST1-Cre; Dicer1$^{f/f}$ mice compared to BEST1-Cre or Dicer1$^{f/f}$ mice. (D) Western blot of increased Caspase-1 activation (p20 subunit) and IL-18 maturation in RPE cell lysates of Dicer1$^{f/f}$ mice treated with AAV1-BEST1-Cre. (E and F) RPE degeneration induced by AAV1-BEST1-Cre in Dicer1$^{f/f}$ mice is rescued by peptide inhibitors of either Caspase-1 (E) or MyD88 (F). (G) MyD88 inhibitor rescues loss of human RPE cell viability induced by DICER1 antisense (AS) treatment. (H) DICER1 antisense (AS) treatment of human RPE cells reduces DICER1 and increases IRAK1 and IRAK4 phosphorylation. (I) MyD88 inhibitor rescues loss of cell viability in Dicer1$^{f/f}$ mouse RPE cells treated with adenoviral vector coding for Cre recombinase (Ad-Cre). (J) Ad-Cre induced global miRNA expression deficits in Dicer1$^{f/f}$ mouse RPE cells compared to Ad-Null.

It was previously demonstrated that the key role of DICER1 in maintaining RPE cell health (Kaneko et al., 2011): DICER1-cleaved Alu RNA did not induce RPE degeneration in vivo; DICER1 overexpression protected against Alu RNA-induced RPE degeneration; and DICER1 loss-induced RPE degeneration was blocked by antagonizing Alu RNA (Kaneko et al., 2011). Also, rescue of DICER1 knockdown-induced RPE degeneration by Alu RNA inhibition was not accompanied by restoration of microRNA deficits (Kaneko et al., 2011). Therefore, it was tested whether DICER1 also prevented NLRP3 inflammasome activation by Alu RNA. Alu RNA-induced Caspase-1 activation in human RPE cells was inhibited by DICER1 overexpression (FIGS. 6A and 6B). Conversely, Caspase-1 cleavage induced by DICER1 knockdown in human RPE cells was inhibited by simultaneous antisense knockdown of Alu RNA (FIGS. 12A and 12B).

Next the relevance of these pathways was tested in the context of DICER1 loss in vivo. Caspase-1 cleavage was increased in the RPE of BEST1 Cre; Dicer1$^{f/f}$ mice (FIG. 6C), which lose DICER1 expression in the RPE during development and exhibit RPE degeneration (Kaneko et al., 2011). Subretinal delivery of AAV1-BEST1-Cre in Dicer1$^{f/f}$ mice induced Caspase-1 activation and IL-18 maturation in the RPE (FIG. 6D). This treatment also induced RPE degeneration, which was blocked by intravitreous delivery of the Caspase-1-inhibitory peptide but not the control peptide (FIG. 6E). AAV1-BEST1-Cre-induced RPE degeneration in Dicer1$^{f/f}$ mice was also blocked by intravitreous delivery of the MyD88-inhibitory peptide but not a control peptide (FIG. 6F). In addition, MyD88 inhibition prevented cell death in human RPE cells treated with antisense oligonucleotides targeting DICER1 (FIG. 6G). DICER1 knockdown in human RPE cells increased IRAK1/4 phosphorylation, providing further evidence of MyD88 activation upon loss of DICER1 (FIG. 6H). MyD88 inhibition also prevented cell death in Dicer1$^{f/f}$ mouse RPE cells treated with an adenoviral vector coding for Cre recombinase (FIG. 6I). MyD88 inhibition blocked RPE cell death without restoring the microRNA expression deficits induced by Dicer1 knockdown (FIG. 6J). These findings demonstrate that DICER1 is an essential endogenous negative regulator of NLRP3 inflammasome activation, and that DICER1 deficiency leads to Alu RNA-mediated, MyD88-dependent, microRNA-independent RPE degeneration.

Inflammasome and MyD88 Activation in Human GA

Next it was tested whether human eyes with GA, which exhibit loss of DICER1 and accumulation of Alu RNA in their RPE (Kaneko et al., 2011), also display evidence of inflammasome activation. The abundance of NLRP3 mRNA in the RPE of human eyes with GA was markedly increased compared to control eyes (FIG. 7A). IL18 and IL1B mRNA abundance also was increased in GA RPE; however, only the disparity in IL18 levels reached statistical significance (FIG. 7A) Immunolocalization studies showed that the expression of NLRP3, PYCARD, and Caspase-1 proteins was also increased in GA RPE (FIGS. 7B-D). Western blot analyses corroborated the increased abundance of NLRP3 and PYCARD in GA RPE, and revealed greatly increased levels of the enzymatically active cleaved Caspase-1 p20 subunit in GA RPE (FIG. 7E). There was also an increase in the abundance of phosphorylated IRAK1 and IRAK4 in GA RPE, indicative of increased MyD88 signal transduction (FIG. 7E). Collectively, these data provide evidence of NLRP3 inflammasome and MyD88 activation in situ in human GA, mirroring the functional data in human RPE cell culture and mice in vivo.

Discussion

The data establish a functional role for the subversion of innate immune sensing pathways by Alu RNA in the pathogenesis of GA. Collectively, the findings demonstrate that the NLRP3 inflammasome senses GA-associated Alu RNA danger signals, contributes to RPE degeneration, and potentially vision loss in AMD (FIG. 13). To date, the function of the NLRP3 inflammasome has been largely restricted to immune cells in vivo. The finding that it plays a critical function in RPE cell survival broadens the cellular scope of this inflammasome and raises the possibility that other non-immune cells could employ this platform.

The NLRP3 inflammasome was originally recognized as a sensor of external danger signals such as microbial toxins (Kanneganti et al., 2006; Mariathasan et al., 2006; Muruve et al., 2008). Subsequently, endogenous crystals, polypeptides, and lipids were reported to activate it in diseases such as gout, atherogenesis, Alzheimer disease, and Type 2 diabetes (Halle et al., 2008; Masters et al., 2010; Muruve et al., 2008; Wen et al., 2011). To the knowledge, Alu RNA is the first endogenous nucleic acid known to activate this immune platform. The findings expand the diversity of endogenous danger signals in chronic human diseases, and comport with the concept that this inflammasome is a sensor of metabolic danger (Schroder et al., 2010).

Dampening inflammasome activation can be essential to limiting the inflammatory response. Pathogens have evolved many strategies to inhibit inflammasome activation (Martinon et al., 2009). Likewise, host autophagy proteins (Nakahira et al., 2011), Type I interferon (Guarda et al., 2011), and T cell contact with macrophages can inhibit this process (Guarda et al., 2009). The finding that DICER1, through its cleavage of Alu RNA, prevents activation of NLRP3 adds to the repertoire of host inflammasome modulation capabilities and reveals a new facet of how dysregulation of homeostatic anti-inflammatory mechanisms can promote AMD (Ambati et al., 2003; Takeda et al., 2009).

Added to its recently described anti-apoptotic and tumor-related functions, DICER1 emerges as a multifaceted protein. It remains to be determined how this functional versatility is channeled in various states. As DICER1 dysregulation is increasingly recognized in several human diseases, it is reasonable to imagine that Alu RNA might be an inflammasome activating danger signal in those conditions too. It is also interesting that, at least in adult mice and in a variety of mouse and human cells, the microRNA biogenesis function of DICER1 is not critical for cell survival, at least in a MyD88-deficient environment (data not shown).

The data that mitochondrial ROS production is involved in Alu RNA-induced RPE degeneration comport with observations of mitochondrial DNA damage (Lin et al., 2011), downregulation of proteins involved in mitochondrial energy production and trafficking (Nordgaard et al., 2008), and reduction in the number and size of mitochondria (Feher et al., 2006) in the RPE of human eyes with AMD. Jointly, these findings suggest a potential therapeutic benefit to interfering with mitochondrial ROS generation.

Current clinical programs targeting the inflammasome largely focus on IL-1β; presently there are no IL-18 inhibitors in registered clinical trials. However, the data indicate that IL-18 is more important than IL-1β in mediating RPE cell death in GA (similar to selective IL-18 involvement in a colitis model (Zaki et al., 2010)), pointing to the existence of regulatory mechanisms by which inflammasome activation bifurcates at the level of or just preceding the interleukin effectors. Although Caspase-1 inhibition could be an attractive local therapeutic strategy, caspase inhibitors can promote alternative cell death pathways, possibly limiting their utility (Vandenabeele et al., 2006).

MyD88 is best known for transducing TLR signaling initiated by pathogen associated molecular patterns (O'Neill and Bowie, 2007), although recently it has been implicated in human cancers (Ngo et al., 2011; Puente et al., 2011). The findings introduce an unexpected new function for MyD88 in effecting death signals from mobile element transcripts that can lead to retinal degeneration and blindness, and raise the possibility that MyD88 could be a central integrator of signals from other non-NLRP3 inflammasomes that also employ Caspase-1 (Schroder and Tschopp, 2010). Since non-canonical activation of MyD88 is a critical checkpoint in RPE degeneration in GA (FIG. 13), it represents an enticing therapeutic target. A potential concern is its important anti-microbial function in mice (O'Neill and Bowie, 2007). However, in contrast to Myd88$^{-/-}$ mice, adult humans with MyD88 deficiency are described to be generally healthy and resistant to a wide variety of microbial pathogens (von Bernuth et al., 2008). MyD88-deficient humans have a narrow susceptibility range to pyogenic bacterial infections, and that too only in early childhood and not adult life (Picard et al., 2010). Moreover, as evident from the siRNA and Myd88$^{+/-}$ studies, partial inhibition of MyD88 is sufficient to protect against Alu RNA. Localized intraocular therapy, the current standard of care in most retinal diseases, would further limit the likelihood of adverse infectious outcomes. It is reasonable to foresee development of MyD88 inhibitors for prevention or treatment of GA.

Experimental Procedures

Subretinal injection and imaging. Subretinal injections (1 µL) were performed using a Pico-Injector (PLI-100, Harvard Apparatus). Plasmids were transfected in vivo using 10% Neuroporter (Genlantis). Fundus imaging was performed on a TRC-50 IX camera (Topcon) linked to a digital imaging system (Sony). RPE flat mounts were immunolabeled using antibodies against zonula occludens-1 (Invitrogen).

mRNA Abundance.

Transcript abundance was quantified by real-time RT-PCR using an Applied Biosystems 7900 HT Fast Real-Time PCR system by the $2^{-\Delta\Delta Ct}$ method.

Protein Abundance and Activity.

Protein abundance was assessed by Western blot analysis using antibodies against Caspase-1 (1:500; Invitrogen), pIRAK1 (1:500; Thermo Scientific), pIRAK4 (1:500, Abbomax), PYCARD (1:200, Santa Cruz Biotechnology), NLRP3 (1:500, Enzo Life Sciences) and Vinculin (1:1,000; Sigma-Aldrich). Caspase-1 activity was visualized using Caspalux1 E1D2 (OncoImmunin) according to manufacturer's instructions.

Mice.

All animal experiments were approved by institutional review committees and in accordance with the Association for Research in Vision and Ophthalmology Statement for the Use of Animals in Ophthalmic and Visual Research. Wild-type C57BL/6J, Cybb$^{-/-}$, Tlr3$^{-/-}$, Tlr4$^{-/-}$ (C57BL/10ScNJ), Trif$^{-/-}$ (Ticam1$^{Lps2}$), Ifng$^{-/-}$, Ifngr1$^{-/-}$, Il1r1$^{-/-}$, Il18r1$^{-/-}$, Myd88$^{f/f}$, and Dicer1$^{f/f}$ mice were purchased from The Jackson Laboratory. Casp1$^{-/-}$, Nbp3$^{-/-}$, and Pycard$^{-/-}$ mice have been previously described (Kanneganti et al., 2006). Unc93b1 mutant mice were generously provided by B. A. Beutler via K. Fitzgerald. Myd88$^{-/-}$ and Tlr7$^{-/-}$ mice were generously provided by S. Akira via T. Hawn and D. T. Golenbock. Mda5$^{-/-}$ mice were generously provided by M. Colonna. mice were generously provided by B. R. Williams and R. L. Silverman. Mavs$^{-/-}$ mice were generously provided by Z. Chen via K. Fitzgerald. For all procedures, anesthesia was achieved by intraperitoneal injection of 100 mg/kg ketamine hydrochloride (Ft. Dodge Animal Health) and 10 mg/kg xylazine (Phoenix Scientific), and pupils were dilated with topical 1% tropicamide (Alcon Laboratories).

Fundus Photography.

Retinal photographs of dilated mouse eyes were taken with a TRC-50 IX camera (Topcon) linked to a digital imaging system (Sony).

Human Tissue.

Donor eyes or ocular tissues from patients with geographic atrophy due to AMD or age-matched patients without AMD were obtained from various eye banks. These diagnoses were confirmed by dilated ophthalmic examination prior to acquisition of the tissues or eyes or upon examination of the eye globes post mortem. The study followed the guidelines of the Declaration of Helsinki. Institutional review boards granted approval for allocation and histological analysis of specimens.

Immunolabeling.

Human eyes fixed in 2-4% paraformaldehyde were prepared as eyecups, cryoprotected in 30% sucrose, embedded in optimal cutting temperature compound (Tissue-Tek OCT; Sakura Finetek), and cryosectioned into 10 µm sections. Depigmentation was achieved using 0.25% potassium permanganate and 0.1% oxalic acid. Immunohistochemical staining was performed with the rabbit antibody against NLRP3 (1:100, Sigma Aldrich) or rabbit antibody against Caspase-1 (prediluted, AbCam). Isotype IgG was substituted for the primary antibody to assess the specificity of the staining. Bound antibody was detected with biotin-conjugated secondary antibodies, followed by incubation with ABC reagent and visualized by Vector Blue (Vector Laboratories). Levamisole (Vector Laboratories) was used to block endogenous alkaline phosphatase activity. Slides were washed in PBS, counterstained with neutral red (Fisher Scientific), rinsed with deionized water, air dried, and then mounted in Vectamount (Vector Laboratories). Fluorescent labeling of human tissue was performed with the rabbit antibody against PYCARD (1:50, Clone N-15, Santa Cruz Biotechnology) Immunolabeling was visualized by fluorescently conjugated anti-rabbit secondary antibody (Invitrogen). Tissue autofluorescence was quenched by incubating the sections in 0.3% Sudan black (Fisher Scientific). Sections were mounted in Vectashield with DAPI (Vector Laboratories). Mouse RPE/choroid flat mounts were fixed with 4% paraformaldehyde or 100% methanol, stained with rabbit antibodies against human zonula occludens-1 (1:100, Invitrogen) and visualized with Alexa594 (Invitrogen). All images were obtained using the Leica SP-5 or Zeiss Axio Observer Z1 microscopes.

Subretinal Injection.

Subretinal injections (1 µL) in mice were performed using a Pico-Injector (PLI-100, Harvard Apparatus). In vivo transfection of plasmids coding for two different Alu sequences (pAlu) or empty control vector (pNull) (Bennett et al., 2008; Kaneko et al., 2011; Shaikh et al., 1997) was achieved using 10% Neuroporter (Genlantis). AAV1-BEST1-Cre (Alexander and Hauswirth, 2008) or AAV1-BEST1-GFP were injected at $1.0\times10^{11}$ pfu/mL and in vitro transcribed Alu RNA was injected at 0.3 mg/mL.

Drug Treatments.

siRNAs formulated in siRNA buffer (20 mM KCL, 0.2 mM MgCl2 in HEPES buffer at pH 7.5; Dharmacon) or phosphate buffered saline (PBS; Sigma-Aldrich); the TLR4 antagonist Ultra Pure *Rhodobacter sphaeroides* LPS (LPS-RS, InvivoGen), a peptide inhibitor of MyD88 homodimerization IMG-2005 (IMGENEX), control inhibitor (IMGENEX), recombinant IL-18 (Medical & Biological Laboratories), neutralizing rat antibodies against mouse IL-1β (IMGENEX), neutralizing rat antibodies against mouse IL-18 (Medical & Biological Laboratories), isotype control IgGs (R&D Systems or eBioscience as appropriate), Caspase-1 inhibitor Z-WEHD-FMK (R&D Systems), Caspase control inhibitor Z-FA-FMK (R&D Systems), DPI (Enzo Life Sciences), Mito-TEMPO (Enzo Life Sciences), MitoQ and dTPP (both adsorbed to cyclodextrin and provided by M.P. Murphy, MRC Mitochondrial Biology Unit), and gp91ds-tat and scrambled gp91 ds-tat (both Anaspec), were dissolved in phosphate buffered saline (PBS; Sigma-Aldrich) or dimethyl sulfoxide (DMSO; Sigma-Aldrich), and injected into the vitreous humor in a total volume of 1 µL with a 33-gauge Exmire microsyringe (Ito Corporation). To assess the effect of MyD88 blockade on pAlu-induced RPE degeneration, 1 µL of cholesterol (chol) conjugated MyD88 siRNA (17+2 nt; 2 µg/µL) was intravitreously injected 1 day after pAlu injection. As a control, Luc siRNA-chol (17+2 nt) was used with identical dosages.

Bone Marrow Chimeras.

Bone marrow transplantation was used to create Myd88$^{-/-}$ chimera mice wherein the genetic deficiency of Myd88 was confined to either circulating cells (Myd88$^{-/-}$ →WT) or nonhematopoietic tissue (WT→Myd88$^{-/-}$). Briefly, bone marrows were collected from femur and tibia of congenic WT or Myd88$^{-/-}$ donor mice by flushing with RPMI1640. After two washing steps, cells were resuspended in RPMI1640. $1\times10^{7}$ cells in 150 µL of RPMI1640 were injected into the tail vein of irradiated donor mice. Two chimera groups were generated: WT→Myd88$^{-/-}$ (WT cells into Myd88$^{-/-}$ mice) and Myd88→WT (Myd88 cells into WT mice). 2 months after bone marrow transfer, mice were injected subretinally with Alu RNA, vehicle, pAlu, or pNull, and monitored for RPE degeneration 7 days later.

Real-Time PCR.

Total RNA was extracted from tissues or cells using Trizol reagent (Invitrogen) according to manufacturer's recommendations, DNase treated and reverse transcribed (QuantiTect, Qiagen). The RT products (cDNA) were amplified by real-time quantitative PCR (Applied Biosystems 7900 HT Fast Real-Time PCR system) with Power SYBR green Master Mix. Oligonucleotide primers specific for human IL1B (forward 5'-TTAAAGCCCGCCTGACAGA-3' and reverse 5'-GCGAATGACAGAGGGTTTCTTAG-3'), human IL18 (forward 5'-ATCACTTGCACTCCGGAG-GTA-3' and reverse 5'-AGAGCGCAATGGTGCAATC-3'), human NLRP3 (forward 5'-GCACCTGTTGTGCAATCT-GAA-3' and reverse 5'-TCCTGACAACATGCTGAT-GTGA-3'), human PYCARD (forward 5'-GCCAGGCCTG-CACTTTATAGA-3' and reverse 5'-GTTTGTGACCCTCGCGATAAG-3'), human VDAC1 (forward 5'-ACTGCAAAATCCCGAGTGAC-3' and reverse 5'-CTGTCCAGGCAAGATTGACA-3'), human VDAC2 (forward 5'-CAGTGCCAAATCAAAGCTGA-3' and reverse 5'-CCTGATGTCCAAGCAAGGTT-3'), human VDAC3 (forward 5'-TTGACACAGCCAAATCCAAA-3' and reverse 5'-GCCAAAACGGGTGTTGTTAC-3'), human 18S rRNA (forward 5'-CGCAGCTAGGAATAATG-GAATAGG-3' and reverse 5'-GCCTCAGTTCCGAAAAC-CAA-3'), mouse Myd88 (forward 5'-CACCTGTGTCTG-GTCCATTG-3' and reverse 5'-AGGCTGAGTGCAAACTTGGT-3'), mouse Nlrp3 (forward 5'-ATGCTGCTTCGACATCTCCT-3' and reverse 5'-AACCAATGCGAGATCCTGAC-3'), mouse Il18 (forward 5'-GACAGCCTGTGTTCGAGGAT-3' and reverse 5'-TGGATCCATTTCCTCAAAGG-3'), and mouse 18S rRNA (forward 5'-TTCGTATTGCGCCGCTAGA-3' and reverse 5'-CTTTCGCTCTGGTCCGTCTT-3') were used. The QPCR cycling conditions were 50° C. for 2 min, 95° C. for 10 min followed by 40 cycles of a two-step amplification program (95° C. for 15 s and 58° C. for 1 min). At the end of the amplification, melting curve analysis was applied using the dissociation protocol from the Sequence Detection system to exclude contamination with unspecific PCR products. The PCR products were also confirmed by agarose gel and showed only one specific band of the predicted size. For negative controls, no RT products were used as templates in the QPCR and verified by the absence of gel-detected bands. Relative expressions of target genes were determined by the $2^{-\Delta\Delta Ct}$ method.

miRNA Quantification.

Total RNA containing miRNAs was polyadenylated and reverse transcribed using universal primer using the All-In-One miRNA q-RT-PCR Detection Kit (GeneCopoeia) according to the manufacturer's specifications using a universal reverse primer in combination with the following forward primers: mouse miR-184 (5'-TGGACGGA-GAACTGATAAGGGT-3'); mouse miR-221/222 (5'-AGC-TACATCTGGCTACTGGGT-3'); mouse miR-320a (5'-AAAAGCTGGGTTGAGAGGGCGA-3'), and mouse miR-484 (5'-TCAGGCTCAGTCCCCTCCCGAT-3'). miRNA levels were normalized to levels of U6 snRNA (5'-AAAT-TCGTGAAGCGTTCC-3') using the $2^{-\Delta\Delta Ct}$ method. Detection was achieved by SYBR green qPCR with the following conditions: 95° C. for 10 min followed by 40 cycles of 95° C. for 10 s, 60° C. for 20 s and 72° C. for 20 s. Amplicon specificity was assessed by melt curve analysis and unique bands by agarose gel electrophoresis.

Western Blotting.

Tissues or cells were homogenized in lysis buffer (10 mM Tris base, pH 7.4, 150 mM NaCl, 1 mM EDTA, 1 mM EGTA, 1% Triton X-100, 0.5% NP-40, protease and phosphatase inhibitor cocktail (Roche)). Protein concentrations were determined using a Bradford assay kit (Bio-Rad) with bovine serum albumin as a standard. Proteins (40-100 µg) were run on NuPAGE Bis-Tris gels (Invitrogen) and transferred to Immun-Blot PVDF membranes (Bio-Rad). Cells were scraped in hot Laemmli buffer (62.5 mM Tris base, pH 6.8, 2% SDS, 5% 2-Mercaptoethanol, 10% Glycerol, 0.01% Bromophenol Blue). Samples were boiled and run on 4-20% NuPAGE Tris-Glycine gels (Invitrogen). The transferred membranes were blocked for 1 h at RT and incubated with antibodies against human Caspase-1 (1:500; Invitrogen), mouse Caspase 1 (1:500; MBL), NLRP3 (1:1000; Enzo Life Sciences), PYCARD (1:1000, RayBiotech), phospho-IRAK1 (S376) (1:500, Thermo Scientific), phospho-IRAK4 (T345) (1:500, AbboMax), DICER1 (1:2,000; Bethyl), MyD88 (1:1,000; Cell Signaling), and mouse IL-18 (1:200; MBL) at 4° C. overnight. Protein loading was assessed by immunoblotting using an anti-Vinculin antibody (1:1,000; Sigma-Aldrich). The secondary antibodies were used (1:5,000) for 1 h at RT. The signal was visualized by enhanced chemiluminescence (ECL plus) and captured by Vision-WorksLS Image Acquisition and Analysis software (Version 6.7.2, UVP, LLC).

Cell Culture.

All cell cultures were maintained at 37° C. and 5% $CO_2$. Primary mouse RPE cells were isolated as previously described (Yang et al., 2009) and grown in Dulbecco Modified Eagle Medium (DMEM) supplemented with 20% FBS and standard antibiotics concentrations. Primary human RPE cells were isolated as previously described (Yang et al., 2008) and maintained in DMEM supplemented with 10% FBS and antibiotics. HeLa cells were maintained in DMEM supplemented with 20% FBS and standard antibiotics concentrations. THP-1 cells were cultured in RPMI 1640 medium supplemented with 10% FBS and antibiotics.

In vitro transcription of Alu RNAs. Two Alu RNAs were synthesized: a 281 nt Alu sequence originating from the cDNA clone TS 103 (Shaikh et al., 1997) and a 302 nt Alu sequence isolated from the RPE of a human eye with geographic atrophy. Linearized plasmids containing these Alu sequences with an adjacent 5' T7 promoter were subjected to AmpliScribe™ T7-Flash™ Transcription Kit (Epicentre) according to the manufacturer's instructions. DNase-treated RNA was purified using MEGAclear™ (Ambion), and integrity was monitored by gel electrophoresis. This yields single stranded RNAs that fold into a defined secondary structure identical to Pol III derived transcripts. Where indicated, transcribed RNA was dephosphorylated using calf intestine alkaline phosphatase (Invitrogen) and repurified by Phenol:Chloroform:Isoamyl alcohol precipitation.

Transient Transfection.

Human or mouse RPE cells were transfected with pUC19, pAlu, pcDNA3.1/Dicer-FLAG, pcDNA3.1, Alu RNA, NLRP3 siRNA sense (5'-GUUUGACUAUCU-GUUCUdTdT-3'), PYCARD siRNA sense (5'-GAAGCUC-UUCAGUUUCAdTdT-3'), MyD88 siRNA sense (sense: 5'-CAGAGCAAGGAAUGUGAdTdT-3'), VDAC1 siRNA sense (5'-CGGAAUAGCAGCCAAGUdTdT-3'), VDAC2 siRNA sense (5'-CCCUGGAGUUGGAGGCUdTdT-3'), VDAC3 siRNA sense (5'-GCUUUAAUC-GAUGGGAAdTdT-3'), DICER1 antisense oligonucleotide (AS) (5'-GCUGACCTTTTTGCTUCUCA-3'), control (for DICER1) AS (5'-TTGGTACGCATACGTGTTGACT-GTGA-3'), Alu AS (5'-CCCGGG-TTCACGCCATTCTCCTGCCTCAGCCTCACGAGTAG-CTGGGACTACAGGCGCCCGACACCACTCCCG-GCTAATTTTTTGTATTTTT-3'), control (for Alu) AS (5'-GCATGGCCAGTCCATTGATCTTGCACGCTTGCCTA-GTACGCTCCTCAACCTATCCTCCTAGCCCGTTACT-TGGTGCCACCGGCG-3') using Lipofectamine 2000 (Invitrogen) according to the manufacturer's instructions.

Adenoviral Infection.

Cells were plated at density of $15 \times 10^3/cm^2$ and after 16 h, at approximately 50% confluence, were infected with AdCre or AdNull (Vector Laboratories) with a multiplicity of infection of 1,000.

Cell Viability.

MTS assays were performed using the CellTiter 96 AQueous One Solution Cell Proliferation Assay (Promega) according to the manufacturer's instructions. For examining the cytoprotective effect of glycine in Alu RNA induced cell death, human RPE cells were transfected with pNull/pAlu. At 6 h post-transfection the cells were incubated with complete media containing glycine (5 mM) or vehicle, and cell viability was assessed after 24 h. Similarly, human RPE cells primed with LPS (5 µg/ml for 6 h) were treated with ATP (25 µM) in the presence of glycine containing media (5 mM). 30 min post ATP cell viability was assessed as described above.

Caspase-1 activity. Caspase-1 activity was visualized by incubating cells with Caspalux1E1D2 reagent (Oncolmmunin) according to the manufacturer's instructions. Caspalux1E1D2 signal was quantified reading the fluorescence (excitation 552 nm, emission 580 nm) using a Synergy 4 reader (Biotek). Quantification of fluorescence from images was performed by converting images into grayscale in Adobe Photoshop CS5, and measuring the integrated density of black and white images using ImageJ software (NIH) (Bogdanovich et al., 2008).

ROS Production.

Cellular ROS production was assessed using the ROS-specific probe 2'7'-dichlorodihydrofluorescin diacetate ($H_2DCFDA$, BioChemica, Fluka). Mitochondrial ROS production was assessed using MitoSOX™ Red (Invitrogen). Sub-confluent human RPE cells were transfected with pNull or pAlu. After 24 h cells were loaded for 10 min at 37° C. with 10 µM $H_2DCFDA$ or MitoSOX™ Red (Invitrogen) mitochondrial superoxide indicator for live-cell imaging and washed twice with PBS. For $H_2DCFDA$, fluorescence was recorded in 96-well plate using with a Synergy 4 reader (Biotek) using a FITC filter (excitation 485 nm, emission 538 nm). To visualize respiring mitochondria for colocalization with the mitochondrial ROS signal, after PBS wash cells were incubated with MitoTracker Deep Red™ (Invitrogen) for 30 min at 37° C. and then washed twice with PBS. The fluorescent signals were detected using Leica SP-5 or Zeiss Axio Observer Z1 microscopes. Phagosomal ROS production was assessed using the Fc-OXYBURST Green™ assay (Invitrogen). Sub-confluent human RPE cells were transfected with pNull or pAlu, or treated with PMA (0.5 µg/ml; Sigma-Aldrich). The cells were incubated with Krebs-Ringer's PBS (KRP) at 37° C. for 20 min before adding Fc-OXYBURST Green™. The total fluorescence from the cells was measured immediately after adding Fc-OXYBURST Green™ with a Synergy 4 reader (Biotek) using FITC filter (excitation 485 nm, emission 538 nm).

RNA-Binding Protein Immunoprecipitation (RIP):

The physical interaction between NLRP3 and Alu RNA was examined using RNA ChIP-IT kit following the manufacturer's instructions (Active Motif). Briefly, human RPE cells were transfected with pAlu and pNLRP3-FLAG (provided by G. Núñez) and the protein-RNA complexes were immunoprecipitated with antibodies against NLRP3 (Enzo Life Sciences), FLAG (Sigma-Aldrich) or control IgG (Sigma-Aldrich). RNA isolated from these immunoprecipitates was analyzed by real-time RT-PCR using Alu-specific primers.

ELISA.

Secreted cytokine content in conditioned cell culture media was analyzed using the Human IL-1β and IL-18 ELISA Kits (R&D) according to the manufacturer's instructions.

TLR Screen.

A custom TLR ligand screen was performed by InvivoGen using HEK293 cells over-expressing individual TLR family members coupled with an AP-1/NF-κB reporter system. Cells were stimulated with each of two Alu RNAs synthesized by in vitro transcription, or a TLR-specific positive control ligand.

Statistics.

Results are expressed as mean±SEM, with p<0.05 considered statistically significant. Differences between groups were compared by using Mann-Whitney U test or Student t-test, as appropriate, and 2-tailed p values are reported.

Example 2

It was shown that both in vitro transcribed Alu RNA and a plasmid encoding Alu (pAlu) both induce RPE cell death by inducing IL-18 secretion, which triggers MyD88-dependent signaling that leads to Caspase-3 activation. Determine the intervening mechanistic steps in this cell death pathway were sought.

Caspase-8 is known to activate Caspase-3 (Stennicke et al. 1998). Therefore, it was tested whether Caspase-8 inhibition would inhibit RPE cell death or degeneration induced by Alu RNA or pAlu. It was found that the Caspase-8 inhibitory peptide Z-IETD-FMK, but not the control peptide Z-FA-FMK, blocked RPE degeneration induced by pAlu in wild-type mice (FIG. 14). Z-IETD-FMK also inhibited human RPE cell death induced by Alu RNA (FIG. 15) or pAlu (FIG. 16). It was also found that subretinal injection of recombinant IL-18 induced activation of Caspase-8, as monitored by a fluorometric assay, in the RPE of wild-type mice (FIG. 17). These data indicate that Alu RNA- or pAlu-induced IL-18 leads to Caspase-8 activation upstream of Caspase-3 activation.

MyD88 is known to bind Fas-associated death domain protein (FADD) and induce apoptosis via Caspase 8 (Aliprantis et al. 2000). Therefore, it was tested whether ablation of Fas (encoded by CD95) or FasL (encoded by Faslg) would inhibit RPE cell death or degeneration induced by Alu RNA, pAlu, or IL-18. It was found that neither pAlu (FIG. 18) nor Alu RNA (FIG. 19) induced RPE degeneration in CD95−/− (Fas$^{lpr}$) mice. In addition, recombinant IL-18 also did not induce RPE degeneration in CD95−/− (Fas$^{lpr}$) mice (FIG. 20). Likewise, pAlu (FIG. 21), Alu RNA (FIG. 22), and IL-18 (FIG. 23) did not induce RPE degeneration in Faslg−/− (Fasl$^{gld}$) mice.

It has been shown that Alu RNA induces RPE degeneration via the NLRP3 inflammasome. Because NF-κB activation is required for NLRP3 activation (Bauernfeind et al. 2009; Qiao et al. 2012), it was tested whether Alu RNA required NF-κB to induce RPE degeneration. Indeed, it was found that Alu RNA did not induce RPE degeneration in Nfkb1−/− mice, confirming that NF-κB activation is a critical step in this cell death pathway.

Experimental Procedures

Mice.

All animal experiments were approved by institutional review committees and in accordance with the Association for Research in Vision and Ophthalmology Statement for the Use of Animals in Ophthalmic and Visual Research. Wild-type C57BL/6J, Fas$^{-/-}$ (a.k.a CD95 or Fas$^{lpr}$) Faslg$^{-/-}$ (a.k.a. Fas$^{gld}$) and Nfkb1$^{-/-}$ mice were purchased from The Jackson Laboratory. For all procedures, anesthesia was achieved by intraperitoneal injection of 100 mg/kg ketamine hydrochloride (Ft. Dodge Animal Health) and 10 mg/kg xylazine (Phoenix Scientific), and pupils were dilated with topical 1% tropicamide (Alcon Laboratories).

Fundus Photography.

Retinal photographs of dilated mouse eyes were taken with a TRC-50 IX camera (Topcon) linked to a digital imaging system (Sony).

Subretinal Injection.

Subretinal injections (1 µL) in mice were performed using a Pico-Injector (PLI-100, Harvard Apparatus). In vivo transfection of plasmids coding for two different Alu sequences (pAlu) or empty control vector (pNull) (Bennett et al., 2008; Kaneko et al., 2011; Shaikh et al., 1997) was achieved using 10% Neuroporter (Genlantis). In vitro transcribed Alu RNA was injected at 0.3 mg/mL.

Drug Treatments.

Recombinant IL-18 (Medical & Biological Laboratories), Caspase-8 inhibitor Z-IETD-FMK (R&D Systems), Caspase control inhibitor Z-FA-FMK (R&D Systems), IRAK1/4 inhibitor (Calbiochem), were dissolved in phosphate buffered saline (PBS; Sigma-Aldrich) or dimethyl sulfoxide (DMSO; Sigma-Aldrich), and injected into the vitreous humor in a total volume of 1 µL with a 33-gauge Exmire microsyringe (Ito Corporation).

Cell Culture.

All cell cultures were maintained at 37° C. and 5% $CO_2$. Primary mouse RPE cells were isolated as previously described (Yang et al., 2009) and grown in Dulbecco Modified Eagle Medium (DMEM) supplemented with 20% FBS and standard antibiotics concentrations. Primary human RPE cells were isolated as previously described (Yang et al., 2008) and maintained in DMEM supplemented with 10% FBS and antibiotics. HeLa cells were maintained in DMEM supplemented with 20% FBS and standard antibiotics concentrations. THP-1 cells were cultured in RPMI 1640 medium supplemented with 10% FBS and antibiotics.

In Vitro Transcription of Alu RNAs.

We synthesized a 302 nt Alu sequence isolated from the RPE of a human eye with geographic atrophy. A linearized plasmid containing this Alu sequence with an adjacent 5' T7 promoter were subjected to AmpliScribe™ T7-Flash™ Transcription Kit (Epicentre) according to the manufacturer's instructions. DNase-treated RNA was purified using MEGAclear™ (Ambion), and integrity was monitored by gel electrophoresis. This yields single stranded RNAs that fold into a defined secondary structure identical to Pol III derived transcripts. Where indicated, transcribed RNA was dephosphorylated using calf intestine alkaline phosphatase (Invitrogen) and repurified by Phenol:Chloroform:Isoamyl alcohol precipitation.

Transient Transfection.

Human RPE cells were transfected with pUC19, pAlu, Alu RNA, VDAC1 siRNA sense (5'-CGGAAUAGCAGC-CAAGUdTdT-3'), VDAC2 siRNA sense (5'-CCCUG-GAGUUGGAGGCUdTdT-3'), VDAC3 siRNA sense (5'-GCUUUAAUCGAUGGGAAdTdT-3'), using Lipofectamine 2000 (Invitrogen) according to the manufacturer's instructions.

Cell Viability.

MTS assays were performed using the CellTiter 96 AQueous One Solution Cell Proliferation Assay (Promega) according to the manufacturer's instructions.

Caspase-8 Activity.

RPE tissues were homogenized in lysis buffer (10 mM Tris base, pH 7.4, 150 mM NaCl, 1 mM EDTA, 1 mM EGTA, 1% Triton X-100, 0.5% NP-40, protease and phosphatase inhibitor cocktail (Roche)). Protein concentrations were determined using a Bradford assay kit (Bio-Rad) with bovine serum albumin as a standard. The caspase-3 activity was measured using Caspase-8 Fluorimetric Assay (R&D) in according to the manufacturer's instructions.

Statistics.

Results are expressed as mean±SEM, with $p<0.05$ considered statistically significant. Differences between groups were compared by using Mann-Whitney U test or Student t-test, as appropriate, and 2-tailed p values are reported.

Methods for Caspase Imaging

Alu RNA or recombinant IL-18 was injected into the subretinal space of wild-type mice on day 0. DyeLight782-VAD-FMK3 (ThermoScientific), a probe that fluoresces in the presence of bioactive caspases, was injected into the vitreous humor of wild-type mice on day 2 or day 3 after injection.

Flat Mount Imaging.

At 24 hours after injection of DyeLight782-VAD-FMK3, the eyecup was dissected out of mice, the neural retina was removed, and a flat mount of the RPE was prepared, and viewed under a fluorescent microscope.

In Vivo Bioimaging in the Living Eye.

At intervals from 0-24 hours after injection of DyeLight782-VAD-FMK3, fundus photographs were taken with the Topcon 50IX camera using the ICG filter.

Throughout this document, various references are mentioned. All such references are incorporated herein by reference to the same extent as if each individual reference was specifically and individually indicated to be incorporated by reference, including the references set forth in the following list:

REFERENCES

1) Abreu, M. T., M. Fukata, et al. (2005). "TLR signaling in the gut in health and disease." J Immunol 174(8): 4453-4460.
2) Adachi, O., Kawai, T., Takeda, K., Matsumoto, M., Tsutsui, H., Sakagami, M., Nakanishi, K., and Akira, S. (1998). Targeted disruption of the MyD88 gene results in loss of IL-1- and IL-18-mediated function. Immunity 9, 143-150.
3) Aeffner, F., Z. P. Traylor, et al. (2011). "Double-stranded RNA induces similar pulmonary dysfunction to respiratory syncytial virus in BALB/c mice." Am J Physiol Lung Cell Mol Physiol 301(1): L99-L109.
4) Akira, S., Uematsu, S., and Takeuchi, O. (2006). Pathogen recognition and innate immunity. Cell 124, 783-801.
5) Alegre, M. L., J. Leemans, et al. (2008). "The multiple facets of toll-like receptors in transplantation biology." Transplantation 86(1): 1-9.
6) Alexander, J. J. & Hauswirth, W. W. Adeno-associated viral vectors and the retina. Adv Exp Med Biol 613, 121-128 (2008).
7) Alexopoulou, L., Holt, A. C., Medzhitov, R., and Flavell, R. A. (2001). Recognition of double-stranded RNA and activation of NF-kappaB by Toll-like receptor 3. Nature 413, 732-738.
8) Aliprantis, A. O., Yang, R. B., Weiss, D. S., et al. (2000). "The apoptotic signaling pathway activated by Toll-like receptor-2." EMBO J. 19(13): 3325-3336.
9) Allensworth, J. J., Planck, S. R., Rosenbaum, J. T., and Rosenzweig, H. L. (2011). Investigation of the differential potentials of TLR agonists to elicit uveitis in mice. J Leukoc Biol.
10) Ambati, J., Ambati, B. K., Yoo, S. H., Ianchulev, S., and Adamis, A. P. (2003). Age-related macular degeneration: etiology, pathogenesis, and therapeutic strategies. Sury Ophthalmol 48, 257-293.
11) Anders, H. J., B. Banas, et al. (2004). "Signaling danger: toll-like receptors and their potential roles in kidney disease." J Am Soc Nephrol 15(4): 854-867.
12) Anders, H. J. and D. Schlondorff (2007). "Toll-like receptors: emerging concepts in kidney disease." Curr Opin Nephrol Hypertens 16(3): 177-183.
13) Babu, S., C. P. Blauvelt, et al. (2005). "Diminished expression and function of TLR in lymphatic filariasis: a novel mechanism of immune dysregulation." J Immunol 175(2): 1170-1176.
14) Banas, M. C., B. Banas, et al. (2008). "TLR4 links podocytes with the innate immune system to mediate glomerular injury." J Am Soc Nephrol 19(4): 704-713.
15) Barrat, F. J. and R. L. Coffman (2008). "Development of TLR inhibitors for the treatment of autoimmune diseases." Immunol Rev 223: 271-283.
16) Batsford, S., U. Duermueller, et al. (2011). "Protein level expression of Toll-like receptors 2, 4 and 9 in renal disease." Nephrol Dial Transplant 26(4): 1413-1416.
17) Batzer, M. A., and Deininger, P. L. (2002). Alu repeats and human genomic diversity. Nat Rev Genet. 3, 370-379.
18) Bauernfeind, F., Bartok, E., Rieger, A., Franchi, L., Nunez, G., and Hornung, V. (2011). Cutting edge: reactive oxygen species inhibitors block priming, but not activation, of the NLRP3 inflammasome. J Immunol 187, 613-617.
19) Bauernfeind, F. G. et al. Cutting edge: NF-kappaB activating pattern recognition and cytokine receptors license NLRP3 inflammasome activation by regulating NLRP3 expression. J Immunol 183, 787-791 (2009).
20) Benedict, C. A. & Ware, C. F. Poxviruses aren't stuPYD Immunity 23, 553-555, doi:10.1016/j.immuni.2005.11.008 (2005).
21) Bennett, E. A., Keller, H., Mills, R. E., Schmidt, S., Moran, J. V., Weichenrieder, O., and Devine, S. E. (2008). Active Alu retrotransposons in the human genome. Genome Res 18, 1875-1883.

22) Bernstein, E., Caudy, A. A., Hammond, S. M., and Hannon, G. J. (2001). Role for a bidentate ribonuclease in the initiation step of RNA interference. Nature 409, 363-366.
23) Blaauwgeers, H. G., Holtkamp, G. M., Rutten, H., Witmer, A. N., Koolwijk, P., Partanen, T. A., Alitalo, K., Kroon, M. E., Kijlstra, A., van Hinsbergh, V. W., et al. (1999). Polarized vascular endothelial growth factor secretion by human retinal pigment epithelium and localization of vascular endothelial growth factor receptors on the inner choriocapillaris. Evidence for a trophic paracrine relation. Am J Pathol 155, 421-428.
24) Bogdanovich, S., McNally, E. M., and Khurana, T. S. (2008). Myostatin blockade improves function but not histopathology in a murine model of limb-girdle muscular dystrophy 2C. Muscle Nerve 37, 308-316.
25) Brichacek, B., C. Vanpouille, et al. (2010). "Contrasting roles for TLR ligands in HIV-1 pathogenesis." PLoS One 5(9).
26) Cao, Z., Henzel, W. J., and Gao, X. (1996). IRAK: a kinase associated with the interleukin-1 receptor. Science 271, 1128-1131.
27) Chen, C. J., Y. Shi, et al. (2006). "MyD88-dependent IL-1 receptor signaling is essential for gouty inflammation stimulated by monosodium urate crystals." J Clin Invest 116(8): 2262-2271.
28) Chen, H., E. Koustova, et al. (2007). "Differential effect of resuscitation on Toll-like receptors in a model of hemorrhagic shock without a septic challenge." Resuscitation 74(3): 526-537.
29) Cremer, J., M. Martin, et al. (1996). "Systemic inflammatory response syndrome after cardiac operations." Ann Thorac Surg 61(6): 1714-1720.
30) Cristofaro, P. and S. M. Opal (2003). "The Toll-like receptors and their role in septic shock." Expert Opin Ther Targets 7(5): 603-612.
31) Curtiss, L. K. and P. S. Tobias (2009). "Emerging role of Toll-like receptors in atherosclerosis." J Lipid Res 50 Suppl: S340-345.
32) de Rivero Vaccari, J. P., Lotocki, G., Marcillo, A. E., Dietrich, W. D. & Keane, R. W. A molecular platform in neurons regulates inflammation after spinal cord injury. J Neurosci 28, 3404-3414, doi:10.1523/JNEUROSCI.0157-08.2008 (2008).
33) Devaraj, S., P. Tobias, et al. (2011). "Knockout of Toll-Like Receptor-2 Attenuates Both the Proinflammatory State of Diabetes and Incipient Diabetic Nephropathy." Arterioscler Thromb Vasc Biol.
34) Dhellin, O., Maestre, J., and Heidmann, T. (1997). Functional differences between the human LINE retrotransposon and retroviral reverse transcriptases for in vivo mRNA reverse transcription. EMBO J. 16, 6590-6602.
35) Diebold, S. S., Kaisho, T., Hemmi, H., Akira, S., and Reis e Sousa, C. (2004). Innate antiviral responses by means of TLR7-mediated recognition of single-stranded RNA. Science 303, 1529-1531.
36) Dorfleutner, A. et al. A Shope Fibroma virus PYRIN-only protein modulates the host immune response. Virus Genes 35, 685-694, doi:10.1007/s11262-007-0141-9 (2007).
37) Dorfleutner, A. et al. Cellular pyrin domain-only protein 2 is a candidate regulator of inflammasome activation. Infect Immun 75, 1484-1492, doi:10.1128/IAI.01315-06 (2007).
38) Dostert, C. et al. Innate immune activation through Nalp3 inflammasome sensing of asbestos and silica. Science 320, 674-677, doi:10.1126/science.1156995 (2008).
39) Dostert, C. et al. Malarial hemozoin is a Nalp3 inflammasome activating danger signal. PLoS One 4, e6510, doi:10.1371/journal.pone.0006510 (2009).
40) Dybdahl, B., A. Wahba, et al. (2002). "Inflammatory response after open heart surgery: release of heat-shock protein 70 and signaling through toll-like receptor-4." Circulation 105(6): 685-690.
41) El-Achkar, T. M. and P. C. Dagher (2006). "Renal Toll-like receptors: recent advances and implications for disease." Nat Clin Pract Nephrol 2(10): 568-581.
42) Feher, J., Kovacs, I., Artico, M., Cavallotti, C., Papale, A., and Balacco Gabrieli, C. (2006). Mitochondrial alterations of retinal pigment epithelium in age-related macular degeneration. Neurobiol Aging 27, 983-993.
43) Feldmeyer, L., Keller, M., Niklaus, G., Hohl, D., Werner, S., and Beer, H. D. (2007). The inflammasome mediates UVB-induced activation and secretion of interleukin-1beta by keratinocytes. Curr Biol 17, 1140-1145.
44) Fernandes-Alnemri, T., Wu, J., Yu, J. W., Datta, P., Miller, B., Jankowski, W., Rosenberg, S., Zhang, J., and Alnemri, E. S. (2007). The pyroptosome: a supramolecular assembly of ASC dimers mediating inflammatory cell death via caspase-1 activation. Cell Death Differ 14, 1590-1604.
45) Ferrara, N. Vascular endothelial growth factor and age-related macular degeneration: from basic science to therapy. Nat Med 16, 1107-1111 (2010).
46) Fink, S. L., Bergsbaken, T., and Cookson, B. T. (2008). Anthrax lethal toxin and *Salmonella* elicit the common cell death pathway of caspase-1-dependent pyroptosis via distinct mechanisms. Proc Natl Acad Sci USA 105, 4312-4317.
47) Fink, S. L., and Cookson, B. T. (2006). Caspase-1-dependent pore formation during pyroptosis leads to osmotic lysis of infected host macrophages. Cell Microbiol 8, 1812-1825.
48) Franklin, B. S., S. T. Ishizaka, et al. (2011). "Therapeutical targeting of nucleic acid-sensing Toll-like receptors prevents experimental cerebral malaria." Proc Natl Acad Sci USA 108(9): 3689-3694.
49) Frantz, S., K. A. Vincent, et al. (2005). "Innate immunity and angiogenesis." Circ Res 96(1): 15-26.
50) Fresno, M., R. Alvarez, et al. (2011). "Toll-like receptors, inflammation, metabolism and obesity." Arch Physiol Biochem 117(3): 151-164.
51) Geraghty, P., A. J. Dabo, et al. (2011). "TLR-4 contributes to cigarette smoke (CS) induced matrix metalloproteinase-1 (MMP-1) expression in chronic obstructive pulmonary disease." J Biol. Chem.
52) Ghanim, H., P. Mohanty, et al. (2008). "Acute modulation of toll-like receptors by insulin." Diabetes Care 31(9): 1827-1831.
53) Ghayur, T., Banerjee, S., Hugunin, M., Butler, D., Herzog, L., Carter, A., Quintal, L., Sekut, L., Talanian, R., Paskind, M., et al. (1997). Caspase-1 processes IFN-gamma-inducing factor and regulates LPS-induced IFN-gamma production. Nature 386, 619-623.
54) Gregory, S. M. et al. Discovery of a viral NLR homolog that inhibits the inflammasome. Science 331, 330-334, doi:10.1126/science.1199478 (2011).
55) Gu, Y., Kuida, K., Tsutsui, H., Ku, G., Hsiao, K., Fleming, M. A., Hayashi, N., Higashino, K., Okamura, H., Nakanishi, K., et al. (1997). Activation of interferon- 56) Guarda, G., Braun, M., Staehli, F., Tardivel, A., Mattmann, C., Forster, I., Farlik, M., Decker, T., Du Pasquier, R. A., Romero, P., et al. (2011). Type I interferon inhibits interleukin-1 production and inflammasome activation. Immunity 34, 213-223.
57) Guarda, G., Dostert, C., Staehli, F., Cabalzar, K., Castillo, R., Tardivel, A., Schneider, P., and Tschopp, J. (2009). T cells dampen innate immune responses through inhibition of NLRP1 and NLRP3 inflammasomes. Nature 460, 269-273.
58) Guo, H., J. Gao, et al. (2011). "Toll-like receptor 2 siRNA suppresses corneal inflammation and attenuates *Aspergillus fumigatus* keratitis in rats." Immunol Cell Biol.
59) Halle, A., Hornung, V., Petzold, G. C., Stewart, C. R., Monks, B. G., Reinheckel, T., Fitzgerald, K. A., Latz, E., Moore, K. J., and Golenbock, D. T. (2008). The NALP3 inflammasome is involved in the innate immune response to amyloid-beta. Nat Immunol 9, 857-865.
60) Heil, F., Hemmi, H., Hochrein, H., Ampenberger, F., Kirschning, C., Akira, S., Lipford, G., Wagner, H., and Bauer, S. (2004). Species-specific recognition of single-stranded RNA via toll-like receptor 7 and 8. Science 303, 1526-1529.
61) Hilbi, H., Chen, Y., Thirumalai, K. & Zychlinsky, A. The interleukin 1beta-converting enzyme, caspase 1, is activated during *Shigella flexneri*-induced apoptosis in human monocyte-derived macrophages. Infect Immun 65, 5165-5170 (1997).
62) Hoebe, K., Du, X., Georgel, P., Janssen, E., Tabeta, K., Kim, S. O., Goode, J., Lin, P., Mann, N., Mudd, S., et al. (2003). Identification of Lps2 as a key transducer of MyD88-independent TIR signalling. Nature 424, 743-748.
63) Hornung, V., Ellegast, J., Kim, S., Brzozka, K., Jung, A., Kato, H., Poeck, H., Akira, S., Conzelmann, K. K., Schlee, M., et al. (2006). 5'-Triphosphate RNA is the ligand for RIG-I. Science 314, 994-997.
64) Humke, E. W., Shriver, S. K., Starovasnik, M. A., Fairbrother, W. J. & Dixit, V. M. ICEBERG: a novel inhibitor of interleukin-1beta generation. Cell 103, 99-111 (2000).
65) Hurtado, P. R., L. Jeffs, et al. (2008). "CpG oligodeoxynucleotide stimulates production of anti-neutrophil cytoplasmic antibodies in ANCA associated vasculitis." BMC Immunol 9: 34.
66) Hutton, M. J., G. Soukhatcheva, et al. (2010). "Role of the TLR signaling molecule TRIF in beta-cell function and glucose homeostasis." Islets 2(2): 104-111.
67) Jenssens et al. Regulation of Interleukin-1- and Lipopolysaccharide-Induced NF-κB Activation by Alternative Splicing of MyD88. Current Biology 2002; 12:467-71.
68) Jiang, J., Stoyanovsky, D. A., Belikova, N. A., Tyurina, Y. Y., Zhao, Q., Tungekar, M. A., Kapralova, V., Huang, Z., Mintz, A. H., Greenberger, J. S., et al. (2009). A mitochondria-targeted triphenylphosphonium-conjugated nitroxide functions as a radioprotector/mitigator. Radiat Res 172, 706-717.
69) Johnston, J. B. et al. A poxvirus-encoded pyrin domain protein interacts with ASC-1 to inhibit host inflammatory and apoptotic responses to infection Immunity 23, 587-598, doi:10.1016/j.immuni.2005.10.003 (2005).
70) Juliana, C. et al. Anti-inflammatory compounds parthenolide and Bay 11-7082 are direct inhibitors of the inflammasome. J Biol Chem 285, 9792-9802, doi: 10.1074/jbc.M109.082305 (2010).
71) Kanakaraj, P., Ngo, K., Wu, Y., Angulo, A., Ghazal, P., Harris, C. A., Siekierka, J. J., Peterson, P. A., and Fung-Leung, W. P. (1999). Defective interleukin (IL)-18-mediated natural killer and T helper cell type 1 responses in IL-1 receptor-associated kinase (IRAK)-deficient mice. J Exp Med 189, 1129-1138.
72) Kaneko, H., Dridi, S., Tarallo, V., Gelfand, B. D., Fowler, B. J., Cho, W. G., Kleinman, M. E., Ponicsan, S. L., Hauswirth, W. W., Chiodo, V. A., et al. (2011). DICER1 deficit induces Alu RNA toxicity in age-related macular degeneration. Nature 471, 325-330.
73) Kanneganti, T. D., Ozoren, N., Body-Malapel, M., Amer, A., Park, J. H., Franchi, L., Whitfield, J., Barchet, W., Colonna, M., Vandenabeele, P., et al. (2006). Bacterial RNA and small antiviral compounds activate caspase-1 through cryopyrin/Nalp3. Nature 440, 233-236.
74) Kato, H., Takeuchi, O., Sato, S., Yoneyama, M., Yamamoto, M., Matsui, K., Uematsu, S., Jung, A., Kawai, T., Ishii, K. J., et al. (2006). Differential roles of MDA5 and RIG-I helicases in the recognition of RNA viruses. Nature 441, 101-105.
75) Keller, M., Ruegg, A., Werner, S., and Beer, H. D. (2008). Active caspase-1 is a regulator of unconventional protein secretion. Cell 132, 818-831.
76) Kettle, S. et al. Vaccinia virus serpin B13R(SPI-2) inhibits interleukin-1beta-converting enzyme and protects virus-infected cells from TNF- and Fas-mediated apoptosis, but does not prevent IL-1beta-induced fever. J Gen Virol 78 (Pt 3), 677-685 (1997).
77) Kleinman, M. E., Kaneko, H., Cho, W. G., Dridi, S., Fowler, B. J., Blandford, A. D., Albuquerque, R. J., Hirano, Y., Terasaki, H., Kondo, M., et al. (2012). Short-interfering RNAs Induce Retinal Degeneration via TLR3 and IRF3. Mol. Ther. 20, 101-108.
78) Kleinman, M. E. et al. Short interfering RNAs induce retinal degeneration via TLR3 and IRF3. Mol Ther, In press (2011).
79) Kleinman, M. E., Yamada, K., Takeda, A., Chandrasekaran, V., Nozaki, M., Baffi, J. Z., Albuquerque, R. J., Yamasaki, S., Itaya, M., Pan, Y., et al. (2008). Sequence- and target-independent angiogenesis suppression by siRNA via TLR3. Nature 452, 591-597.
80) Knuefermann, P., S, Nemoto, et al. (2002). "Cardiac inflammation and innate immunity in septic shock: is there a role for toll-like receptors?" Chest 121(4): 1329-1336.
81) Komiyama, T. et al. Inhibition of interleukin-1 beta converting enzyme by the cowpox virus serpin CrmA. An example of cross-class inhibition. J Biol Chem 269, 19331-19337 (1994).
82) Krams, S. M., M. Wang, et al. (2010). "Toll-like receptor 4 contributes to small intestine allograft rejection." Transplantation 90(12): 1272-1277.
83) Krieg, A. M. et al. Sequence motifs in adenoviral DNA block immune activation by stimulatory CpG motifs. Proc Natl Acad Sci USA 95, 12631-12636 (1998).
84) Krutzik, S. R., B. Tan, et al. (2005). "TLR activation triggers the rapid differentiation of monocytes into macrophages and dendritic cells." Nat Med 11(6): 653-660.
85) Kumar, H., Kawai, T., Kato, H., Sato, S., Takahashi, K., Coban, C., Yamamoto, M., Uematsu, S., Ishii, K. J., Takeuchi, O., et al. (2006). Essential role of IPS-1 in innate immune responses against RNA viruses. J Exp Med 203, 1795-1803.

86) Kumar, M. V., Nagineni, C. N., Chin, M. S., Hooks, J. J., and Detrick, B. (2004). Innate immunity in the retina: Toll-like receptor (TLR) signaling in human retinal pigment epithelial cells. J Neuroimmunol 153, 7-15.

87) Lamkanfi, M. et al. Glyburide inhibits the Cryopyrin/Nalp3 inflammasome. J Cell Biol 187, 61-70, doi: 10.1083/jcb.200903124 (2009).

88) Lander, E. S., Linton, L. M., Birren, B., Nusbaum, C., Zody, M. C., Baldwin, J., Devon, K., Dewar, K., Doyle, M., FitzHugh, W., et al. (2001). Initial sequencing and analysis of the human genome. Nature 409, 860-921.

89) Latz, E. (2010). NOX-free inflammasome activation. Blood 116, 1393-1394.

90) Lee, S. H., Stehlik, C. & Reed, J. C. Cop, a caspase recruitment domain-containing protein and inhibitor of caspase-1 activation processing. J Biol Chem 276, 34495-34500, doi:10.1074/jbc.M101415200 (2001).

91) Li, H., Ambade, A. & Re, F. Cutting edge: Necrosis activates the NLRP3 inflammasome. J Immunol 183, 1528-1532, doi:10.4049/jimmunol.0901080 (2009).

92) Li, Y., and Trush, M. A. (1998). Diphenyleneiodonium, an NAD(P)H oxidase inhibitor, also potently inhibits mitochondrial reactive oxygen species production. Biochem Biophys Res Commun 253, 295-299.

93) Li, M., Y. Zhou, et al. (2009). "The critical role of Toll-like receptor signaling pathways in the induction and progression of autoimmune diseases." Curr Mol Med 9(3): 365-374.

94) Lim, B. J., D. Lee, et al. (2011). "Toll-Like Receptor 4 Signaling is Involved in IgA-Stimulated Mesangial Cell Activation." Yonsei Med J 52(4): 610-615.

95) Lin, H., Xu, H., Liang, F. Q., Liang, H., Gupta, P., Havey, A. N., Boulton, M. E., and Godley, B. F. (2011). Mitochondrial DNA damage and repair in RPE associated with aging and age-related macular degeneration. Invest Ophthalmol V is Sci 52, 3521-3529.

96) Liu, H. Z., H. Z. Yang, et al. (2010). "Toll like receptor 2 mediates bleomycin-induced acute lung injury, inflammation and fibrosis in mice." Yao Xue Xue Bao 45(8): 976-986.

97) Loiarro, M., Sette, C., Gallo, G., Clacci, A., Fanto, N., Mastroianni, D., Carminati, P., and Ruggiero, V. (2005). Peptide-mediated interference of TIR domain dimerization in MyD88 inhibits interleukin-1-dependent activation of NF-κB. J Biol Chem 280, 15809-15814.

98) Lopez, P. F., Sippy, B. D., Lambert, H. M., Thach, A. B., and Hinton, D. R. (1996). Transdifferentiated retinal pigment epithelial cells are immunoreactive for vascular endothelial growth factor in surgically excised age-related macular degeneration-related choroidal neovascular membranes. Invest Ophthalmol V is Sci 37, 855-868.

99) Mariathasan, S. et al. Differential activation of the inflammasome by caspase-1 adaptors ASC and Ipaf. Nature 430, 213-218 (2004).

100) Mariathasan, S., Weiss, D. S., Newton, K., McBride, J., O'Rourke, K., Roose-Girma, M., Lee, W. P., Weinrauch, Y., Monack, D. M., and Dixit, V. M. (2006). Cryopyrin activates the inflammasome in response to toxins and ATP. Nature 440, 228-232.

101) Martin, S. F., J. C. Dudda, et al. (2008). "Toll-like receptor and IL-12 signaling control susceptibility to contact hypersensitivity." J Exp Med 205(9): 2151-2162.

102) Martinon, F., Mayor, A., and Tschopp, J. (2009). The inflammasomes: guardians of the body. Annu Rev Immunol 27, 229-265.

103) Martinon, F., Petrilli, V., Mayor, A., Tardivel, A. & Tschopp, J. Gout-associated uric acid crystals activate the NALP3 inflammasome. Nature 440, 237-241, doi: 10.1038/nature04516 (2006).

104) Masters, S. L., Dunne, A., Subramanian, S. L., Hull, R. L., Tannahill, G. M., Sharp, F. A., Becker, C., Franchi, L., Yoshihara, E., Chen, Z., et al. (2010). Activation of the NLRP3 inflammasome by islet amyloid polypeptide provides a mechanism for enhanced IL-1beta in type 2 diabetes. Nat Immunol 11, 897-904.

105) McKernan, D. P., A. Nolan, et al. (2009). "Toll-like receptor mRNA expression is selectively increased in the colonic mucosa of two animal models relevant to irritable bowel syndrome." PLoS One 4(12): e8226.

106) McLeod, D. S., Grebe, R., Bhutto, I., Merges, C., Baba, T., and Lutty, G. A. (2009). Relationship between RPE and choriocapillaris in age-related macular degeneration. Invest Ophthalmol V is Sci 50, 4982-4991.

107) Medvedev, A. E., I. Sabroe, et al. (2006). "Tolerance to microbial TLR ligands: molecular mechanisms and relevance to disease." J Endotoxin Res 12(3): 133-150.

108) Meissner, F., Seger, R. A., Moshous, D., Fischer, A., Reichenbach, J., and Zychlinsky, A. (2010). Inflammasome activation in NADPH oxidase defective mononuclear phagocytes from patients with chronic granulomatous disease. Blood 116, 1570-1573.

109) Meng, G., F. Zhang, et al. (2009). "A mutation in the Nlrp3 gene causing inflammasome hyperactivation potentiates Th17 cell-dominant immune responses." Immunity 30(6): 860-874.

110) Messud-Petit, F. et al. Serp2, an inhibitor of the interleukin-1beta-converting enzyme, is critical in the pathobiology of myxoma virus. J Virol 72, 7830-7839 (1998).

111) Mhyre, A. J., Marcondes, A. M., Spaulding, E. Y. & Deeg, H. J. Stroma-dependent apoptosis in clonal hematopoietic precursors correlates with expression of PYCARD. Blood 113, 649-658, doi:10.1182/blood-2008-04-152686 (2009).

112) Miao, E. A., Leaf, I. A., Treuting, P. M., Mao, D. P., Dors, M., Sarkar, A., Warren, S. E., Wewers, M. D., and Aderem, A. (2010). Caspase-1-induced pyroptosis is an innate immune effector mechanism against intracellular bacteria. Nat Immunol 11, 1136-1142.

113) Miller, D. M., A. A. Rossini, et al. (2008). "Role of innate immunity in transplantation tolerance." Crit. Rev Immunol 28(5): 403-439.

114) Munding, C. et al. The estrogen-responsive B box protein: a novel enhancer of interleukin-1beta secretion. Cell Death Differ 13, 1938-1949, doi:10.1038/sj.cdd.4401896 (2006).

115) Murphy, M. P. (2009). How mitochondria produce reactive oxygen species. Biochem J 417, 1-13.

116) Murphy, M. P., and Smith, R. A. (2007). Targeting antioxidants to mitochondria by conjugation to lipophilic cations. Annu Rev Pharmacol Toxicol 47, 629-656.

117) Muruve, D. A., Petrilli, V., Zaiss, A. K., White, L. R., Clark, S. A., Ross, P. J., Parks, R. J., and Tschopp, J. (2008). The inflammasome recognizes cytosolic microbial and host DNA and triggers an innate immune response. Nature 452, 103-107.

118) Muzio, M., Ni, J., Feng, P., and Dixit, V. M. (1997). IRAK (Pelle) family member IRAK-2 and MyD88 as proximal mediators of IL-1 signaling. Science 278, 1612-1615.

119) Nakahira, K., Haspel, J. A., Rathinam, V. A., Lee, S. J., Dolinay, T., Lam, H. C., Englert, J. A., Rabinovitch, M., Cernadas, M., Kim, H. P., et al. (2011). Autophagy proteins regulate innate immune responses by inhibiting 119) the release of mitochondrial DNA mediated by the NALP3 inflammasome. Nat Immunol 12, 222-230.

120) Newman, Z. L. et al. Auranofin protects against anthrax lethal toxin-induced activation of the Nlrp1b inflammasome. Antimicrob Agents Chemother 55, 1028-1035, doi:10.1128/AAC.00772-10 (2011).

121) Ngo, V. N., Young, R. M., Schmitz, R., Jhavar, S., Xiao, W., Lim, K. H., Kohlhammer, H., Xu, W., Yang, Y., Zhao, H., et al. (2011). Oncogenically active MYD88 mutations in human lymphoma. Nature 470, 115-119.

122) Nogueira-Machado, J. A., C. M. Volpe, et al. (2011). "HMGB1, TLR and RAGE: a functional tripod that leads to diabetic inflammation." Expert Opin Ther Targets 15(8): 1023-1035.

123) Nordgaard, C. L., Karunadharma, P. P., Feng, X., Olsen, T. W., and Ferrington, D. A. (2008). Mitochondrial proteomics of the retinal pigment epithelium at progressive stages of age-related macular degeneration. Invest Ophthalmol V is Sci 49, 2848-2855.

124) Novick, D. et al. Interleukin-18 binding protein: a novel modulator of the Th1 cytokine response. Immunity 10, 127-136 (1999).

125) O'Neill, L. A., and Bowie, A. G. (2007). The family of five: TIR-domain-containing adaptors in Toll-like receptor signalling. Nat Rev Immunol 7, 353-364.

126) O'Neill, L. A. (2008). "Primer: Toll-like receptor signaling pathways—what do rheumatologists need to know?" Nat Clin Pract Rheumatol 4(6): 319-327.

127) Opal, S. M. and C. E. Huber (2002). "Bench-to-bedside review: Toll-like receptors and their role in septic shock." Crit. Care 6(2): 125-136.

128) Papin, S. et al. The SPRY domain of Pyrin, mutated in familial Mediterranean fever patients, interacts with inflammasome components and inhibits proIL-1beta processing. Cell Death Differ 14, 1457-1466, doi:10.1038/sj.cdd.4402142 (2007).

129) Park, J. H., D. R. Gold, et al. (2001). "House dust endotoxin and wheeze in the first year of life." Am J Respir Crit. Care Med 163(2): 322-328.

130) Parker, J. S., Roe, S. M., and Barford, D. (2004). Crystal structure of a PIWI protein suggests mechanisms for siRNA recognition and slicer activity. EMBO J. 23, 4727-4737.

131) Picard, C., von Bernuth, H., Ghandil, P., Chrabieh, M., Levy, O., Arkwright, P. D., McDonald, D., Geha, R. S., Takada, H., Krause, J. C., et al. (2010). Clinical features and outcome of patients with IRAK-4 and MyD88 deficiency. Medicine (Baltimore) 89, 403-425.

132) Pichlmair, A., Lassnig, C., Eberle, C. A., Gorna, M. W., Baumann, C. L., Burkard, T. R., Burckstummer, T., Stefanovic, A., Krieger, S., Bennett, K. L., et al. (2011). IFIT1 is an antiviral protein that recognizes 5'-triphosphate RNA. Nat Immunol 12, 624-630.

133) Puente, X. S., Pinyol, M., Quesada, V., Conde, L., Ordonez, G. R., Villamor, N., Escaramis, G., Jares, P., Bea, S., Gonzalez-Diaz, M., et al. (2011). Whole-genome sequencing identifies recurrent mutations in chronic lymphocytic leukaemia. Nature 475, 101-105.

134) Qiao, Y., Wang, P., Qi, J., et al. (2012). "TLR-induced NF-kappaB activation regulates NLRP3 expression in murine macrophages." FEBS Lett 586(7): 1022-1026.

135) Qureshi, N., Takayama, K., and Kurtz, R. (1991). Diphosphoryl lipid A obtained from the nontoxic lipopolysaccharide of Rhodopseudomonas sphaeroides is an endotoxin antagonist in mice. Infect Immun 59, 441-444.

136) Rahman, M. M., Mohamed, M. R., Kim, M., Smallwood, S. & McFadden, G. Co-regulation of NF-kappaB and inflammasome-mediated inflammatory responses by myxoma virus pyrin domain-containing protein M013. PLoS Pathog 5, e1000635, doi:10.1371/journal.ppat.1000635 (2009).

137) Rakoff-Nahoum, S. & Medzhitov, R. Regulation of spontaneous intestinal tumorigenesis through the adaptor protein MyD88. Science 317, 124-127 (2007).

138) Reuter, B. K. and T. T. Pizarro (2004). "Commentary: the role of the IL-18 system and other members of the IL-1R/TLR superfamily in innate mucosal immunity and the pathogenesis of inflammatory bowel disease: friend or foe?" Eur J Immunol 34(9): 2347-2355.

139) Rey, F. E., Cifuentes, M. E., Kiarash, A., Quinn, M. T., and Pagano, P. J. (2001). Novel competitive inhibitor of NAD(P)H oxidase assembly attenuates vascular O(2)(−) and systolic blood pressure in mice. Circ Res 89, 408-414.

140) Robson, M. G. (2009). "Toll-like receptors and renal disease." Nephron Exp Nephrol 113(1): el-7.

141) Saleh, M. et al. Enhanced bacterial clearance and sepsis resistance in caspase-12-deficient mice. Nature 440, 1064-1068, doi:10.1038/nature04656 (2006).

142) Savina, A., Jancic, C., Hugues, S., Guermonprez, P., Vargas, P., Moura, I. C., Lennon-Dumenil, A. M., Seabra, M. C., Raposo, G., and Amigorena, S. (2006). NOX2 controls phagosomal pH to regulate antigen processing during crosspresentation by dendritic cells. Cell 126, 205-218.

143) Schmid, M. C., C. J. Avraamides, et al. (2011). "Receptor Tyrosine Kinases and TLR/IL1Rs Unexpectedly Activate Myeloid Cell PI3 Kgamma, A Single Convergent Point Promoting Tumor Inflammation and Progression." Cancer Cell 19(6): 715-727.

144) Schorn, C. et al. Sodium overload and water influx activate the NALP3 inflammasome. J Biol Chem 286, 35-41, doi:10.1074/jbc.M110.139048 (2011).

145) Schroder, K., and Tschopp, J. (2010). The inflammasomes. Cell 140, 821-832.

146) Schroder, K., Zhou, R., and Tschopp, J. (2010). The NLRP3 inflammasome: a sensor for metabolic danger? Science 327, 296-300.

147) Shaikh, T. H., Roy, A. M., Kim, J., Batzer, M. A., and Deininger, P. L. (1997). cDNAs derived from primary and small cytoplasmic Alu (scAlu) transcripts. J Mol Biol 271, 222-234.

148) Shaikh, T. H., Roy, A. M., Kim, J., Batzer, M. A. & Deininger, P. L. cDNAs derived from primary and small cytoplasmic Alu (scAlu) transcripts. J Mol Biol 271, 222-234 (1997).

149) Shin, O. S, and J. B. Harris (2011). "Innate immunity and transplantation tolerance: the potential role of TLRs/NLRs in GVHD." Korean J Hematol 46(2): 69-79.

150) Sinnett, D., Richer, C., Deragon, J. M., and Labuda, D. (1991). Alu RNA secondary structure consists of two independent 7 SL RNA-like folding units. J Biol Chem 266, 8675-8678.

151) Slater, J. E., E. J. Paupore, et al. (1998). "Lipopolysaccharide augments IgG and IgE responses of mice to the latex allergen Hey b 5." J Allergy Clin Immunol 102(6 Pt 1): 977-983.

152) Smith, W., Assink, J., Klein, R., Mitchell, P., Klayer, C. C., Klein, B. E., Hofman, A., Jensen, S., Wang, J. J., and de Jong, P. T. (2001). Risk factors for age-related macular degeneration: Pooled findings from three continents. Ophthalmology 108, 697-704.

153) Stasakova, J. et al. Influenza A mutant viruses with altered NS1 protein function provoke caspase-1 activation in primary human macrophages, resulting in fast apoptosis and release of high levels of interleukins 1beta and 18. J Gen Virol 86, 185-195, doi:10.1099/vir.0.80422-0 (2005).

154) Stehlik, C. et al. The PAAD/PYRIN-only protein POP1/ASC2 is a modulator of ASC-mediated nuclear-factor-kappa B and pro-caspase-1 regulation. Biochem J 373, 101-113, doi:10.1042/BJ20030304 (2003).

155) Streilein, J. W. (2003). Ocular immune privilege: therapeutic opportunities from an experiment of nature. Nat Rev Immunol 3, 879-889.

156) Stennicke, H. R., Jurgensmeier, J. M., Shin, H., et al. (1998). "Pro-caspase-3 is a major physiologic target of caspase-8." J Biol Chem 273(42): 27084-27090.

157) Summers, S. A., 0. M. Steinmetz, et al. (2011). "Toll-like receptor 2 induces Th17 myeloperoxidase autoimmunity while Toll-like receptor 9 drives Th1 autoimmunity in murine vasculitis." Arthritis Rheum 63(4): 1124-1135.

158) Sun, D., and Ding, A. (2006). MyD88-mediated stabilization of interferon-gamma-induced cytokine and chemokine mRNA. Nat Immunol 7, 375-381.

159) Sun, Q., Sun, L., Liu, H. H., Chen, X., Seth, R. B., Forman, J., and Chen, Z. J. (2006). The specific and essential role of MAVS in antiviral innate immune responses Immunity 24, 633-642.

160) Suzuki, N., Chen, N. J., Millar, D. G., Suzuki, S., Horacek, T., Hara, H., Bouchard, D., Nakanishi, K., Penninger, J. M., Ohashi, P. S., et al. (2003). IL-1 receptor-associated kinase 4 is essential for IL-18-mediated NK and Th1 cell responses J Immunol 170, 4031-4035.

161) Suzuki, N., Suzuki, S., Duncan, G. S., Millar, D. G., Wada, T., Mirtsos, C., Takada, H., Wakeham, A., Itie, A., Li, S., et al. (2002). Severe impairment of interleukin-1 and Toll-like receptor signalling in mice lacking IRAK-4. Nature 416, 750-756.

162) Tabeta, K., Hoebe, K., Janssen, E. M., Du, X., Georgel, P., Crozat, K., Mudd, S., Mann, N., Sovath, S., Goode, J., et al. (2006). The Unc93b1 mutation 3d disrupts exogenous antigen presentation and signaling via Toll-like receptors 3, 7 and 9. Nat Immunol 7, 156-164.

163) Takeda, A., Baffi, J. Z., Kleinman, M. E., Cho, W. G., Nozaki, M., Yamada, K., Kaneko, H., Albuquerque, R. J., Dridi, S., Saito, K., et al. (2009). CCR3 is a target for age-related macular degeneration diagnosis and therapy. Nature 460, 225-230.

164) Tan, H. H., M. I. Fiel, et al. (2009). "Kupffer cell activation by ambient air particulate matter exposure may exacerbate non-alcoholic fatty liver disease." J Immunotoxicol 6(4): 266-275.

165) Tarallo V, Hirano Y, Gelfand B D, Dridi S, Kerur N, Kim Y, Cho W G, Kaneko H, Fowler B J, Bogdanovich S, Albuquerque R J, Hauswirth W W, Chiodo V A, Kugel J F, Goodrich J A, Ponicsan S L, Chaudhuri G, Murphy M P, Dunaief J L, Ambati B K, Ogura Y, Yoo J W, Lee D K, Provost P, Hinton D R, Núñez G, Baffi J Z, Kleinman M E, Ambati J. (2012). DICER1 loss and Alu RNA induce age-related macular degeneration via the NLRP3 inflammasome and MyD88. Cell 149(4):847-859.

166) Taylor, K. M. (1996). "SIRS—the systemic inflammatory response syndrome after cardiac operations." Ann Thorac Surg 61(6): 1607-1608.

167) Taylor, P. A., M. J. Ehrhardt, et al. (2008). "TLR agonists regulate alloresponses and uncover a critical role for donor APCs in allogeneic bone marrow rejection." Blood 112(8): 3508-3516.

168) Terhorst, D., B. N. Kalali, et al. (2010). "The role of toll-like receptors in host defenses and their relevance to dermatologic diseases." Am J Clin Dermatol 11(1): 1-10.

169) Testro, A. G., K. Visvanathan, et al. (2011). "Acute allograft rejection in human liver transplant recipients is associated with signaling through toll-like receptor 4." J Gastroenterol Hepatol 26(1): 155-163.

170) Thornberry, N. A., Bull, H. G., Calaycay, J. R., Chapman, K. T., Howard, A. D., Kostura, M. J., Miller, D. K., Molineaux, S. M., Weidner, J. R., Aunins, J., et al. (1992). A novel heterodimeric cysteine protease is required for interleukin-1 beta processing in monocytes. Nature 356, 768-774.

171) Tilich, M. and R. R. Arora (2011). "Modulation of Toll-Like Receptors by Insulin." Am J. Ther.

172) Trnka, J., Blaikie, F. H., Logan, A., Smith, R. A., and Murphy, M. P. (2009). Antioxidant properties of Mito-TEMPOL and its hydroxylamine Free Radic Res 43, 4-12.

173) Tschopp, J., Martinon, F., and Burns, K. (2003). NALPs: a novel protein family involved in inflammation. Nat Rev Mol Cell Biol 4, 95-104.

174) Tschopp, J., and Schroder, K. (2010). NLRP3 inflammasome activation: The convergence of multiple signalling pathways on ROS production? Nat Rev Immunol 10, 210-215.

175) van Bruggen, R., Koker, M. Y., Jansen, M., van Houdt, M., Roos, D., Kuijpers, T. W., and van den Berg, T. K. (2010). Human NLRP3 inflammasome activation is Noxy-4 independent. Blood 115, 5398-5400.

176) Vandanmagsar, B. et al. The NLRP3 inflammasome instigates obesity-induced inflammation and insulin resistance. Nat Med 17, 179-188 (2011).

177) Vandenabeele, P., Vanden Berghe, T., and Festjens, N. (2006). Caspase inhibitors promote alternative cell death pathways. Sci STKE 2006, pe44.

178) Ventura, G. M., V. Balloy, et al. (2009). "Lack of MyD88 protects the immunodeficient host against fatal lung inflammation triggered by the opportunistic bacteria *Burkholderia* cenocepacia." J Immunol 183(1): 670-676.

179) Venugopal, P. G., T. B. Nutman, et al. (2009). "Activation and regulation of toll-like receptors (TLRs) by helminth parasites." Immunol Res 43(1-3): 252-263.

180) Verhoef, P. A., Kertesy, S. B., Lundberg, K., Kahlenberg, J. M., and Dubyak, G. R. (2005). Inhibitory effects of chloride on the activation of caspase-1, IL-1beta secretion, and cytolysis by the P2X7 receptor. J Immunol 175, 7623-7634.

181) Vogt, S. D., Curcio, C. A., Wang, L., Li, C. M., McGwin, G., Jr., Medeiros, N. E., Philp, N. J., Kimble, J. A., and Read, R. W. (2011). Retinal pigment epithelial expression of complement regulator CD46 is altered early in the course of geographic atrophy. Exp Eye Res.

182) von Bernuth, H., Picard, C., Jin, Z., Pankla, R., Xiao, H., Ku, C. L., Chrabieh, M., Mustapha, I. B., Ghandil, P., Camcioglu, Y., et al. (2008). Pyogenic bacterial infections in humans with MyD88 deficiency. Science 321, 691-696.

183) von Herrath, M., C. Filippi, et al. (2011). "How viral infections enhance or prevent type 1 diabetes-from mouse to man." J Med Virol 83(9): 1672.

184) Wang, S., C. Schmaderer, et al. (2010). "Recipient Toll-like receptors contribute to chronic graft dysfunction by both MyD88- and TRIF-dependent signaling." Dis Model Mech 3(1-2): 92-103.

185) Wen, H., Gris, D., Lei, Y., Ma, S., Zhang, L., Huang, M. T., Brickey, W. J., and Ting, J. P. (2011). Fatty acid-induced NLRP3-ASC inflammasome activation interferes with insulin signaling. Nat Immunol 12, 408-415.

186) Weyand, C. M., W. Ma-Krupa, et al. (2005). "Vascular dendritic cells in giant cell arteritis." Ann N Y Acad Sci 1062: 195-208.

187) Wong, K. W. & Jacobs, W. R., Jr. Critical role for NLRP3 in necrotic death triggered by *Mycobacterium tuberculosis*. Cell Microbiol 13, 1371-1384, doi:10.1111/j.1462-5822.2011.01625.x (2011).

188) Yamamoto, M., Sato, S., Hemmi, H., Hoshino, K., Kaisho, T., Sanjo, H., Takeuchi, O., Sugiyama, M., Okabe, M., Takeda, K., et al. (2003). Role of adaptor TRIF in the MyD88-independent toll-like receptor signaling pathway. Science 301, 640-643.

189) Yang, P., Tyrrell, J., Han, I. & Jaffe, G. J. Expression and modulation of RPE cell membrane complement regulatory proteins. Invest Ophthalmol V is Sci 50, 3473-3481 (2009).

190) Yang, Y. L., Reis, L. F., Pavlovic, J., Aguzzi, A., Schafer, R., Kumar, A., Williams, B. R., Aguet, M., and Weissmann, C. (1995). Deficient signaling in mice devoid of double-stranded RNA-dependent protein kinase. EMBO J. 14, 6095-6106.

191) Yang, Z. et al. Toll-like receptor 3 and geographic atrophy in age-related macular degeneration. N Engl J Med 359, 1456-1463 (2008).

192) Yokoi, S., H. Niizeki, et al. (2009). "Adjuvant effect of lipopolysaccharide on the induction of contact hypersensitivity to haptens in mice." J Dermatol Sci 53(2): 120-128.

193) Young, J. L. et al. The serpin proteinase inhibitor 9 is an endogenous inhibitor of interleukin 1beta-converting enzyme (caspase-1) activity in human vascular smooth muscle cells. J Exp Med 191, 1535-1544 (2000).

194) Zaki, M. H., Boyd, K. L., Vogel, P., Kastan, M. B., Lamkanfi, M., and Kanneganti, T. D. (2010). The NLRP3 inflammasome protects against loss of epithelial integrity and mortality during experimental colitis. Immunity 32, 379-391.

195) Zhang, L., Lu, R., Zhao, G., Pflugfelder, S. C. & Li, D. Q. TLR-mediated induction of pro-allergic cytokine IL-33 in ocular mucosal epithelium. Int J Biochem Cell Biol 43, 1383-1391, doi:10.1016/j.biocel.2011.06.003 (2011).

196) Zhou, R., Yazdi, A. S., Menu, P., and Tschopp, J. (2011). A role for mitochondria in NLRP3 inflammasome activation. Nature 469, 221-225.

197) Zuany-Amorim, C., J. Hastewell, et al. (2002). "Toll-like receptors as potential therapeutic targets for multiple diseases." Nat Rev Drug Discov 1(10): 797-807.

198) International Patent Application Publication No. WO 2008/070579 for Inhibition of Brain Enzymes Involved in Cerebral Amyloid Angiopathy and Macular Degeneration.

199) U.S. Provisional Patent Application No. 61/396,747, filed Jun. 1, 2010.

200) U.S. Provisional Patent Application No. 61/432,110, filed Jan. 12, 2011.

201) U.S. Provisional Patent Application No. 61/432,948, filed Jan. 14, 2011.

202) International Patent Application No. PCT/US11/38753, filed Jun. 1, 2011.

203) U.S. Provisional Patent Application No. 61/508,867, filed Jul. 18, 2011.

204) U.S. Provisional Patent Application No. 61/543,038, filed Oct. 4, 2011.

205) U.S. Provisional Patent Application No. 61/586,427, filed Jan. 13, 2012.

It will be understood that various details of the presently disclosed subject matter can be changed without departing from the scope of the subject matter disclosed herein. Furthermore, the foregoing description is for the purpose of illustration only, and not for the purpose of limitation.

---

What is claimed is:

1. A method of protecting an retinal pigment epithelium (RPE) cell, a retinal photoreceptor cell, or a choroidal cell, comprising:
   inhibiting one or more of an inflammasome of the cell; MyD88 of the cell; IL-18 of the cell; VDAC1 of the cell; VDAC2 of the cell; caspase-8 of the cell; and NFκB of the cell;
   wherein the cell is protected against Alu-RNA-induced degeneration;
   wherein inhibiting the inflammasome consists essentially of administering an inflammasome inhibitor selected from the group consisting of an NLRP3 inhibitor, a PYCARD inhibitor, an inflammosome inhibitor comprising a sequence selected from the sequences of SEQ ID NOS: 7-16, an inhibitor of Caspase-1, a peptide inhibitor of Caspase-1, a Caspase-1 inhibitor comprising the sequence of SEQ ID NO: 17, and the inflammosome inhibitors selected from: ion channel inhibitors; IkB-α inhibitors; antibodies selected from: Anti-ASC, Anti-NALP1, antibodies based on protein sequences selected from: ASC: ALR QTQ PYL VTD LEQ S; NALP1: MEE SQS KEE SNT EG-cys; Anti-NALP1, anti-IL-1β, anti-IL-18, anti-caspase-1, and anti-caspase-11; direct inhibitors of Caspase-1 and/or NLRP3; parthenolide; estrogen binding B-box proteins, COP, ICEBERG, and Z-WEHD-FMK; Caspase 1 and/or 4 inhibitors; Caspase-12 inhibitors; host-derived inhibitors of caspase-1; inhibitors of Nlrp1b inflammasome; virus expressed inhibitors of the inflammasome; potassium chloride; Cathepsin-B-inhibitors; Cytochalsin D; ROS inhibitors; ASC-1 inhibitors; NLRP3 inflammasome pan-caspase inhibitors; Microtubules; an isolated double-stranded RNA molecule that inhibits expression of NLRP3, and which can be conjugated to cholesterol or not, and at least one strand including the sequence: GUUUGACUAUCUGUUCUdTdT (SEQ ID NO: 7); an isolated double-stranded RNA molecule that inhibits expression of PYCARD, at least one strand of which includes the sequence of: 5'-GAAGCUCUUCAGUUUCAdTdT-3' (SEQ ID NO: 12); and an isolated double-stranded RNA molecule that inhibits expression of PYCARD, at least one strand of which includes a sequence selected from: 5'-GAAGCUCUUCAGUUUCAdTdT-3' (SEQ ID NO: 12); 5'-GGCUGCUGGAUGCUCUGUACGGGAA-3' (SEQ ID NO: 13); and 5'-UUCCCGUACAGAGCAUCCAGCAGCC-3' (SEQ ID NO: 14).

2. The method of claim 1, wherein the inhibiting MyD88 comprises administering a MyD88 inhibitor.

3. The method of claim 2, wherein the inhibitor is selected from the group consisting of a MyD88 inhibitor comprising a polypeptide sequence selected from the sequences of SEQ ID NO: 1, 54, 55, 60, and 61; and a MyD88 inhibitor comprising a double-stranded RNA molecule, at least one strand of which includes a sequence selected from SEQ ID NOS: 3, 4, 5, 6, and 56.

4. The method of claim 2, wherein the My D88 inhibitor is selected from the group consisting of a MyD88 homodimerization inhibitor; Pepinh-MYD; a dominant negative or splice variant of MyD88; a MyD88 splice variants that lack exon 2; and MyD88 inhibitors as set forth in Table C.

5. The method of claim 4, wherein the inhibitor is administered by intravitreous injection; subretinal injection; episcleral injection; sub-Tenon's injection; retrobulbar injection; peribulbar injection; topical eye drop application; release from a sustained release implant device that is sutured to or attached to or placed on the sclera, or injected into the vitreous humor, or injected into the anterior chamber, or implanted in the lens bag or capsule; oral administration; or intravenous administration.

6. A method of protecting an RPE cell, a retinal photoreceptor cell, or a choroidal cell, comprising:
   inhibiting one or more of an inflammasome of the cell; MyD88 of the cell; IL-18 of the cell; VDAC1 of the cell; VDAC2 of the cell; caspase-8 of the cell; and NFκB of the cell;
   wherein the cell is protected against Alu-RNA-induced degeneration;
   wherein inhibiting the inflammasome comprises administering an inflammasome inhibitor selected from the group consisting of an NLRP3 inhibitor, a PYCARD inhibitor, an inflammosome inhibitor comprising a sequence selected from the sequences of SEQ ID NOS: 7-16, an inhibitor of Caspase-1, a peptide inhibitor of Caspase-1, a Caspase-1 inhibitor comprising the sequence of SEQ ID NO: 17, and the inflammosome inhibitors selected from: ion channel inhibitors; IkB-α inhibitors; antibodies selected from: Anti-ASC, Anti-NALP1, antibodies based on protein sequences selected from: ASC: ALR QTQ PYL VTD LEQ S; NALP1: MEE SQS KEE SNT EG-cys; Anti-NALP1, anti-IL-1β, anti-IL-18, anti-caspase-1, and anti-caspase-11; direct inhibitors of Caspase-1 and/or NLRP3; parthenolide; estrogen binding B-box proteins, COP, ICEBERG, and Z-WEHD-FMK; Caspase 1 and/or 4 inhibitors; Caspase-12 inhibitors; host-derived inhibitors of caspase-1; inhibitors of Nlrp1b inflammasome; virus expressed inhibitors of the inflammasome; potassium chloride; Cathepsin-B-inhibitors; Cytochalsin D; ROS inhibitors; ASC-1 inhibitors; NLRP3 inflammasome pan-caspase inhibitors; Microtubules; an isolated double-stranded RNA molecule that inhibits expression of NLRP3, and which can be conjugated to cholesterol or not, and at least one strand including the sequence: GUUUGACUAUCUGUUCUdTdT (SEQ ID NO: 7); an isolated double-stranded RNA molecule that inhibits expression of PYCARD, at least one strand of which includes the sequence of: 5'-GAAGCUC-UUCAGUUUCAdTdT-3' (SEQ ID NO: 12); and an isolated double-stranded RNA molecule that inhibits expression of PYCARD, at least one strand of which includes a sequence selected from: 5'-GAAGCUC-UUCAGUUUCAdTdT-3' (SEQ ID NO: 12); 5'-GGCUGCUGGAUGCUCUGUACGGGAA-3' (SEQ ID NO: 13); and 5'-UUCCCGUACAGAG-CAUCCAGCAGCC-3' (SEQ ID NO: 14), wherein the inflammasome includes a protein encoded by PYCARD.

7. The method of claim 6, wherein the inflammasome is selected from NLRP3 inflammasome, NLRP1 inflammasome, NLRC4 inflammasome, AIM2 inflammasome, and IFI16 inflammasome.

8. The method of claim 7, wherein the inflammasome is the NLRP3 inflammasome.

9. The method of claim 1, wherein the inflammasome inhibitor is selected from glybenclamide/glyburide; BAY11-7082 (CAS Number: 195462-67-7; also known as (E)-3-(4-Methylphenylsulfonyl)-2-propenenitrile); Anti-ASC and Anti-NALP1 and antibodies based on protein sequences selected from: ASC: ALR QTQ PYL VTD LEQ S; NALP1: MEE SQS KEE SNT EG-cys; Anti-NALP1, anti-IL-1β, anti-IL-18, anti-caspase-1, and anti-caspase-11; parthenolide; estrogen binding B-box proteins, COP, ICEBERG, and Z-WEHD-FMK; Ac-Tyr-Val-Ala-Asp-CHO (Ac-YVAD-CHO) or N-acetyl-L-tyrosyl-L-valyl-N-[(1S)-1-(carboxymethyl)-3-chloro-2-oxo-propyl]-L-alaninamide (Ac-YVAD-CMK); Caspase-12 inhibitors; cellular PYRIN domain (PYD)-ony proteins (POP) family: cPOP1 and cPOP2; serpin proteinase inhibitor 9 (PI-9); BCL-2 and BCL-xL; auranofin; PYD homologs M13L-PYD, S013L, SPI-2 homologs CrmA, Serp2, SPI-2, NS1, Kaposi Sarcoma-associated Herpesvirus Orf63; potassium chloride; L-3-trans-(Propylcarbamoyl)oxirane-2-Carbonyl)-L-Isoleucyl-L-Proline Methyl Ester ("CA-074 Me"); Cytochalsin D; N-acetyl-L-cysteine (NAC), (2R,4R)-4-aminopyrrolidine-2,4-dicarboxylate (APDC); cellular pyrin domain (PYD) superfamily proteins, also known as M013; Z-VAD-FMK; colchicine; an isolated double-stranded RNA molecule that inhibits expression of NLRP3, and which can be conjugated to cholesterol or not, and at least one strand including the sequence: GUUUGACUAUCUGUUCUdTdT (SEQ ID NO: 7); an isolated double-stranded RNA molecule that inhibits expression of PYCARD, at least one strand of which includes the sequence of: 5'-GAAGCUCUUCAGUUU-CAdTdT-3' (SEQ ID NO: 12); and an isolated double-stranded RNA molecule that inhibits expression of PYCARD, at least one strand of which includes a sequence selected from: 5'-GAAGCUCUUCAGUUUCAdTdT-3' (SEQ ID NO: 12); 5'-GGCUGCUGGAUGCUCU-GUACGGGAA-3' (SEQ ID NO: 13); and 5'-UUC-CCGUACAGAGCAUCCAGCAGCC-3' (SEQ ID NO: 14).

10. The method of claim 1, wherein the inflammasome inhibitor is selected from the group consisting of an inflammosome inhibitor comprising a sequence selected from the sequences of SEQ ID NOS: 7-16; an inhibitor of Caspase-1 selected from VX-765, ML132, VX-740, VRT-018858, YVAD, WEHD; and a Caspase-1 inhibitor comprising the sequence of SEQ ID NO: 17.

11. The method of claim 9, wherein the inhibitor is administered by intravitreous injection; subretinal injection; episcleral injection; sub-Tenon's injection; retrobulbar injection; peribulbar injection; topical eye drop application; release from a sustained release implant device that is sutured to or attached to or placed on the sclera, or injected into the vitreous humor, or injected into the anterior chamber, or implanted in the lens bag or capsule; oral administration; or intravenous administration.

12. The method of claim 1, wherein the inhibiting IL-18 comprises administering an IL-18 inhibitor.

13. The method of claim 12, wherein the IL-18 inhibitor is selected from the group consisting of a neutralizing antibody against IL-18; an antibody that blocks IL-18 binding to the IL-18 receptor, IL-18 neutralizing antibodies; IL-18 binding protein; and IL18BP.

14. The method of claim 13, wherein the inhibitor is administered by intravitreous injection; subretinal injection; episcleral injection; sub-Tenon's injection; retrobulbar injection; peribulbar injection; topical eye drop application; release from a sustained release implant device that is sutured to or attached to or placed on the sclera, or injected into the vitreous humor, or injected into the anterior chamber, or implanted in the lens bag or capsule; oral administration; or intravenous administration.

15. The method of claim 1, wherein the inhibiting VDAC1 comprises administering a VDAC1 inhibitor and inhibiting VDAC2 comprises administering a VDAC2 inhibitor.

16. The method of claim 15, wherein the VDAC1 inhibitor is selected from the group consisting of a VDAC1 inhibitor comprising the sequence of SEQ ID NO: 47; a VDAC2 inhibitor comprising the sequence of SEQ ID NO: 48; phosphorothioate oligonucleotide randomer (Trilink Industries) that inhibits VDAC; cyclosporin A; superoxide dismutase 1; 4,4'-diisothiocyanatostilbene-2,2'-disulfonic acid (DIDS); Bcl-x(L) BH4(4-23); and TRO19622.

17. The method of claim 15, wherein the inhibitor is administered by intravitreous injection; subretinal injection; episcleral injection; sub-Tenon's injection; retrobulbar injection; peribulbar injection; topical eye drop application; release from a sustained release implant device that is sutured to or attached to or placed on the sclera, or injected into the vitreous humor, or injected into the anterior chamber, or implanted in the lens bag or capsule; oral administration; or intravenous administration.

18. The method of claim 1, wherein the inhibiting Caspase-8 comprises administering a Caspase-8 inhibitor.

19. The method of claim 18, wherein the Caspase-8 inhibitor is selected from the group consisting of Z-IETD-FMK, Ac-Ala-Ala-Val-Ala-Leu-Leu-Pro-Ala-Val-Leu-Leu-Ala-Leu-Leu-Ala-Pro-Ile-Glu-Thr-Asp-CHO, Z-Ile-Glu(OMe)-Thr-Asp(OMe)-$CH_2F$, and Cellular fas-associated death domain-like interleukin-1-β-converting enzyme-inhibitory protein (L).

20. The method of any one of claim 18, wherein the inhibitor is administered by intravitreous injection; subretinal injection; episcleral injection; sub-Tenon's injection; retrobulbar injection; peribulbar injection; topical eye drop application; release from a sustained release implant device that is sutured to or attached to or placed on the sclera, or injected into the vitreous humor, or injected into the anterior chamber, or implanted in the lens bag or capsule; oral administration; or intravenous administration.

21. The method of claim 1, wherein the inhibiting NFkB comprises administering a NFkB inhibitor.

22. The method of claim 21, wherein the inhibitor is administered by intravitreous injection; subretinal injection; episcleral injection; sub-Tenon's injection; retrobulbar injection; peribulbar injection; topical eye drop application;

release from a sustained release implant device that is sutured to or attached to or placed on the sclera, or injected into the vitreous humor, or injected into the anterior chamber, or implanted in the lens bag or capsule; oral administration; or intravenous administration.

23. The method of claim 1, wherein the cell is in a subject.

24. The method of claim 23, wherein the subject has age-related macular degeneration.

25. An molecule selected from the group consisting of:
an isolated double-stranded RNA molecule that inhibits expression of MyD88, wherein a first strand of the double-stranded RNA comprises a sequence selected from SEQ ID NO: 3, 4, 5, 6, and 56, and including about 11 to 27 nucleotides;
an isolated double-stranded RNA molecule that inhibits expression of NLRP3 and/or PYCARD, wherein a first strand of the double-stranded RNA comprises a sequence selected from SEQ ID NO: 7-14, and including about 11 to 27 nucleotides;
an isolated double-stranded RNA molecule that inhibits expression of Pyrin, comprising the sequence of SEQ ID NO: 15, and including about 11 to 27 nucleotides;
an isolated double-stranded RNA molecule that inhibits expression of NALP3, comprising the sequence of SEQ ID NO: 16, and including about 11 to 27 nucleotides;
an isolated double-stranded RNA molecule that inhibits expression of caspase-1, comprising the sequence of SEQ ID NO: 17, and including about 11 to 27 nucleotides;
an isolated double-stranded RNA molecule that inhibits expression of VDAC1 and/or VDAC2, wherein a first strand of the double-stranded RNA comprises a sequence selected from SEQ ID NO: 47 and 48, and including about 11 to 27 nucleotides;
a polypeptide molecule that inhibits MyD88, comprising a sequence selected from SEQ ID NO: 60 and SEQ ID NO: 61.

* * * * *